(12) United States Patent
Hyde et al.

(10) Patent No.: US 9,724,483 B2
(45) Date of Patent: Aug. 8, 2017

(54) METHOD FOR ADMINISTERING AN INHALABLE COMPOUND

(75) Inventors: Roderick A. Hyde, Redmond, WA (US); Muriel Y. Ishikawa, Livermore, CA (US); Jordin T. Kare, Seattle, WA (US); Robert Langer, Newton, MA (US); Eric C. Leuthardt, St. Louis, MO (US); Elizabeth A. Sweeney, Seattle, WA (US); Clarence T. Tegreene, Mercer Island, WA (US); Lowell L. Wood, Jr., Bellevue, WA (US); Victoria Y. H. Wood, Livermore, CA (US)

(73) Assignee: Gearbox, LLC, Bellevue, WA (US)

( * ) Notice: Subject to any disclaimer, the term of this patent is extended or adjusted under 35 U.S.C. 154(b) by 1785 days.

(21) Appl. No.: 12/455,672

(22) Filed: Jun. 4, 2009

(65) Prior Publication Data
US 2010/0163040 A1 Jul. 1, 2010

Related U.S. Application Data

(63) Continuation-in-part of application No. 12/317,934, filed on Dec. 30, 2008, now abandoned, and a
(Continued)

(51) Int. Cl.
*A61M 15/00* (2006.01)
*A61M 16/00* (2006.01)
(Continued)

(52) U.S. Cl.
CPC ............ *A61M 15/02* (2013.01); *A61B 5/411* (2013.01); *A61D 7/04* (2013.01); *A61M 15/08* (2013.01); *G06F 19/3462* (2013.01); *A61B 5/08* (2013.01); *A61B 5/082* (2013.01); *A61M 15/009* (2013.01); *A61M 15/0028* (2013.01); *A61M 15/0065* (2013.01); *A61M 2205/3553* (2013.01); *A61M 2205/3569* (2013.01);
(Continued)

(58) Field of Classification Search
USPC ............ 128/200.24, 200.14, 200.23, 203.12, 128/203.15, 204.21, 206.27, 206.21, 128/205.25
See application file for complete search history.

(56) References Cited

U.S. PATENT DOCUMENTS 4,068,624 A 1/1978 Ramney
4,265,236 A 5/1981 Pacella
(Continued)

FOREIGN PATENT DOCUMENTS

GB 2355627 A 4/2001
WO WO 2006/048417 A1 5/2006

OTHER PUBLICATIONS

Carrie R. Foote, Veterinary Products Laboratories Introduces First Ever Dog Appeasing Pheromone Collar, Veterinary Products Laboratories, May 4, 2006, printed Aug. 26, 2009 from http://www.vpl.com/press/view_press.php?id=100690, Published in: US.

*Primary Examiner* — Kristen Matter
(74) *Attorney, Agent, or Firm* — Suiter Swantz pc llo

(57) ABSTRACT

A method may include dispensing a dose of an inhalable compound according to a dosing instruction set; and maintaining a hands-free article for dispensing the inhalable compound in an operable dispensing position.

21 Claims, 73 Drawing Sheets

Related U.S. Application Data continuation-in-part of application No. 12/319,143, filed on Dec. 31, 2008, and a continuation-in-part of application No. 12/378,284, filed on Feb. 12, 2009, now abandoned, and a continuation-in-part of application No. 12/378,485, filed on Feb. 13, 2009, now Pat. No. 8,725,529, and a continuation-in-part of application No. 12/380,013, filed on Feb. 20, 2009, now abandoned, and a continuation-in-part of application No. 12/380,108, filed on Feb. 23, 2009, now abandoned, and a continuation-in-part of application No. 12/380,587, filed on Feb. 27, 2009, now abandoned, and a continuation-in-part of application No. 12/380,679, filed on Mar. 2, 2009, now abandoned, and a continuation-in-part of application No. 12/383,509, filed on Mar. 25, 2009, now Pat. No. 8,706,518, and a continuation-in-part of application No. 12/383,819, filed on Mar. 26, 2009, and a continuation-in-part of application No. 12/384,104, filed on Mar. 31, 2009, and a continuation-in-part of application No. 12/384,203, filed on Apr. 1, 2009, now Pat. No. 8,694,330, and a continuation-in-part of application No. 12/386,574, filed on Apr. 20, 2009, and a continuation-in-part of application No. 12/386,669, filed on Apr. 21, 2009, now Pat. No. 8,738,395, and a continuation-in-part of application No. 12/387,057, filed on Apr. 27, 2009, now Pat. No. 8,712,794, and a continuation-in-part of application No. 12/387,151, filed on Apr. 28, 2009, and a continuation-in-part of application No. 12/387,321, filed on Apr. 30, 2009, now abandoned, and a continuation-in-part of application No. 12/387,472, filed on May 1, 2009.

(51) Int. Cl.

| | | |
|---|---|---|
| B05D 7/14 | (2006.01) | |
| B65D 83/06 | (2006.01) | |
| A61M 15/02 | (2006.01) | |
| A61B 5/00 | (2006.01) | |
| A61D 7/04 | (2006.01) | |
| A61M 15/08 | (2006.01) | |
| G06F 19/00 | (2011.01) | |
| A61B 5/08 | (2006.01) | |

(52) U.S. Cl.
CPC ............. *A61M 2205/3584* (2013.01); *A61M 2205/3592* (2013.01); *A61M 2205/581* (2013.01); *A61M 2205/582* (2013.01); *A61M 2205/583* (2013.01); *A61M 2205/588* (2013.01); *A61M 2209/088* (2013.01); *A61M 2230/201* (2013.01); *A61M 2230/205* (2013.01)

(56) References Cited

U.S. PATENT DOCUMENTS

| | | |
|---|---|---|
| 4,456,007 A | 6/1984 | Nakao et al. |
| 4,652,261 A | 3/1987 | Mech et al. |
| 4,784,162 A | 11/1988 | Ricks et al. |
| 5,071,704 A | 12/1991 | Fischel-Ghodsian |
| 5,455,043 A | 10/1995 | Fischel-Ghodsian |
| 5,458,853 A | 10/1995 | Porter et al. |
| 5,487,378 A | 1/1996 | Robertson et al. |
| 5,546,943 A | 8/1996 | Gould |
| 5,610,674 A | 3/1997 | Martin |
| 5,709,863 A | 1/1998 | Pageat |
| 5,725,472 A | 3/1998 | Weathers |
| 5,807,114 A | 9/1998 | Hodges et al. |
| 5,819,207 A | 10/1998 | Takagi |
| 5,842,467 A | 12/1998 | Greco |
| 5,949,522 A | 9/1999 | Manne |
| 5,954,641 A | 9/1999 | Kehr et al. |
| 6,026,807 A | 2/2000 | Puderbaugh et al. |
| 6,052,114 A | 4/2000 | Morifuji |
| 6,077,867 A | 6/2000 | Pageat |
| 6,135,928 A | 10/2000 | Butterfield |
| 6,168,562 B1 | 1/2001 | Miller et al. |
| 6,169,113 B1 | 1/2001 | Pageat |
| 6,223,744 B1 * | 5/2001 | Garon ................. 128/200.14 |
| 6,280,383 B1 | 8/2001 | Damadian |
| 6,397,837 B1 | 6/2002 | Ferris |
| 6,425,764 B1 | 7/2002 | Lamson |
| 6,431,171 B1 | 8/2002 | Burton |
| 6,443,153 B1 | 9/2002 | Viljanen et al. |
| 6,513,523 B1 | 2/2003 | Izuchukwu et al. |
| 6,585,519 B1 | 7/2003 | Jenkins et al. |
| 6,609,068 B2 | 8/2003 | Cranley et al. |
| 6,663,888 B2 | 12/2003 | Percel et al. |
| 6,684,880 B2 | 2/2004 | Trueba |
| 6,702,767 B1 | 3/2004 | Douglas et al. |
| 6,780,171 B2 | 8/2004 | Gabel et al. |
| 6,889,687 B1 | 5/2005 | Olsson |
| 6,978,212 B1 | 12/2005 | Sunshine |
| 6,981,502 B2 | 1/2006 | McCormick et al. |
| 7,044,911 B2 | 5/2006 | Drinan et al. |
| 7,198,044 B2 | 4/2007 | Trueba |
| 7,353,065 B2 | 4/2008 | Morrell |
| 7,373,377 B2 | 5/2008 | Altieri |
| 7,383,837 B2 | 6/2008 | Robertson et al. |
| 7,427,417 B2 | 9/2008 | Jendrucko et al. |
| 7,447,541 B2 | 11/2008 | Huiku et al. |
| 7,711,583 B2 | 5/2010 | Epstein et al. |
| 7,720,696 B1 | 5/2010 | Berger et al. |
| 7,780,981 B2 | 8/2010 | DiPierro et al. |
| 8,068,983 B2 | 11/2011 | Vian et al. |
| 2001/0006939 A1 | 7/2001 | Niven et al. |
| 2001/0034023 A1 | 10/2001 | Stanton, Jr. et al. |
| 2001/0043664 A1 | 11/2001 | Grant |
| 2002/0084996 A1 | 7/2002 | Temkin et al. |
| 2003/0036683 A1 | 2/2003 | Kehr et al. |
| 2003/0113374 A1 | 6/2003 | Percel et al. |
| 2003/0114475 A1 | 6/2003 | Fox et al. |
| 2003/0221687 A1 | 12/2003 | Kaigler |
| 2004/0107961 A1 | 6/2004 | Trueba |
| 2004/0116784 A1 | 6/2004 | Gavish |
| 2004/0131682 A1 | 7/2004 | Percel et al. |
| 2004/0197271 A1 | 10/2004 | Kunka et al. |
| 2004/0254501 A1 | 12/2004 | Mault |
| 2005/0019734 A1 | 1/2005 | Peled |
| 2005/0054942 A1 | 3/2005 | Melker et al. |
| 2005/0115561 A1 | 6/2005 | Stahmann et al. |
| 2005/0154290 A1 | 7/2005 | Langleben |
| 2005/0220843 A1 | 10/2005 | DeWitt et al. |
| 2005/0228245 A1 | 10/2005 | Quy |
| 2005/0228691 A1 | 10/2005 | Paparo |
| 2005/0234742 A1 | 10/2005 | Hodgdon |
| 2005/0263150 A1 | 12/2005 | Chathampally et al. |
| 2006/0031099 A1 | 2/2006 | Vitello et al. |
| 2006/0085230 A1 | 4/2006 | Brill et al. |
| 2006/0129432 A1 | 6/2006 | Choi et al. |
| 2006/0207596 A1 | 9/2006 | Lane |
| 2007/0009555 A1 | 1/2007 | Borodic |
| 2007/0016265 A1 | 1/2007 | Davoodi et al. |
| 2007/0023044 A1 | 2/2007 | Kwok et al. |
| 2007/0054028 A1 | 3/2007 | Perlman et al. |
| 2007/0068514 A1 * | 3/2007 | Giroux ................. 128/200.14 |
| 2007/0068515 A1 | 3/2007 | Churchill |
| 2007/0124175 A1 | 5/2007 | Jung et al. |
| 2007/0191815 A1 | 8/2007 | DiPierro |
| 2007/0255115 A1 | 11/2007 | Anglin, Jr. et al. |
| 2008/0004540 A1 | 1/2008 | Nakao et al. |
| 2008/0014566 A1 | 1/2008 | Chapman et al. |
| 2008/0038701 A1 | 2/2008 | Booth et al. |
| 2008/0066739 A1 | 3/2008 | LeMahieu et al. |
| 2008/0087279 A1 | 4/2008 | Tieck et al. |
| 2008/0097167 A1 | 4/2008 | Yudkovitch et al. |
| 2008/0142010 A1 * | 6/2008 | Weaver et al. ........ 128/203.26 |
| 2008/0209289 A1 | 8/2008 | Farnsworth et al. |

(56) References Cited

U.S. PATENT DOCUMENTS

| | | |
|---|---|---|
| 2008/0214903 A1 | 9/2008 | Orbach |
| 2008/0230057 A1 | 9/2008 | Sutherland |
| 2008/0281639 A1 | 11/2008 | Quinn et al. |
| 2008/0317846 A1 | 12/2008 | Percel et al. |
| 2008/0318913 A1 | 12/2008 | Fox et al. |
| 2009/0046140 A1 | 2/2009 | Lashmet et al. |
| 2009/0111749 A1 | 4/2009 | Richardson et al. |
| 2009/0171259 A1 | 7/2009 | Soerensen et al. |
| 2009/0223249 A1 | 9/2009 | Julkowski et al. |
| 2009/0306741 A1 | 12/2009 | Hogle et al. |
| 2010/0062403 A1 | 3/2010 | Williams et al. |
| 2010/0178316 A1 | 7/2010 | Chauhan et al. |
| 2011/0226242 A1 | 9/2011 | Von Hollen et al. |

\* cited by examiner

```
                               ┌─ 200
        ╭───────╮            ↙
        │ Start │
        ╰───────╯
```

210
dispensing for inhalation by a user a dose of an inhalable compound according to a dosing instruction set

| 702 administering the inhalable compound via spraying a compound | 704 administering the inhalable compound via at least one of dusting or powderizing a compound | 706 administering the inhalable compound via nebulizing a compound | 708 administering the inhalable compound via vaporizing a compound |

220
maintaining in physical association with the user a hands free article for dispensing the inhalable compound in an operable dispensing position

```
        ╭───────╮
        │  End  │
        ╰───────╯
```

FIG. 7

```
                    Start        ← 5900

5910
dispensing for inhalation by a user a dose of an inhalable compound according to a
dosing instruction set 5920
maintaining in physical association with the user a hands free article for dispensing
the inhalable compound in an operable dispensing position 5930
supporting a hands free aerosol delivery system on the body of a mammal 2702
    disposing the hands free aerosol delivery system substantially around a
    portion of the body of a mammal 2704                                    2706
        encircling a neck portion of the        encircling a wrist portion of the
        body of a mammal with a support         body of a mammal with a support
        member of the hands free aerosol        member of the hands free aerosol
        delivery device                         delivery device End
```

Start

5910
dispensing for inhalation by a user a dose of an inhalable compound according to a dosing instruction set

5920
maintaining in physical association with the user a hands free article for dispensing the inhalable compound in an operable dispensing position

5930
supporting a hands free aerosol delivery system on the body of a mammal

2702
disposing the hands free aerosol delivery system substantially around a portion of the body of a mammal

2802
encircling a chest portion of the body of a mammal with a support member of the hands free aerosol delivery device

2804
encircling a head portion of the body of a mammal with a support member of the hands free hands free aerosol delivery device End

FIG. 28

```
                    ┌─────────┐
                    │  Start  │         ⤹ 5900
                    └────┬────┘
┌────────────────────────┴──────────────────────────────────────────┐
│ 5910                                                              │
│ dispensing for inhalation by a user a dose of an inhalable        │
│ compound according to a dosing instruction set                    │
└────────────────────────┬──────────────────────────────────────────┘
┌────────────────────────┴──────────────────────────────────────────┐
│ 5920                                                              │
│ maintaining in physical association with the user a hands free    │
│ article for dispensing the inhalable compound in an operable      │
│ dispensing position                                               │
└────────────────────────┬──────────────────────────────────────────┘
┌────────────────────────┴──────────────────────────────────────────┐
│ 5930                                                              │
│ supporting a hands free aerosol delivery system on the body of    │
│ a mammal                                                          │
│  ┌──────────────────────────────────────────────────────────────┐ │
│  │ 2702                                                         │ │
│  │ disposing the hands free aerosol delivery system             │ │
│  │ substantially around a portion of the body of a mammal       │ │
│  │  ┌─────────────────────────────────────────────────────────┐ │ │
│  │  │ 2902                                                    │ │ │
│  │  │ connecting a first end of a support member of a hands   │ │ │
│  │  │ free aerosol delivery device to a second end of a       │ │ │
│  │  │ support member of a hands free aerosol delivery device  │ │ │
│  │  │ while creating a circle about the body part of a mammal │ │ │
│  │  │  ┌────────────────────────────────────────────────────┐ │ │ │
│  │  │  │ 2904                                               │ │ │ │
│  │  │  │ connecting the first end of a support member of the│ │ │ │
│  │  │  │ hands free aerosol delivery device to the second   │ │ │ │
│  │  │  │ end of a support member of the hands free aerosol  │ │ │ │
│  │  │  │ delivery device via a magnet                       │ │ │ │
│  │  │  └────────────────────────────────────────────────────┘ │ │ │
│  │  └─────────────────────────────────────────────────────────┘ │ │
│  └──────────────────────────────────────────────────────────────┘ │
└────────────────────────┬──────────────────────────────────────────┘
                    ┌────┴────┐
                    │   End   │
                    └─────────┘
```

FIG. 29

```
                              ┌─ 5900
         ( Start )        ↙
            │
┌───────────────────────────────────────────────────────────────┐
│ 5910                                                          │
│ dispensing for inhalation by a user a dose of an inhalable    │
│ compound according to a dosing instruction set                │
└───────────────────────────────────────────────────────────────┘
            │
┌───────────────────────────────────────────────────────────────┐
│ 5920                                                          │
│ maintaining in physical association with the user a hands     │
│ free article for dispensing the inhalable compound in an      │
│ operable dispensing position                                  │
└───────────────────────────────────────────────────────────────┘
            │
┌───────────────────────────────────────────────────────────────┐
│ 5930                                                          │
│ supporting a hands free aerosol delivery system on the body   │
│ of a mammal                                                   │
│  ┌──────────────────────────────────────────────────────────┐ │
│  │ 2702                                                     │ │
│  │ disposing the hands free aerosol delivery system         │ │
│  │ substantially around a portion of the body of a mammal   │ │
│  │  ┌─────────────────────────────────────────────────────┐ │ │
│  │  │ 2902                                                │ │ │
│  │  │ connecting a first end of a support member of a     │ │ │
│  │  │ hands free aerosol delivery device to a second end  │ │ │
│  │  │ of a support member of a hands free aerosol         │ │ │
│  │  │ delivery device while creating a circle about the   │ │ │
│  │  │ body part of a mammal                               │ │ │
│  │  │  ┌────────────────────────────────────────────────┐ │ │ │
│  │  │  │ 3002                                           │ │ │ │
│  │  │  │ connecting the first end of a support member   │ │ │ │
│  │  │  │ of the hands free aerosol delivery device to   │ │ │ │
│  │  │  │ the second end of a support member of the      │ │ │ │
│  │  │  │ hands free aerosol delivery device via a hook  │ │ │ │
│  │  │  └────────────────────────────────────────────────┘ │ │ │
│  │  └─────────────────────────────────────────────────────┘ │ │
│  └──────────────────────────────────────────────────────────┘ │
└───────────────────────────────────────────────────────────────┘
            │
          ( End )
                                          FIG. 30
```

```
                              Start                    5900

5910
dispensing for inhalation by a user a dose of an inhalable compound according to a
dosing instruction set 5920
maintaining in physical association with the user a hands free article for dispensing
the inhalable compound in an operable dispensing position 5930
supporting a hands free aerosol delivery system on the body of a mammal 2702
    disposing the hands free aerosol delivery system substantially around a
    portion of the body of a mammal 2902
        connecting a first end of a support member of a hands free aerosol
        delivery device to a second end of a support member of a hands free
        aerosol delivery device while creating a circle about the body part of a
        mammal 3202
            connecting the first end of a support member of the hands free
            aerosol delivery device to the second end of a support member of
            the hands free aerosol delivery device via a threaded connection End
                                                       FIG. 32
```

```
                           ┌───────┐
                           │ Start │  ← 5900
                           └───┬───┘
```

5910
dispensing for inhalation by a user a dose of an inhalable compound according to a dosing instruction set

5920
maintaining in physical association with the user a hands free article for dispensing the inhalable compound in an operable dispensing position

5930
supporting a hands free aerosol delivery system on the body of a mammal > 2702
> disposing the hands free aerosol delivery system substantially around a portion of the body of a mammal
>
> > 2902
> > connecting a first end of a support member of a hands free aerosol delivery device to a second end of a support member of a hands free aerosol delivery device while creating a circle about the body part of a mammal
> >
> > > 3302
> > > connecting the first end of a support member of the hands free aerosol delivery device to the second end of a support member of the hands free aerosol delivery device via a belt-like connection End

FIG. 33

```
                            ┌─ 4400
      ( Start )            ↙

┌─────────────────────────────────────────────────────────────────┐
  │ 210                                                             │
  │ dispensing for inhalation by a user a dose of an inhalable      │
  │ compound according to a dosing instruction set                  │
  └─────────────────────────────────────────────────────────────────┘

┌─────────────────────────────────────────────────────────────────┐
  │ 220                                                             │
  │ maintaining in physical association with the user a hands free  │
  │ article for dispensing the inhalable compound in an operable    │
  │ dispensing position                                             │
  └─────────────────────────────────────────────────────────────────┘

┌─────────────────────────────────────────────────────────────────┐
  │ 4410                                                            │
  │ transmitting a dispensing order to a dispensing module via a    │
  │ optical transmission                                            │
  └─────────────────────────────────────────────────────────────────┘

( End )
```

FIG. 44

```
                            Start                        ← 5400

│
  ┌───────────────────────────┴───────────────────────────────────────┐
  │ 210                                                                │
  │ dispensing for inhalation by a user a dose of an inhalable compound according to a │
  │ dosing instruction set                                             │
  └───────────────────────────┬───────────────────────────────────────┘
                              │
  ┌───────────────────────────┴───────────────────────────────────────┐
  │ 220                                                                │
  │ maintaining in physical association with the user a hands free article for dispensing │
  │ the inhalable compound in an operable dispensing position          │
  └───────────────────────────┬───────────────────────────────────────┘
                              │
  ┌───────────────────────────┴───────────────────────────────────────┐
  │ 5410                                                               │
  │ dispensing a tracer compound in association with the inhalable compound │
  │  ┌──────────────────┐  ┌──────────────────┐  ┌──────────────────┐  │
  │  │ 5412             │  │ 5414             │  │ 5416             │  │
  │  │ dispensing a visual│ dispensing an olfactory│ dispensing a tastable│  │
  │  │ tracer compound  │  │ tracer compound  │  │ tracer compound  │  │
  │  └──────────────────┘  └──────────────────┘  └──────────────────┘  │
  └───────────────────────────┬───────────────────────────────────────┘
                              │
                            End
```

FIG. 54

```
                    Start                    5900

5910
dispensing for inhalation by a user a dose of an inhalable compound according to a
dosing instruction set 5920
maintaining in physical association with the user a hands free article for dispensing
the inhalable compound in an operable dispensing position 5930
supporting a hands free aerosol delivery system on the body of a mammal End
```

FIG. 59

METHOD FOR ADMINISTERING AN INHALABLE COMPOUND

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Dec. 30, 2008, application Ser. No. 12/317,934, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Dec. 31, 2008, application Ser. No. 12/319,143, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 12, 2009, application Ser. No. 12/378,284, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 13, 2009, application Ser. No. 12/378,485, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 20, 2009, application Ser. No. 12/380,013, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 23, 2009, application Ser. No. 12/380,108, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 27, 2009, application Ser. No. 12/380,587, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Mar. 2, 2009, application Ser. No. 12/380,679, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Mar. 25, 2009, application Ser. No. 12/383,509, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Mar. 26, 2009, application Ser. No. 12/383,819, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Mar. 31, 2009, application Ser. No. 12/384,104, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Apr. 1, 2009, application Ser. No. 12/384,203, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Apr. 20, 2009, application Ser. No. 12/386,574, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Apr. 21, 2009, application Ser. No. 12/386,669, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Apr. 27, 2009, application Ser. No. 12/387,057, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Apr. 28, 2009, application Ser. No. 12/387,151, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Apr. 30, 2009, application Ser. No. 12/387,321, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed May 1, 2009, application Ser. No. 12/387,472, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

In an aspect, a method includes, but is not limited to, dispensing a dose of an inhalable compound according to a dosing instruction set; and maintaining a hands-free article for dispensing an inhalable compound in an operable dispensing position. In addition to the foregoing, other method aspects are described in the claims, drawings, and text forming a part of the present disclosure.

In an aspect, a method includes, but is not limited to, dispensing a dose of an inhalable compound according to a dosing instruction set; maintaining a hands-free article for dispensing an inhalable compound in an operable dispensing position; and receiving a dose of an inhalable compound for dispensing. In addition to the foregoing, other method aspects are described in the claims, drawings, and text forming a part of the present disclosure.

In an aspect, a method includes dispensing a dose of an inhalable compound according to a dosing instruction set; maintaining a hands-free article for dispensing an inhalable compound in an operable dispensing position; and receiving the inhalable compound. In addition to the foregoing, other method aspects are described in the claims, drawings, and text forming a part of the present disclosure.

In an aspect, a method includes dispensing a dose of an inhalable compound according to a dosing instruction set; maintaining a hands-free article for dispensing an inhalable compound in an operable dispensing position; and supporting a hands-free aerosol delivery system on the body of a mammal. In addition to the foregoing, other method aspects are described in the claims, drawings, and text forming a part of the present disclosure.

In an aspect, a method includes detecting a medical condition parameter of a mammal according to a medical condition parameter request; maintaining a hands-free article for dispensing an inhalable compound in an operable dispensing position; and dispensing a dose of an inhalable compound according to a dosing instruction set. In addition to the foregoing, other method aspects are described in the claims, drawings, and text forming a part of the present disclosure.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 1A is a front elevation view illustrating a collar for dispensing one or more inhalable compounds.

FIG. 1B is a top plan view of a collar for dispensing one or more inhalable compounds.

FIG. 1C is a partial cross-sectional side elevation view of a collar for dispensing one or more inhalable compounds.

FIG. 1D is a partial cross-sectional side elevation view of a collar for dispensing one or more inhalable compounds.

FIG. 1E is a schematic of a collar for dispensing one or more inhalable compounds.

FIG. 1F is a schematic of a compound for being dispensed by a collar for dispensing one or more inhalable compounds.

FIG. 1G is a schematic of a compound for being dispensed by a collar for dispensing one or more inhalable compounds.

FIG. 1H is a schematic of a collar for dispensing one or more inhalable compounds, where the collar is connected to various storage media.

FIG. 2 illustrates an operational flow representing example operations related to maintaining a hands-free article for dispensing an inhalable compound according to a dosing instruction set, where the hands-free article is maintained in an operable dispensing position.

FIG. 3 illustrates an alternative embodiment of the operational flow of FIG. 2.

FIG. 4 illustrates an alternative embodiment of the operational flow of FIG. 2.

FIG. 5 illustrates an alternative embodiment of the operational flow of FIG. 2.

FIG. 6 illustrates an alternative embodiment of the operational flow of FIG. 2.

FIG. 7 illustrates an alternative embodiment of the operational flow of FIG. 2.

FIG. 8 illustrates an alternative embodiment of the operational flow of FIG. 56.

FIG. 9 illustrates an alternative embodiment of the operational flow of FIG. 56.

FIG. 10 illustrates an alternative embodiment of the operational flow of FIG. 56.

FIG. 11 illustrates an alternative embodiment of the operational flow of FIG. 56.

FIG. 12 illustrates an alternative embodiment of the operational flow of FIG. 56.

FIG. 13 illustrates an alternative embodiment of the operational flow of FIG. 56.

FIG. 14 illustrates an alternative embodiment of the operational flow of FIG. 56.

FIG. 15 illustrates an alternative embodiment of the operational flow of FIG. 56.

FIG. 16 illustrates an alternative embodiment of the operational flow of FIG. 56.

FIG. 17 illustrates an alternative embodiment of the operational flow of FIG. 57.

FIG. 18 illustrates an alternative embodiment of the operational flow of FIG. 57.

FIG. 19 illustrates an alternative embodiment of the operational flow of FIG. 57.

FIG. 20 illustrates an alternative embodiment of the operational flow of FIG. 57.

FIG. 21 illustrates an alternative embodiment of the operational flow of FIG. 57.

FIG. 22 illustrates an alternative embodiment of the operational flow of FIG. 57.

FIG. 23 illustrates an alternative embodiment of the operational flow of FIG. 57.

FIG. 24 illustrates an alternative embodiment of the operational flow of FIG. 57.

FIG. 25 illustrates an alternative embodiment of the operational flow of FIG. 57.

FIG. 26 illustrates an alternative embodiment of the operational flow of FIG. 57.

FIG. 27 illustrates an alternative embodiment of the operational flow of FIG. 59.

FIG. 28 illustrates an alternative embodiment of the operational flow of FIG. 59.

FIG. 29 illustrates an alternative embodiment of the operational flow of FIG. 59.

FIG. 30 illustrates an alternative embodiment of the operational flow of FIG. 59.

FIG. 32 illustrates an alternative embodiment of the operational flow of FIG. 59.

FIG. 33 illustrates an alternative embodiment of the operational flow of FIG. 59.

FIG. 44 illustrates an operational flow representing example operations related to maintaining a hands-free article for dispensing an inhalable compound according to a dosing instruction set, where the hands-free article is maintained in an operable dispensing position.

FIG. 54 illustrates an operational flow representing example operations related to maintaining a hands-free article for dispensing an inhalable compound according to a dosing instruction set, where the hands-free article is maintained in an operable dispensing position.

FIG. 59 illustrates an operational flow representing example operations related to maintaining a hands-free article for dispensing an inhalable compound according to a dosing instruction set, where the hands-free article is maintained in an operable dispensing position.

DETAILED DESCRIPTION

Figure 1A:
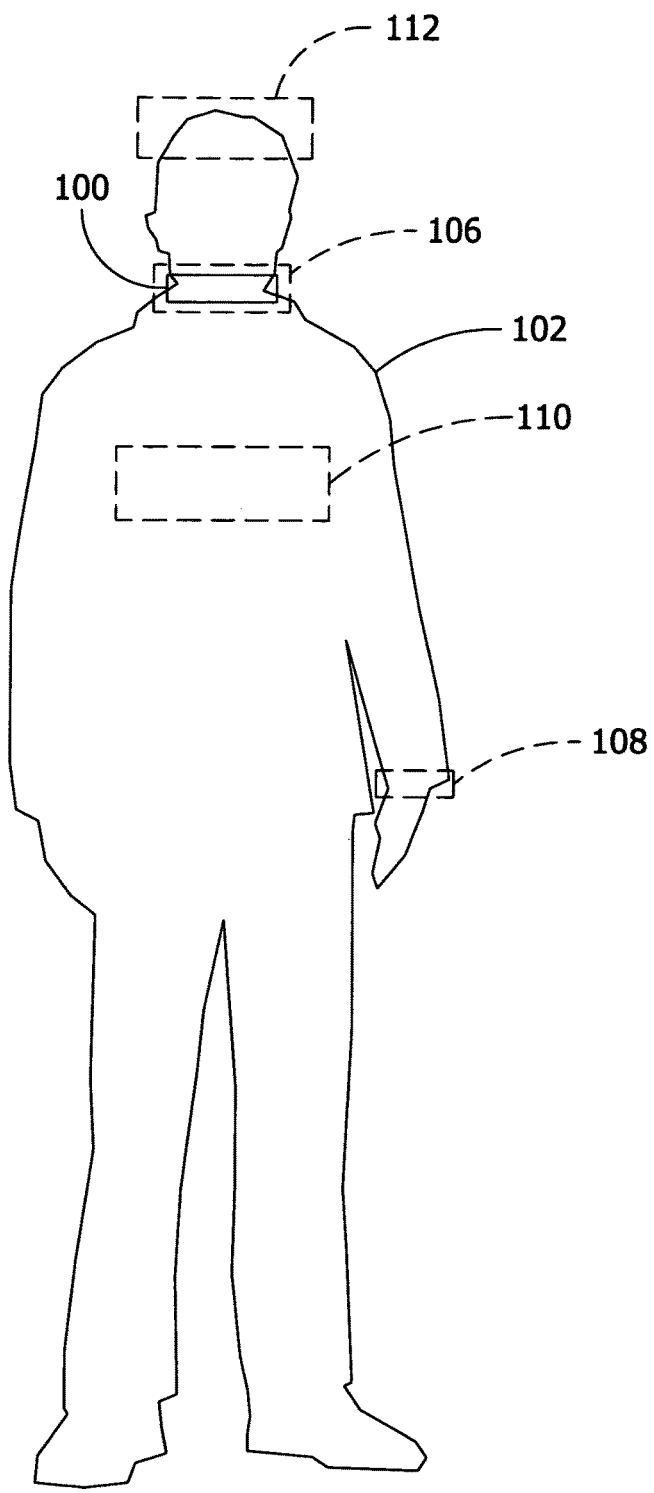
Figure 1B:
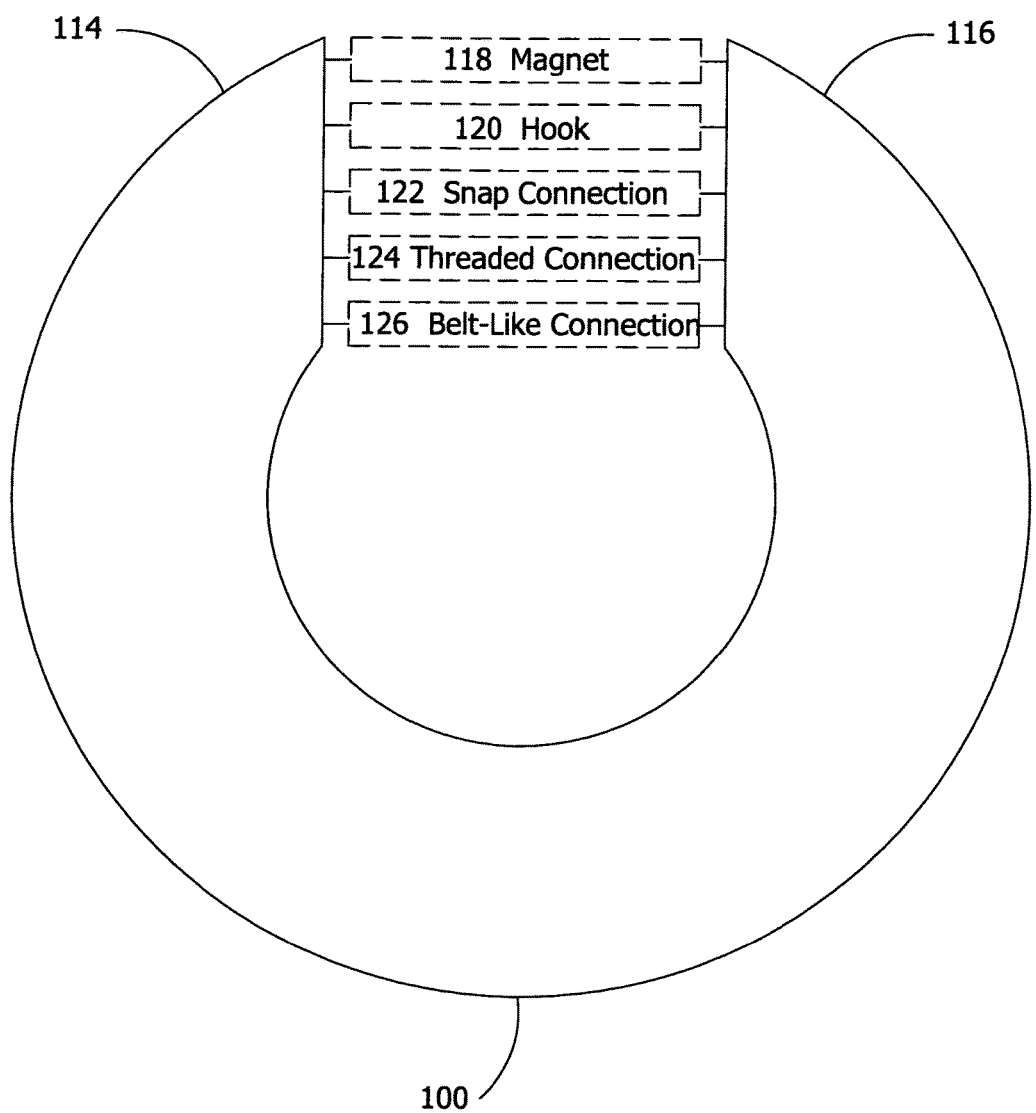
Figure 1C:
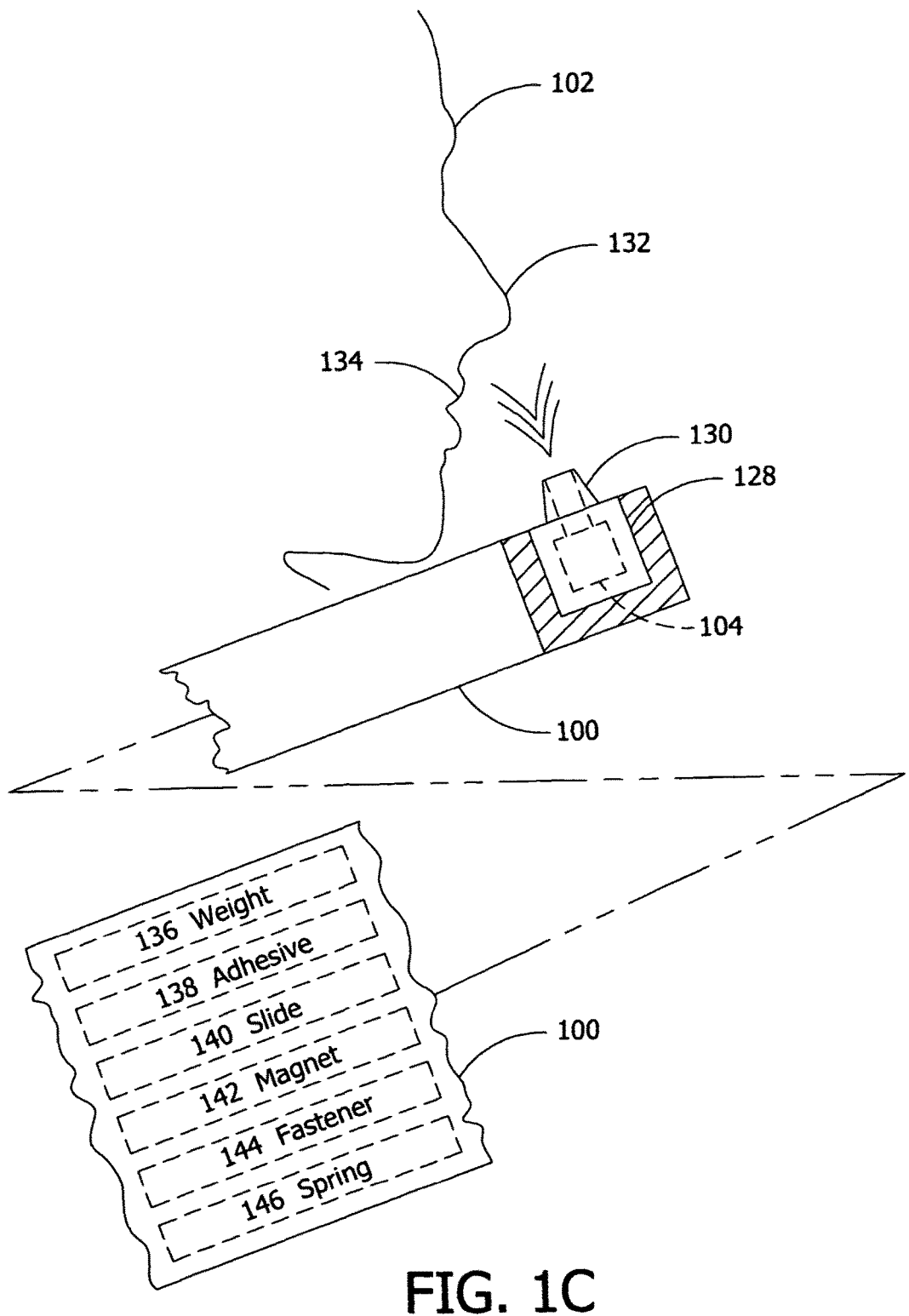
Figure 1D:
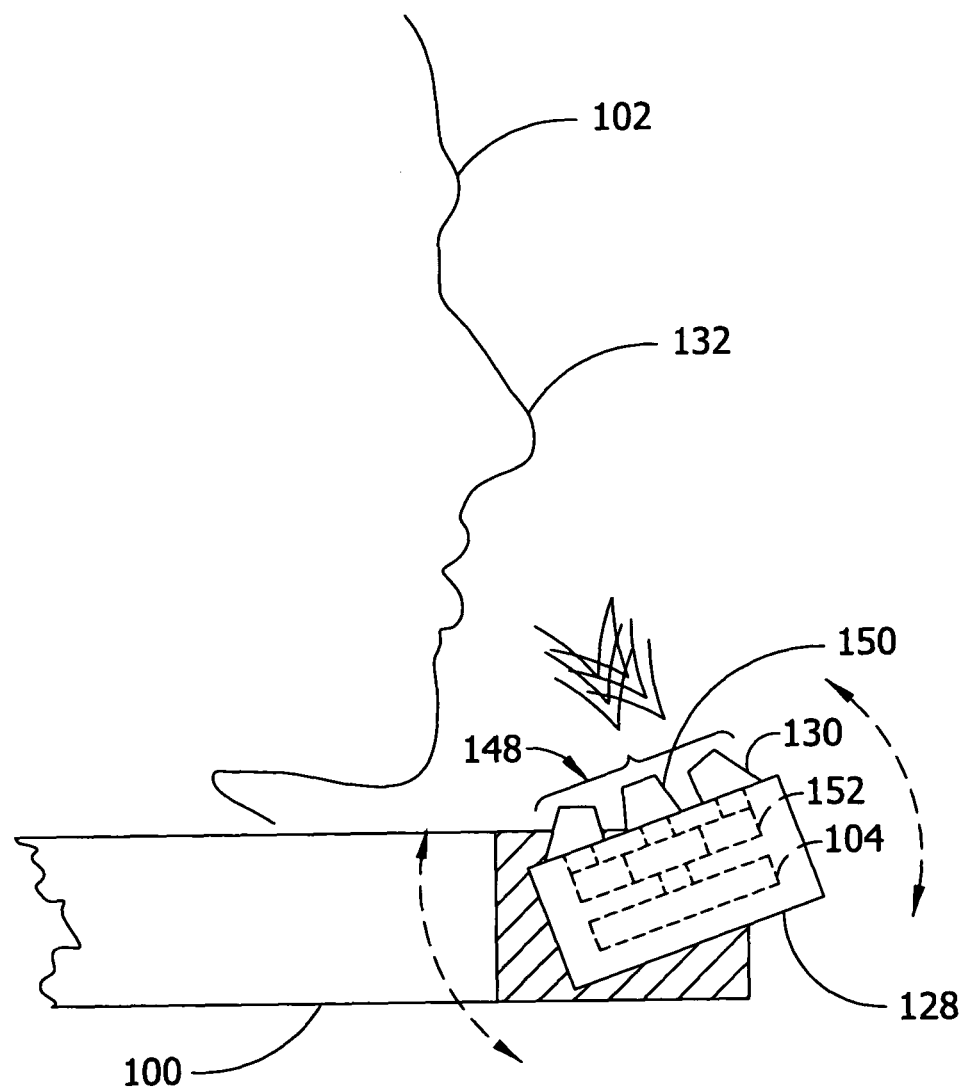
Figure 1E:
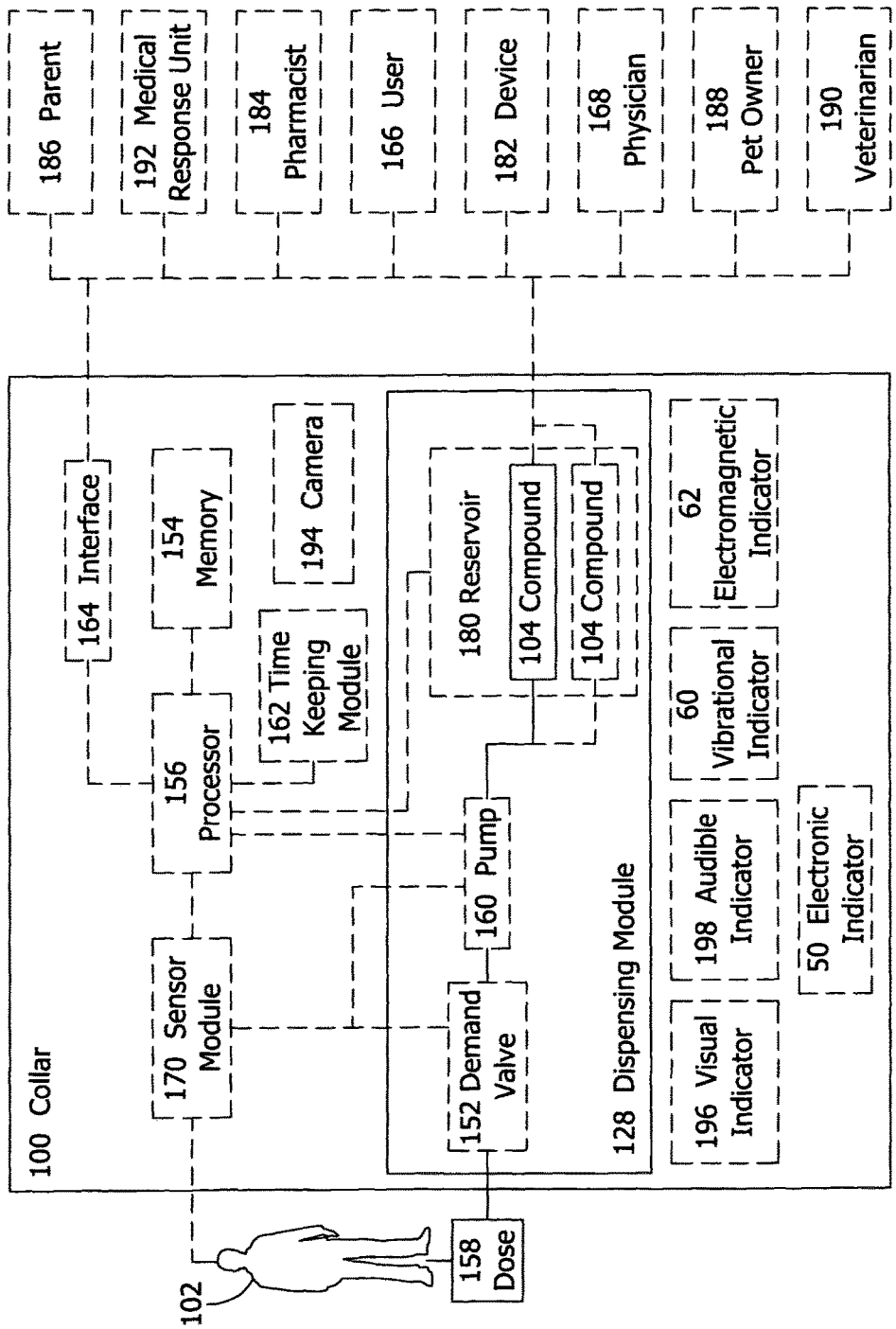
Figure 1H:
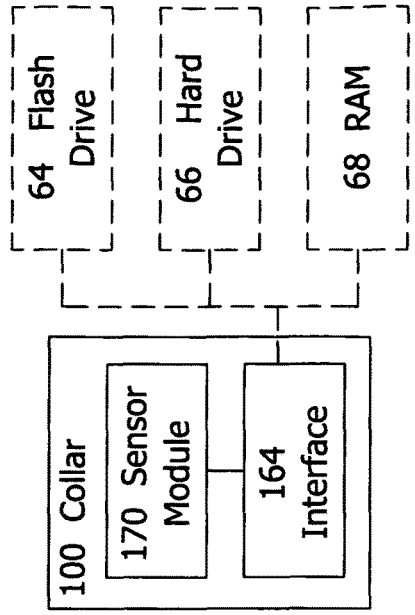
Figure 1G:
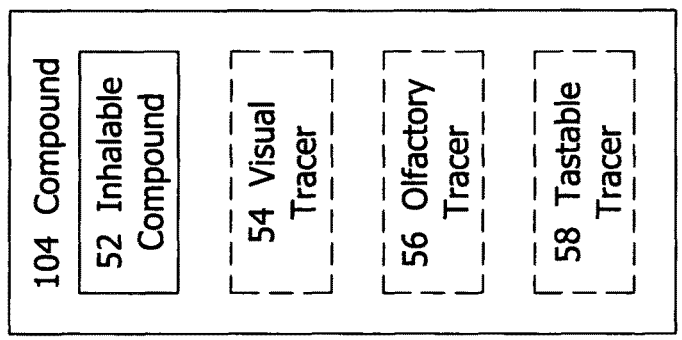
Figure 1F:
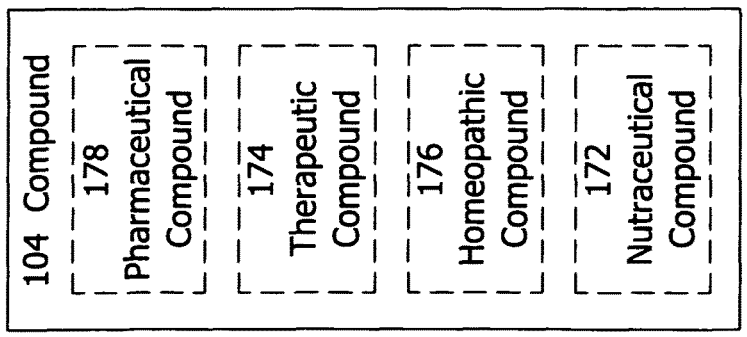

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring generally to FIGS. 1A through 1H, a hands-free article for dispensing one or more inhalable compounds is described in accordance with the present disclosure. The hands-free article, such as collar 100, may be worn by a subject 102 who can inhale a compound 104 dispensed by the collar 100. Although the subject 102 is depicted as a human in the accompanying figures, the subject can generally include any biological entity having respiratory organs (e.g., lungs), such as a mammalian entity (e.g., a human, a dog, a lion, or another mammal), an avian entity (e.g., a bird of prey or another avian), an amphibian entity (e.g., a frog or another amphibian), a reptilian entity (e.g., an alligator, a crocodile, a tortoise, or another reptile), as well as other biological entities having respiratory organs.

The collar 100 is maintained in an operable dispensing position. For example, the collar 100 may comprise a support for a hands-free aerosol delivery system on the body of a mammal. Thus, the collar 100 may be disposed around a portion of the body of the subject 102. For example, in one embodiment, the collar 100 may encircle a neck portion 106 of the subject 102. In an embodiment, the collar 100 may encircle a limb portion (e.g., wrist portion 108) of the subject 102. In an embodiment, the collar 100 may encircle a torso portion (e.g., chest portion 110) of the subject 102. In an embodiment, the collar 100 may encircle a head portion 112 of the subject 102. It should be noted that the above-mentioned embodiments are provided by way of example and are not meant to be limiting of the present disclosure. Thus, it is contemplated that the collar 100 may be maintained in an operable dispensing position by attaching it to a variety of other portions of the body of the subject 102.

The collar 100 may comprise a support member having a first end 114 and a second end 116. The first end 114 may be connected to the second end 116, encircling and creating a closed loop (e.g., a circle) about the body part of the subject 102. In an embodiment, the first end 114 may be connected to the second end 116 via a magnet 118. In an embodiment, the first end 114 of the collar 100 may be connected to the second end 116 of the collar 100 via a hook 120. In an embodiment, the first end 114 may be connected to the second end 116 via a snap connection 122. In an embodiment, the first end 114 of the collar 100 may be connected to the second end 116 of the collar 100 via a threaded connection 124. In an embodiment, the first end 114 may be connected to the second end 116 via a belt-like connection 126. It will be appreciated that this list of connections is provided by way of example and is not meant to be restrictive of the present disclosure. Other fastening devices may be utilized with the collar 100.

The collar 100 includes a dispensing module 128 for dispensing some amount of material, such as a dose (e.g., measured quantity, prescribed quantity, therapeutic quantity, etc.) of a compound 104 (e.g., organic compound, pharmaceutical compound, therapeutic compound, homeopathic compound, nutraceutical compound, biological material, protein, nucleic acid, cell, peptide, etc.) for modulating, curing, diagnosing, mitigating, preventing, or treating one or more of a disease, disorder, symptom or a condition. Additionally, the compound 104 may be utilized for enhancing one or more of a physical well-being or a mental well-being. The dispensing module 128 may be oriented in order to optimize delivery of the compound 104 to the subject 102. For example, in the case of an inhalable compound, the dispensing module may be oriented to optimize respiratory receipt by the subject 102. This may include orienting the dispensing module 128 such that an outlet (nozzle) 130 or jet emanating from the dispensing module 128 is pointed at (oriented towards) the nose 132 or mouth 134 of the subject 102.

Some inhalable compounds for utilization with the collar 100 may include, but are not limited to inhalable insulin, an inhalable corticosteroid, an inhalable antibiotic, an inhalable beta-2 agonist, or an inhalable mast cell stabilizer. Further, compounds for utilization with the collar 100 may include a compound that acts locally or systemically. Compounds for utilization with the collar 100 may include a compound having a formulation such that the formulation includes a carrier, such as a gas carrier, a liquid carrier, or a solid carrier. Additionally, compounds for utilization with the collar 100 may include a compound having a formulation such that the formulation includes penetration or absorption enhancers. It should be noted that this list is provided by way of example only and is not meant to be restrictive of the present invention. Further, it will be appreciated that various mechanisms or compounds may be utilized to power (e.g., nebulize) the inhalable compound out of the collar 100, such as $O_2$ (oxygen) or helium-$O_2$ (heliox). Such compounds may be selected for improving the response of the subject (e.g., heliox when utilized with an inhaled bronchodilator such as an inhalable beta-2 agonist).

Further, the dispensing module 128 may be maintained in an optimal position for optimizing delivery of the compound 104 to the subject 102. In an embodiment, a relative position or direction to a desired respiratory target is determined. For example, a direction to the subject's nose 132 may be determined. In an embodiment, a position of the dispensing module 128 may then be maintained for optimizing delivery of the compound 104. For example, the orientation of the outlet 130 may be maintained in the direction determined for the subject's nose 132. In an embodiment, the position of the dispensing module 128 may be maintained via a weight 136. In an embodiment, the position of the dispensing module may be maintained via an adhesive 138. In an embodiment, the position of the dispensing module 128 may be maintained via a slide 140. In an embodiment, the position of the dispensing module 128 may be maintained via a magnet 142. In an embodiment, the position of the dispensing module 128 may be maintained via a fastener 144 (e.g., a button or a snap). In an embodiment, the position of the dispensing module 128 may be maintained via a spring 146.

It will be appreciated that this list is provided by way of example and is not meant to be restrictive of the present disclosure.

The delivery of the compound 104 can be controlled to optimize or regulate delivery of the material 104 to the subject 102. The delivery mechanism can be one or more of the same type of material delivery system (e.g., nebulizer), or may include at least two different delivery systems (e.g., nebulizer and a dry powder inhaler), the at least one outlet 130 may be one of a suite or an array of outlets (e.g., nozzles) 148. One or more outlets (e.g., the first nozzle 130 and a second nozzle 150) may be selected to deliver the compound 104. In an embodiment, the first and second nozzles 130 and 150 may be in different locations. The direction of the subject's nose 132 may be determined. Then, a discharge direction for the dispensing module 128 can be controlled for optimizing delivery of the compound 104. For example, the orientation of the dispensing module 128 can be controlled to orient the first outlet 130 and the second outlet 150 in the direction determined for the subject's nose 132. In an embodiment, directed delivery of the compound 104 may be accomplished via a demand valve 152 coupled with programmable dosing. In an embodiment, directed delivery of the compound 104 may be accomplished via a charged particle dispersion. In an embodiment, the first outlet 130, the second outlet 150, or the suite of outlets 148 may include outlets having variable discharge characteristics, such as directional, volumetric, spray area, or other characteristics.

Various mechanical systems for delivering inhalable materials may include, but are not limited to, a vaporizer (e.g., a device for vaporizing liquid material for inhalation), a nebulizer (e.g., a device for administering material in the form of a mist for inhalation), a liquid aerosol system (e.g., a system for propelling fine droplets of material utilizing a gas), a dry powder inhalation system, an atomizer (e.g., a device for reducing a liquid material to a spray or vapor for inhalation), a metered dose inhaler (e.g., a device for releasing a metered dose of material for inhalation), a propellant-delivered system, a piezo-electric inhaler (e.g., an inhaler utilizing a piezo vibrator to deaggregate a material powder for subsequent inhalation by the subject), etc. It is further contemplated that the material 104 may be provided in removable or replaceable storage units. For example, the material 104 may be provided in an easily replaceable dose packet. In an embodiment, the material 104 may be provided in a removable canister. It will be appreciated that these storage units are provided by way of example, and other various storage configurations having varying shapes, sizes, and form factors may be utilized with the collar 100.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Figure 2:
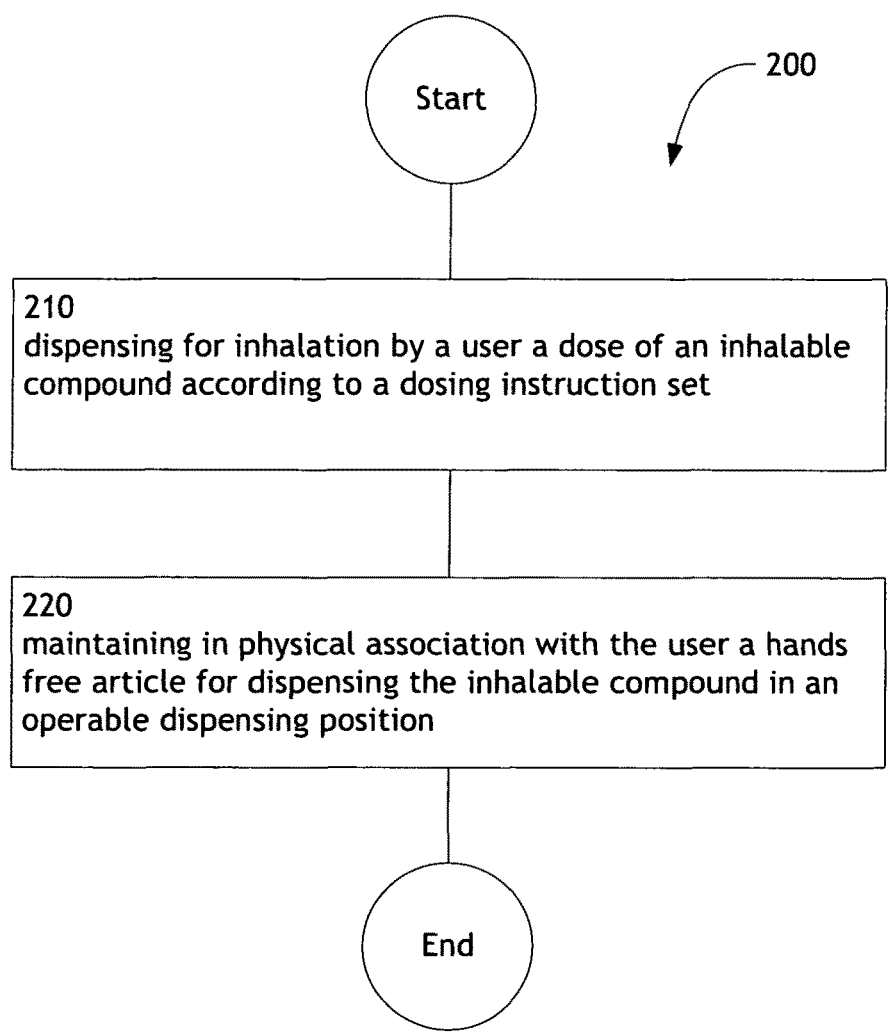

FIG. 2 illustrates an operational flow 200 representing example operations related to maintaining a hands-free article for dispensing an inhalable compound according to a dosing instruction set, where the hands-free article is maintained in an operable dispensing position. In FIG. 2 and in following figures that include various examples of operational flows, discussion and explanation may be provided with respect to the above-described examples of FIGS. 1A through 1H, and/or with respect to other examples and contexts. However, it should be understood that the operational flows may be executed in a number of other environments and contexts, and/or in modified versions of FIGS. 1A through 1H. Also, although the various operational flows are presented in the sequence(s) illustrated, it should be understood that the various operations may be performed in other orders than those which are illustrated, or may be performed concurrently.

After a start operation, the operational flow 200 moves to an operation 210. Operation 210 depicts dispensing for inhalation by a user a dose of an inhalable compound according to a dosing instruction set. For example, as shown in FIGS. 1A through 1H, the collar 100 may include a memory 154 for storing a dosing instruction set. The memory 154 may be connected to a processor 156 operatively configured for initiating the dispensing of a dose 158 of a compound 104. In an embodiment, the processor 156 is connected to a pump 160. The processor 156 may electronically signal the pump 160 to dispense the dose 158 of the compound 104.

Then, operation 220 depicts maintaining in physical association with the user a hands-free article for dispensing an inhalable compound in an operable dispensing position. For example, as shown in FIGS. 1A through 1H, the collar 100 may be maintained in an operable position by positioning a weight 136 at one end of the collar 100.

Figure 3:
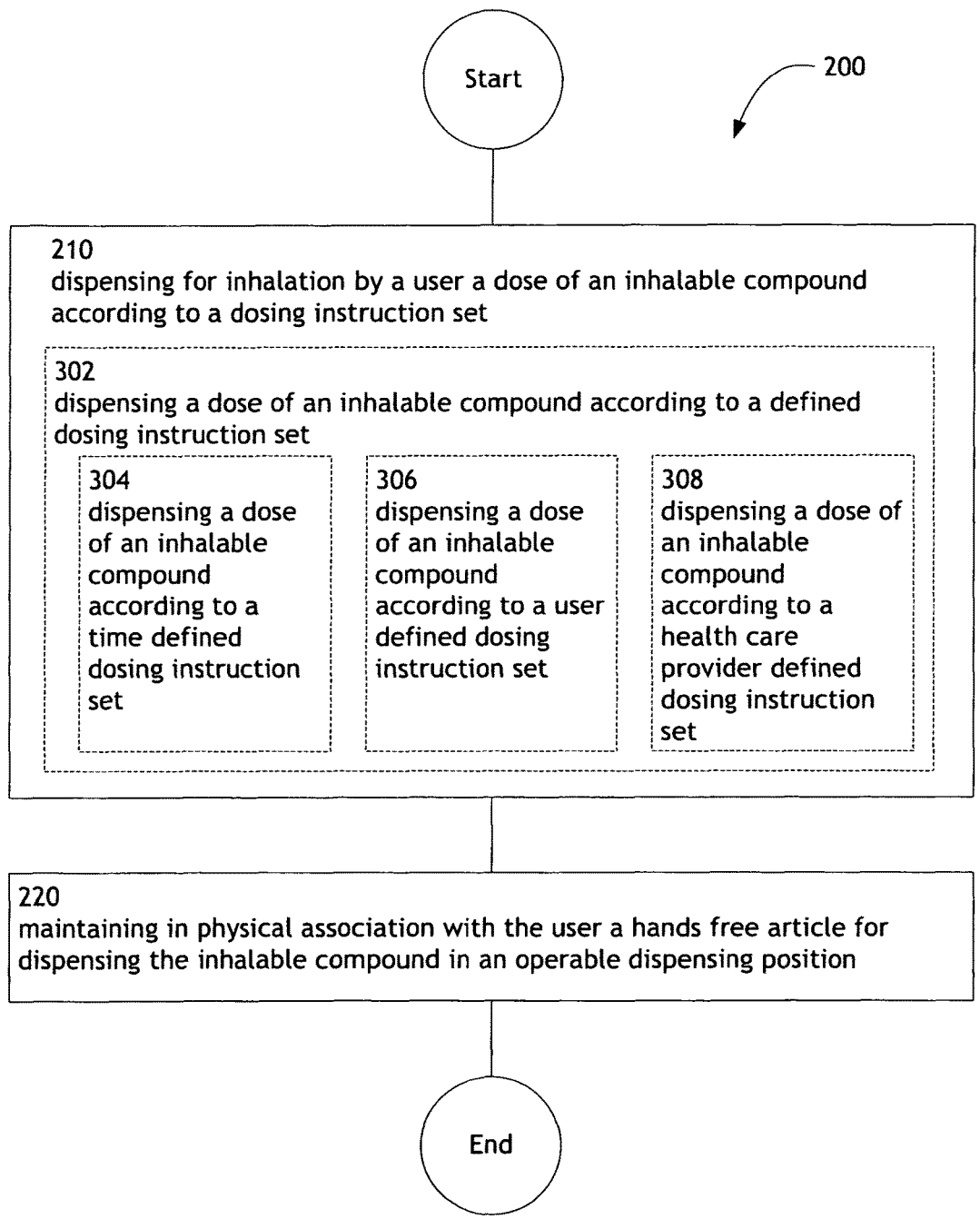

FIG. 3 illustrates alternative embodiments of the example operational flow 200 of FIG. 2. FIG. 3 illustrates example embodiments where the operation 210 may include at least one additional operation. Additional operations may include an operation 302, an operation 304, an operation 306, and/or an operation 308.

The operation 302 illustrates dispensing a dose of an inhalable compound according to a defined dosing instruction set. For example, as shown in FIGS. 1A through 1H, the memory 154 may store a defined dosing instruction set, and a processor 156 coupled with the memory 154 may be configured for initiating dispensing of the compound 104 according to the dosing instruction set. Further, the operation 304 illustrates dispensing a dose of an inhalable compound according to a time defined dosing instruction set. For example, as shown in FIGS. 1A through 1H, the memory 154 may store a time defined dosing instruction set, and the processor 156 coupled with the memory 154 may be configured for initiating dispensing of the compound 104 according to the time defined dosing instruction set. In an embodiment, the processor 156 is connected to a time keeping module 162 for determining when to dispense the compound 104. For example, the compound 104 may be dispensed while the subject 102 is sleeping (or is scheduled to sleep according to the time defined dosing instruction set). Alternatively, the compound 104 may be dispensed shortly before the subject is scheduled to sleep (e.g., in the case of a compound including a sleep aid, or the like). Further, the operation 306 illustrates dispensing a dose of an inhalable compound according to a user defined dosing instruction set. For example, as shown in FIGS. 1A through 1H, the memory 154 may store a user defined dosing instruction set, and the processor 156 coupled with the memory 154 may be configured for initiating dispensing of the compound 104 according to the user defined dosing instruction set. In an embodiment, the collar 100 may include an interface 164 accessible by a user 166 for supplying the user defined dosing instruction set to the memory 154 (e.g., via the processor 156). Further, the operation 308 illustrates dispensing a dose of an inhalable compound according to a health care provider-defined dosing instruction set. For example, as shown in FIGS. 1A through 1H, the collar 100 may include an interface 164 accessible by a physician 168 for supplying a physician defined dosing instruction set to the memory 154 (e.g., via the processor 156).

Figure 4:
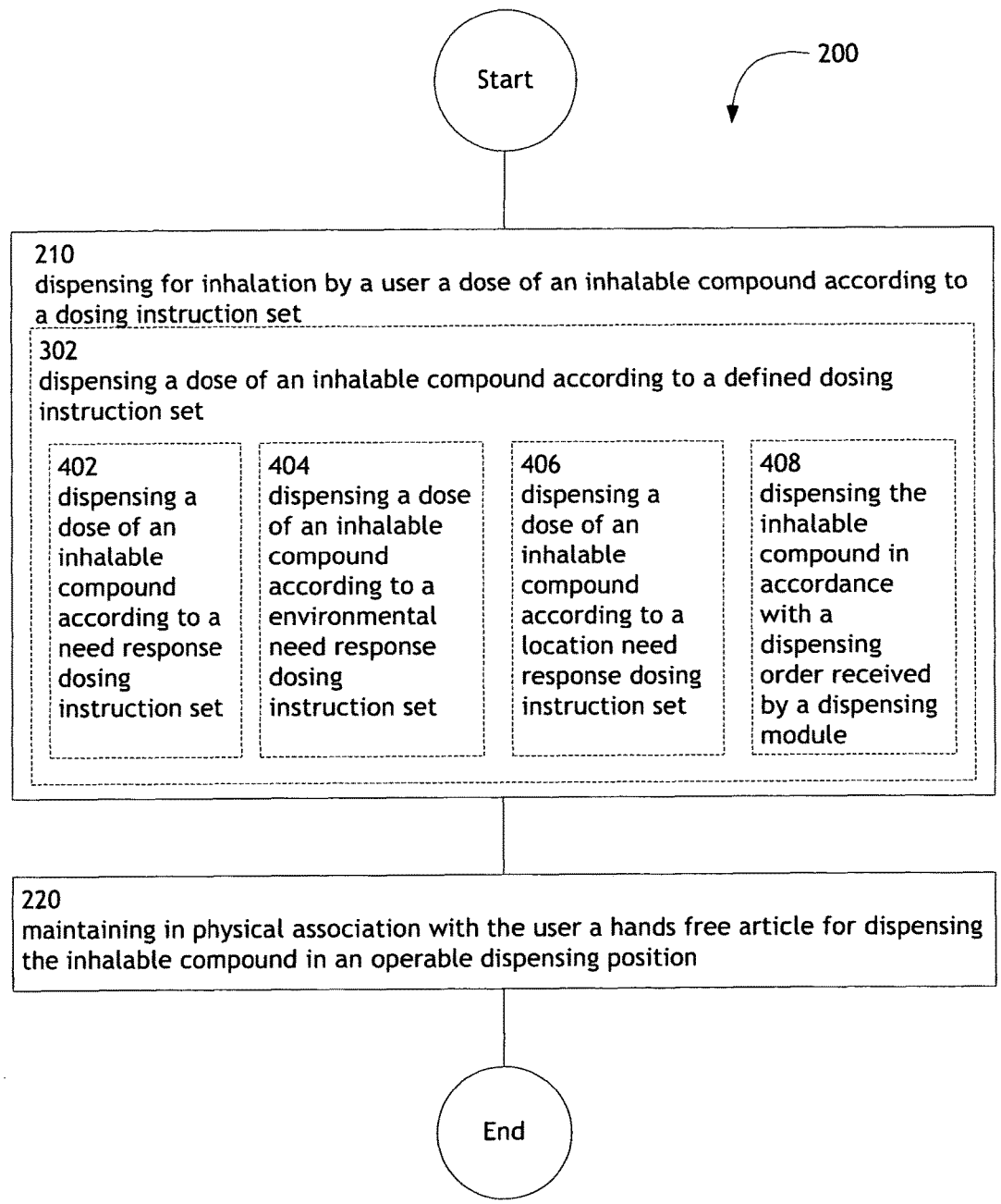

FIG. 4 illustrates alternative embodiments of the example operational flow 200 of FIG. 2. FIG. 4 illustrates example embodiments where the operation 210 may include at least one additional operation. Additional operations may include an operation 402, an operation 404, an operation 406, and/or an operation 408. Further, the operation 402 illustrates dispensing a dose of an inhalable compound according to a need response dosing instruction set. For example, as shown in FIGS. 1A through 1H, the collar 100 may include a memory 154 for storing a need response dosing instruction set. The collar 100 may also include a transducer (e.g., a sensor module 170) for sensing a health or wellness-related characteristic (or another characteristic) of the subject 102. Based on the sensed characteristic of the subject 102, the processor 156 may be operatively configured to dispense the dose 158 of the compound 104 after verifying that the characteristic corresponds to a need stored in the need response dosing instruction set. In one instance, a sensed characteristic includes a blood glucose level, and the need response dosing instruction set includes instructions for dispensing a dose of the compound when the sensed blood glucose level is above a certain threshold. Further, the operation 404 illustrates dispensing a dose of an inhalable compound according to an environmental need response dosing instruction set. For example, as shown in FIGS. 1A through 1H, the collar 100 may include a memory 154 for storing an environmental need response dosing instruction set. The collar 100 may also include a sensor module 170 for sensing an environment occupied by the subject 102. Based on the sensed environment of the subject 102, the processor 156 may be operatively configured to dispense the dose 158 of the compound 104 after verifying that the environment corresponds to an environment stored in the environmental need response dosing instruction set. In an embodiment, the sensed environment may include sensing an actual or Likely trigger (e.g., an allergen, a chemical, an irritant, or a particulate). A likely trigger may include, for example, a sensed environment where the presence of an animal increases a likelihood of dander, or an outside environment where a time of year (e.g., the month of May) increases a likelihood of pollen exposure. In one instance, a sensed environment includes an outdoor environment, and the environment need response dosing instruction set includes instructions for dispensing a dose of the compound when the outdoor environment is sensed. In an embodiment, the sensed environment includes at least one other individual (and possibly a number of other individuals, e.g., a crowd), and the environmental need response dosing instruction set includes instructions for dispensing a dose of a vaccine when the other individual is sensed. In an embodiment, the environmental need response dosing instruction set includes instructions for dispensing a dose of a calming agent or anti-anxiety medication when one or more other individuals are sensed. In an embodiment, the sensed environment does not include another individual, and the environmental need response dosing instruction set includes instructions for dispensing a dose of a vaccine when the absence of other individuals is sensed. Further, the operation 406 illustrates dispensing a dose of an inhalable compound according to a location need response dosing instruction set. For example, as shown in FIGS. 1A through 1H, the collar 100 may include a memory 154 for storing a location need response dosing instruction set. The collar 100 may also include a sensor module 170 for sensing a location occupied by the subject 102. Based on the sensed location of the subject 102, the processor 156 may be operatively configured to dispense the dose 158 of the compound 104 after verifying that the location corresponds to a location stored in the location need response dosing instruction set. In one instance, a sensed location includes a school zone, and the location need response dosing instruction set includes instructions for dispensing a dose of the compound when the school zone is sensed. In another instance, the sensed location includes a living space, and the location need response dosing instruction set includes instructions for dispensing a dosage of a pheromone (or another substance) for preventing a pet from urinating in the living space. Alternatively, the sensed location may include a litter box, and the dosing instruction set may include instructions for dispensing a pheromone (or another substance) for enticing a pet to defecate in the litter box. Further, the operation 408 illustrates dispensing the inhalable compound in accordance with a dispensing order received by a dispensing module. For example, as shown in FIGS. 1A through 1H, the dispensing module 128 may receive a dispensing order from the processor 156.

In an embodiment, the dispensing order may be dispatched upon the sensor module 170 detecting a condition of the subject, such as an asthmatic incident (e.g., a narrowing of the subject's airways). In an embodiment, the sensor module 170 may identify a symptom of an asthmatic incident, such as a subject experiencing trouble breathing, a sneeze, a cough, a wheeze, a rhonchus, or a snore. In an embodiment, the sensor module 170 may identify a physical condition associated with an asthmatic incident, such as a narrowing of the subject's airways. Other symptoms or conditions detected by the sensor module 170 may include, but are not limited to, Chronic Obstructive Pulmonary Disease (COPD), bronchitis, abnormally high blood glucose level, etc. Further, it will be appreciated that the processor 156 may determine the most effective route of administration for a material based upon a particular condition or set of symptoms. In an embodiment, the processor 156 may determine that an inhalation route of delivery including the nasal cavity is a most effective route of treatment for an asthmatic incident, and may instruct administration of the dose 158 of the material 104 accordingly (e.g., in a case where the dose 158 includes a beta-2 agonist.) In an embodiment, the processor 156 may be programmed to determine whether a to-be-delivered agent should be provided to the subject via intra-nasal administration or inhalation, or both. For example, for a desired delivery of an agent to the brain of the subject, the device may be programmed to administer such agent through intranasal administration.

Figure 5:
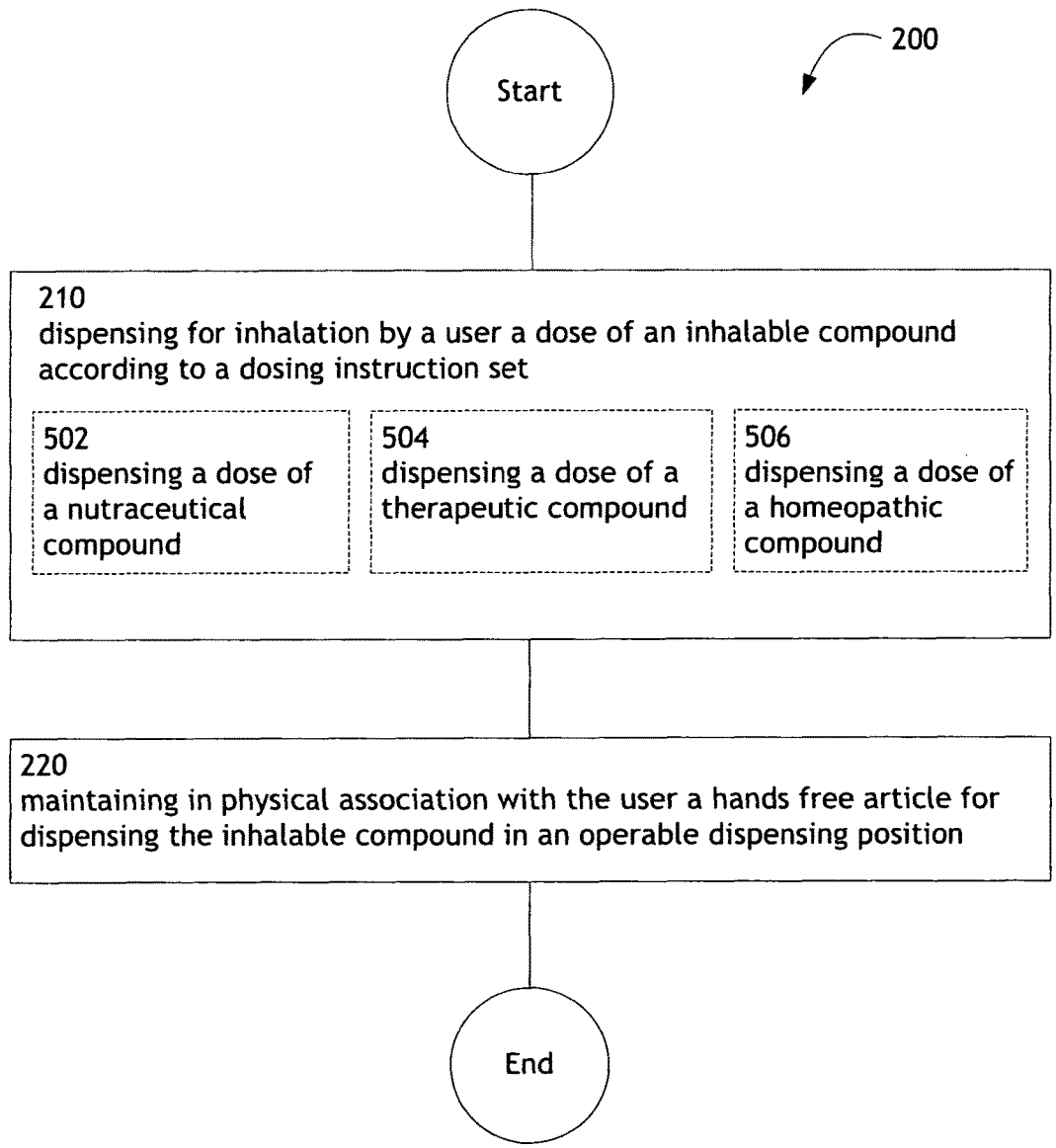

FIG. 5 illustrates alternative embodiments of the example operational flow 200 of FIG. 2. FIG. 5 illustrates example embodiments where the operation 210 may include at least one additional operation. Additional operations may include an operation 502, an operation 504, and/or an operation 506.

The operation 502 illustrates dispensing a dose of a nutraceutical compound. For example, as shown in FIGS. 1A through 1H, the compound 104 may include a nutraceutical compound 172.

The operation 504 illustrates dispensing a dose of a therapeutic compound. For example, as shown in FIGS. 1A through 1H, the compound 104 may include a therapeutic compound 174.

The operation 506 illustrates dispensing a dose of a homeopathic compound. For example, as shown in FIGS. 1A through 1H, the compound 104 may include a homeopathic compound 176.

Figure 6:
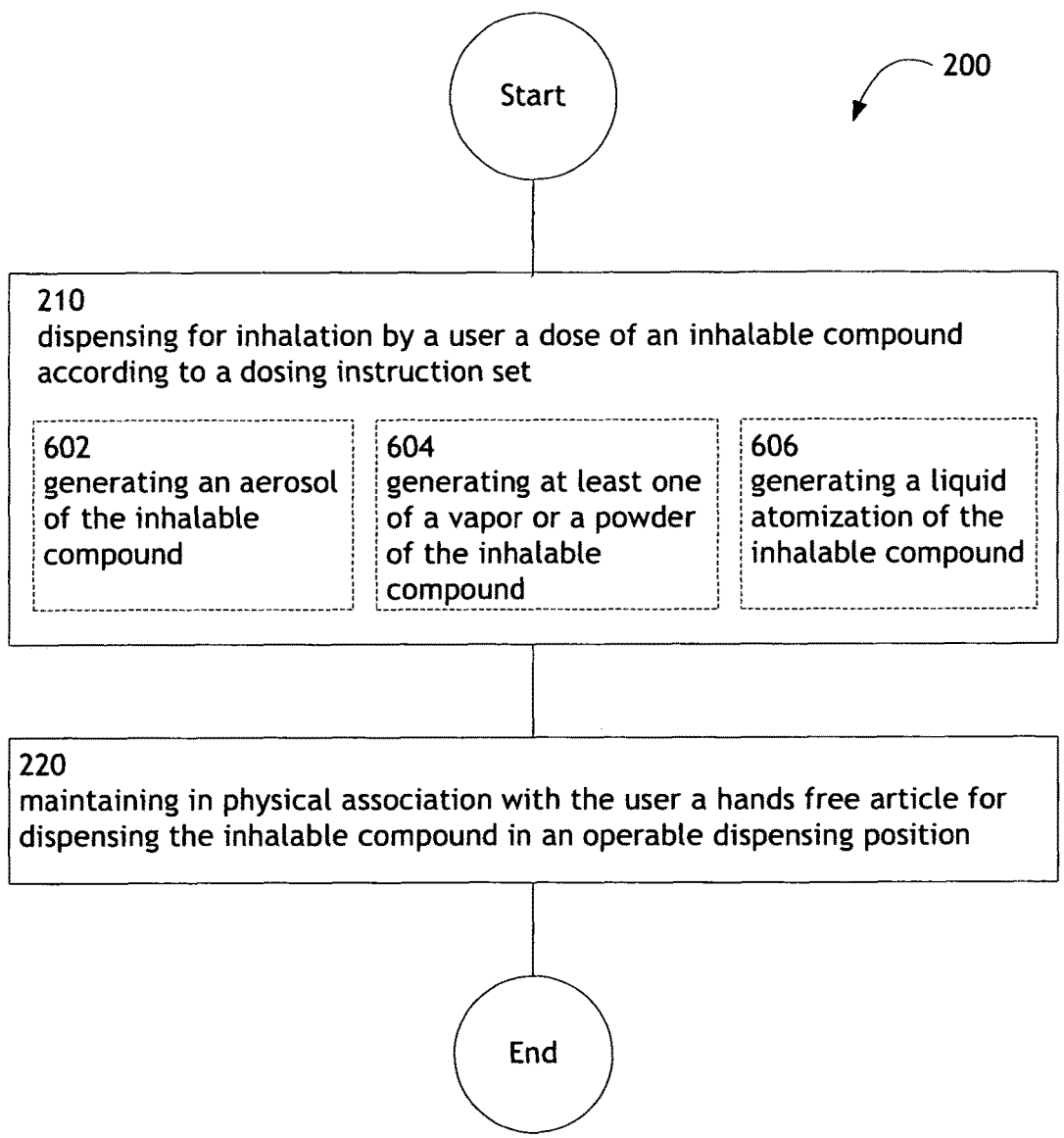

FIG. 6 illustrates alternative embodiments of the example operational flow 200 of FIG. 2. FIG. 6 illustrates example embodiments where the operation 210 may include at least one additional operation. Additional operations may include an operation 602, an operation 604, and/or an operation 606.

The operation 602 illustrates generating an aerosol of the inhalable compound. For example, as shown in FIGS. 1A through 1H, the compound 104 may include an aerosol which may be dispensed via the nozzle 130.

The operation 604 illustrates generating at least one of a vapor or a powder of the inhalable compound. For example, as shown in FIGS. 1A through 1H, the compound 104 may include a vapor which may be dispensed via the suite of nozzles 148. Alternatively, the compound 104 may include a powder, which may be dispensed via the suite of nozzles 148. Generating a powder may include, for example, generating particles, fine particles, micronized particles, microparticles, or particulates.

The operation 606 illustrates generating a liquid atomization of the inhalable compound. For example, as shown in FIGS. 1A through 1H, the compound 104 may include an atomized liquid which may be dispensed via the nozzle 130.

FIG. 7 illustrates alternative embodiments of the example operational flow 200 of FIG. 2. FIG. 7 illustrates example embodiments where the operation 210 may include at least one additional operation. Additional operations may include an operation 702, an operation 704, an operation 706, and/or an operation 708.

The operation 702 illustrates administering the inhalable compound via spraying a compound. For example, as shown in FIGS. 1A through 1H, the compound 104 may be sprayed via the nozzle 130.

The operation 704 illustrates administering the inhalable compound via at least one of dusting or powderizing a compound. For example, as shown in FIGS. 1A through 1H, the compound 104 may be dusted via the nozzle 130. Powderizing the compound may include, for example, de-agglomeration, or particularizing.

The operation 706 illustrates administering the inhalable compound via nebulizing a compound. For example, as shown in FIGS. 1A through 1H, the compound 104 may be nebulized and dispensed via the nozzle 130.

The operation 708 illustrates administering the inhalable compound via vaporizing a compound. For example, as shown in FIGS. 1A through 1H, the compound 104 may be vaporized and dispensed via the nozzle 130.

In an embodiment, the inhalable compound may include a carrier. For example, a carrier may include a gas carrier, a liquid carrier, or a solid carrier. In embodiments, the carrier may include a hydrocarbon, a fluorocarbon, a propellant, a salt, a saccharide, a lipid, a liposome, a synthetic, or a natural polymer. Further, various formulations including a carrier may include penetration or absorption enhancers.

Figure 8:
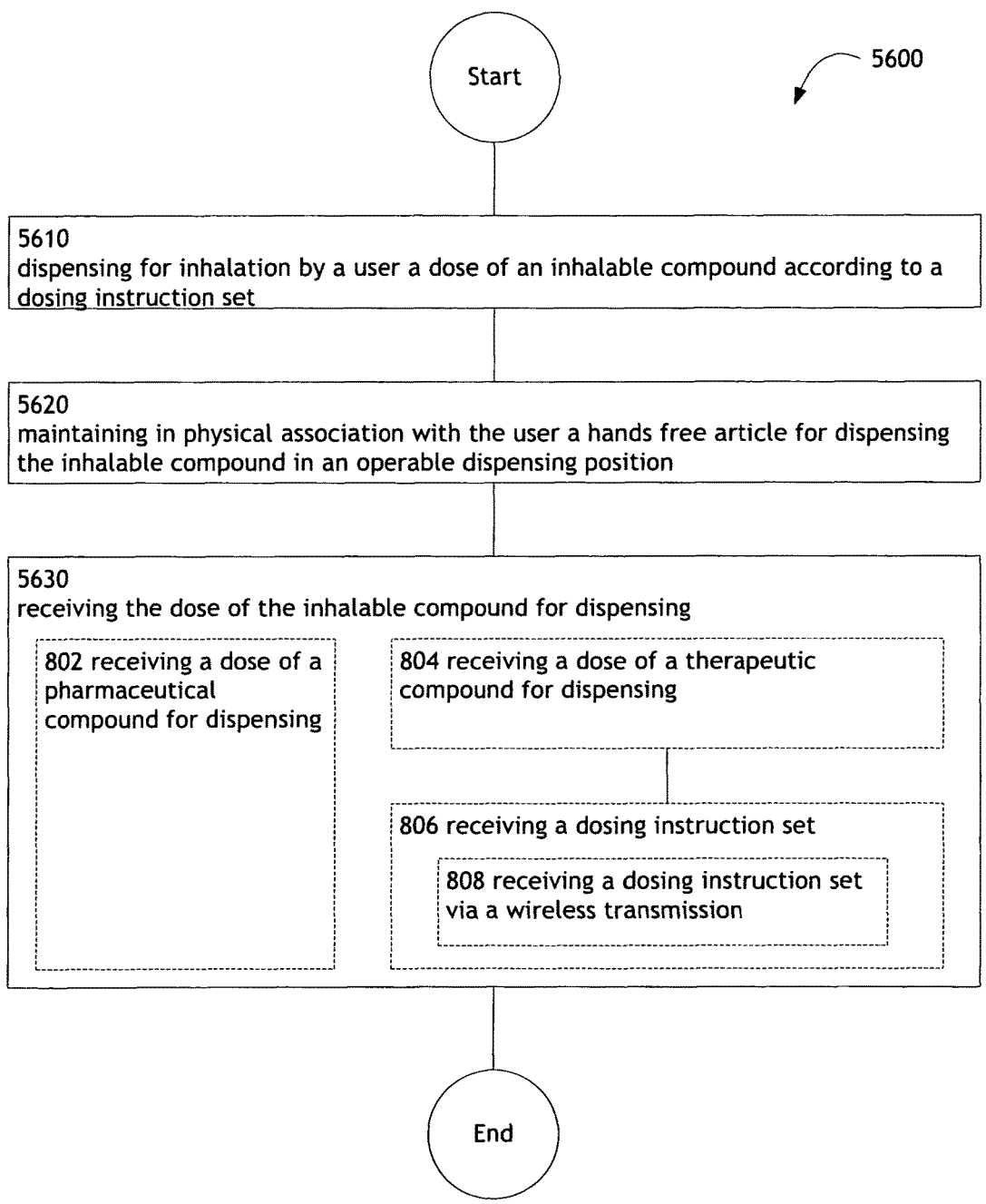
Figure 56:
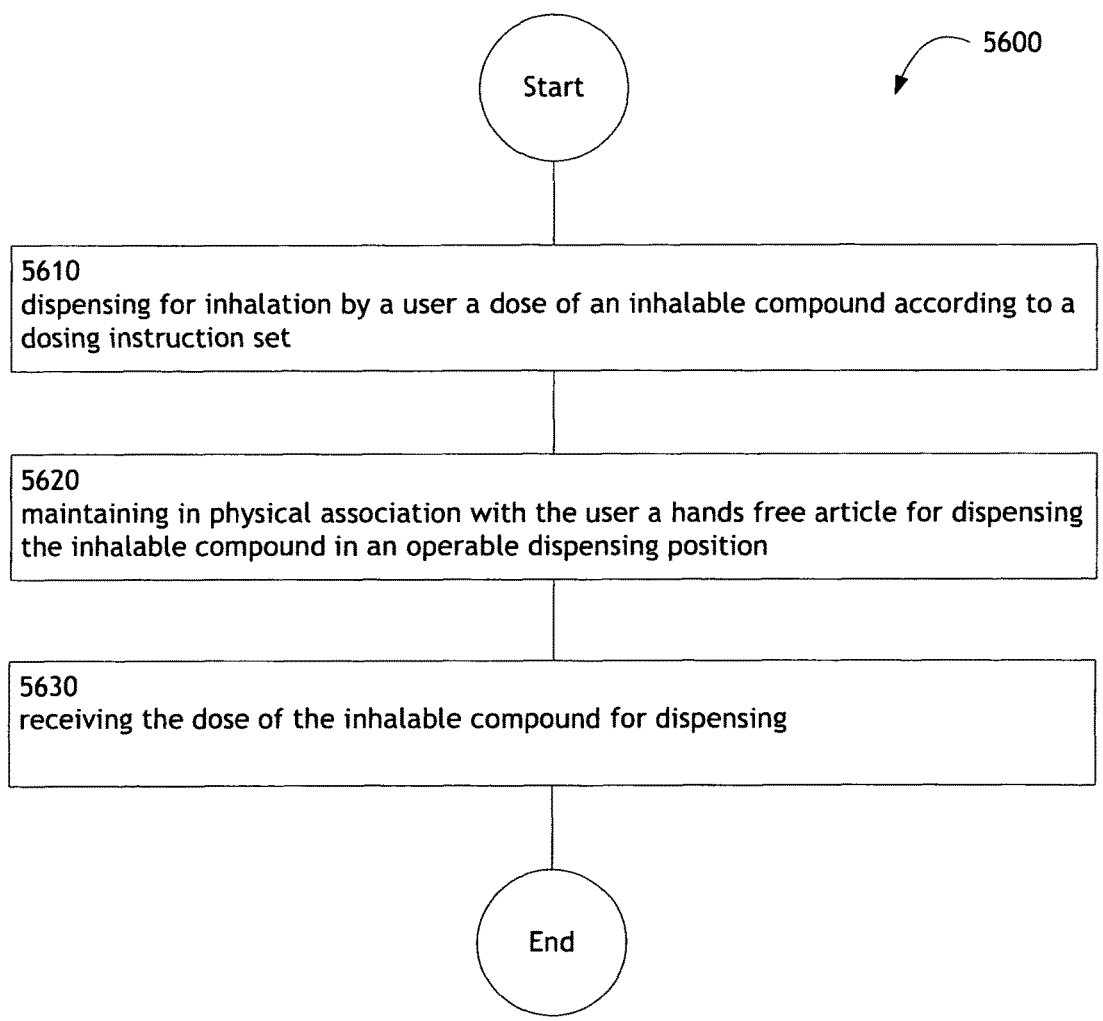
FIG. 56 illustrates an operational flow representing example operations related to maintaining a hands-free article for dispensing an inhalable compound according to a dosing instruction set, where the hands-free article is maintained in an operable dispensing position.

FIG. 8 illustrates alternative embodiments of the example operational flow 5600 of FIG. 56. FIG. 8 illustrates example embodiments where the operation 5630 may include at least one additional operation. Additional operations may include an operation 802, an operation 804, an operation 806, and/or an operation 808.

The operation 802 illustrates receiving a dose of a pharmaceutical compound for dispensing. For example, as shown in FIGS. 1A through 1H, the compound 104 may include a pharmaceutical compound 178. The pharmaceutical compound 178 may be stored in a reservoir 180 of the collar 100. The reservoir 180 may receive one or more doses of the pharmaceutical compound 178 for dispensing.

The operation 804 illustrates receiving a dose of a therapeutic compound for dispensing. For example, as shown in FIGS. 1A through 1H, the compound 104 may include a therapeutic compound 174. The therapeutic compound 174 may be stored in a reservoir 180 of the collar 100. The reservoir 180 may receive one or more doses of the therapeutic compound 174 for dispensing. Further, the operation 806 illustrates receiving a dosing instruction set. For example, as shown in FIGS. 1A through 1H, the dosing instruction set may be received via the interface 164. Further, the operation 808 illustrates receiving a dosing instruction set via a wireless transmission. For example, as shown in FIGS. 1A through 1H, the dosing instruction set may be received via the interface 164, which may include a wireless interface for receiving a wireless transmission.

Figure 9:
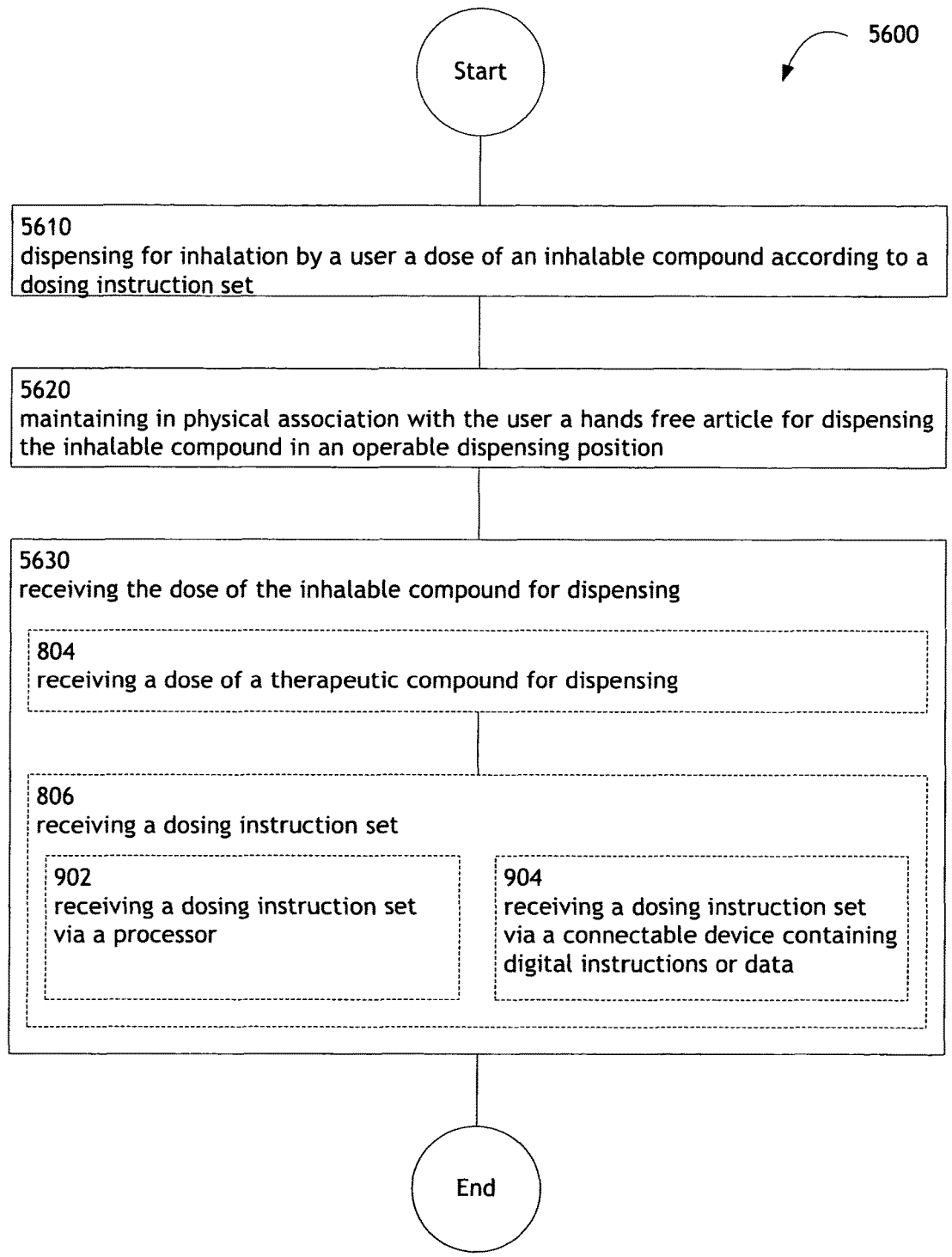

FIG. 9 illustrates alternative embodiments of the example operational flow 5600 of FIG. 56. FIG. 9 illustrates example embodiments where the operation 5630 may include at least one additional operation. Additional operations may include an operation 902, and/or an operation 904. Further, the operation 902 illustrates receiving a dosing instruction set via a processor. For example, as shown in FIGS. 1A through 1H, the processor 156 may receive a dosing instruction set. Further, the operation 904 illustrates receiving a dosing instruction set via a connectable device containing digital instructions or data. For example, as shown in FIGS. 1A through 1H, the collar 100 may receive a dosing instruction set from a connectable device 182 (e.g., a laptop computer, a personal digital assistant (PDA), or a cellular telephone).

Figure 10:
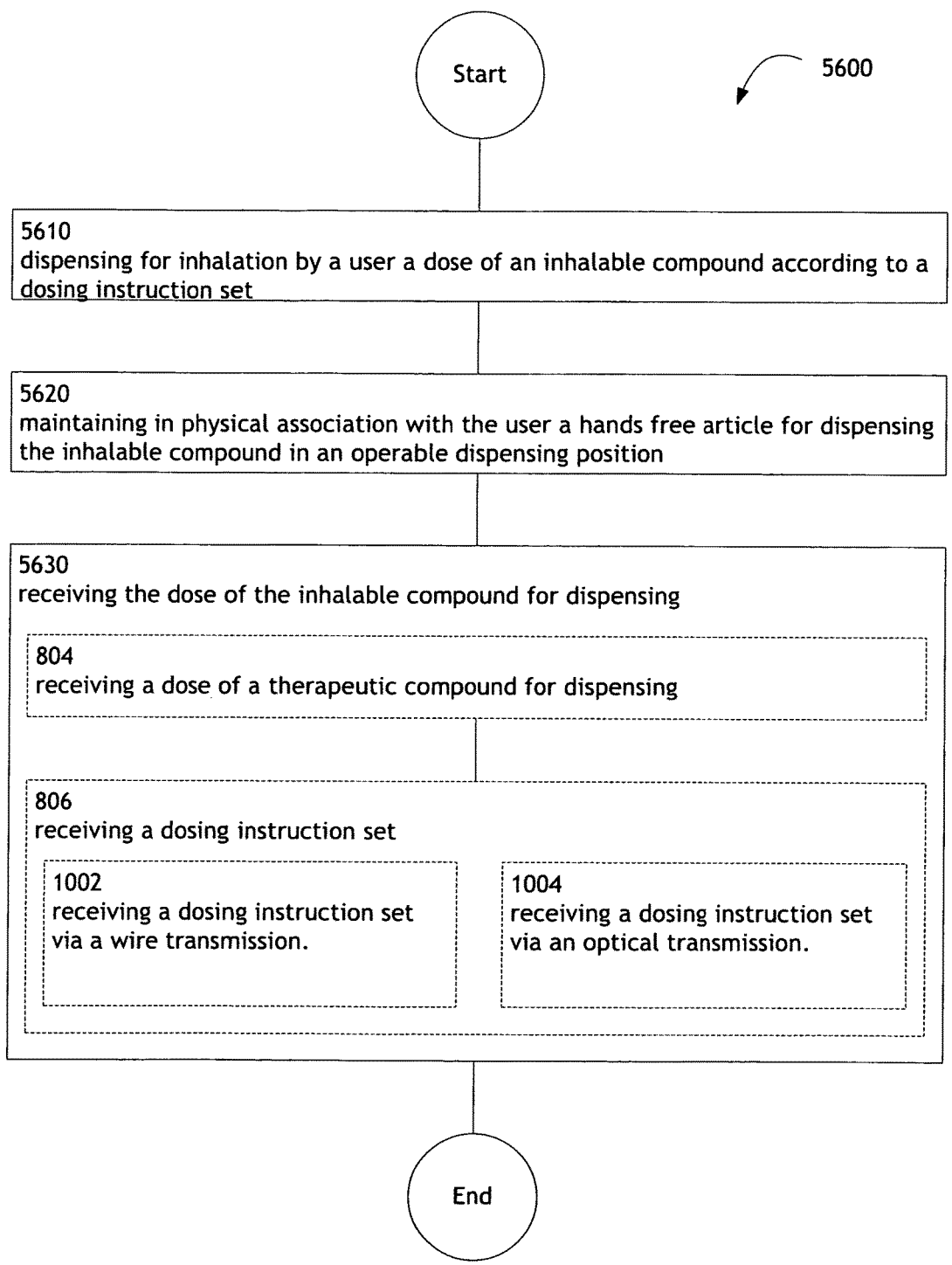

FIG. 10 illustrates alternative embodiments of the example operational flow 5600 of FIG. 56. FIG. 10 illustrates example embodiments where the operation 5630 may include at least one additional operation. Additional operations may include an operation 1002, and/or an operation 1004. Further, the operation 1002 illustrates receiving a dosing instruction set via a wire transmission. For example, as shown in FIGS. 1A through 1H, the device 182 may be connected to the interface 164 via a wired connection. Further, the operation 1004 illustrates receiving a dosing instruction set via an optical transmission. For example, as shown in FIGS. 1A through 1H, the device 182 may be connected to the interface 164 via an optical connection. For instance, the device 182 may include an optical transmitter (e.g., a light), and the interface 164 may include an optical receiver (e.g., a light sensor).

Figure 11:
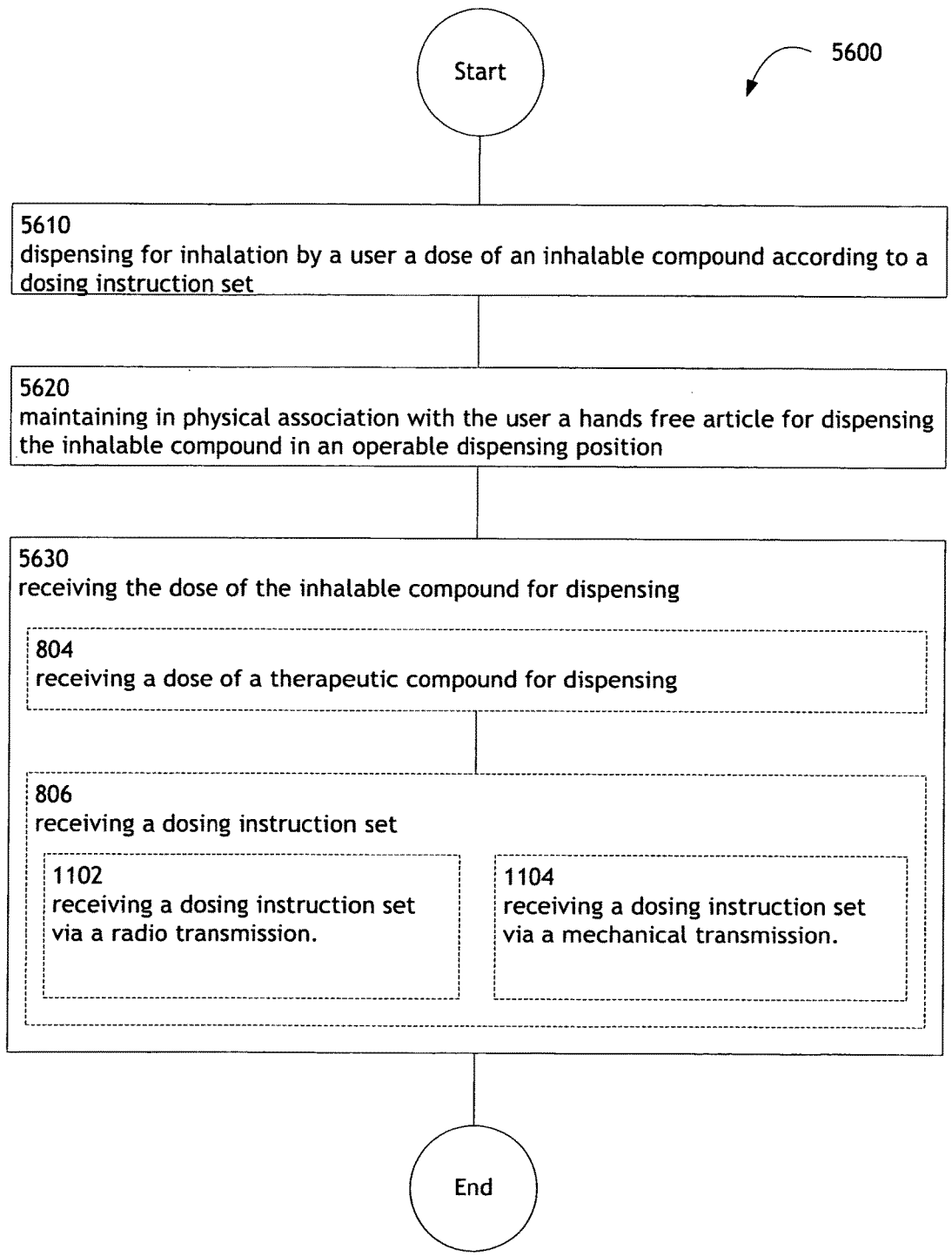

FIG. 11 illustrates alternative embodiments of the example operational flow 5600 of FIG. 56. FIG. 11 illustrates example embodiments where the operation 5630 may include at least one additional operation. Additional operations may include an operation 1102, and/or an operation 1104. Further, the operation 1102 illustrates receiving a dosing instruction set via a radio transmission. For example, as shown in FIGS. 1A through 1H, the device 182 may be connected to the interface 164 via a radio connection. For instance, the device 182 may include a Radio Frequency (RF) transmitter, and the interface 164 may include an RF receiver. Further, the operation 1104 illustrates receiving a dosing instruction set via a mechanical transmission. For example, as shown in FIGS. 1A through 1H, the device 182 may be connected to the interface 164 via a mechanical connection.

Figure 12:
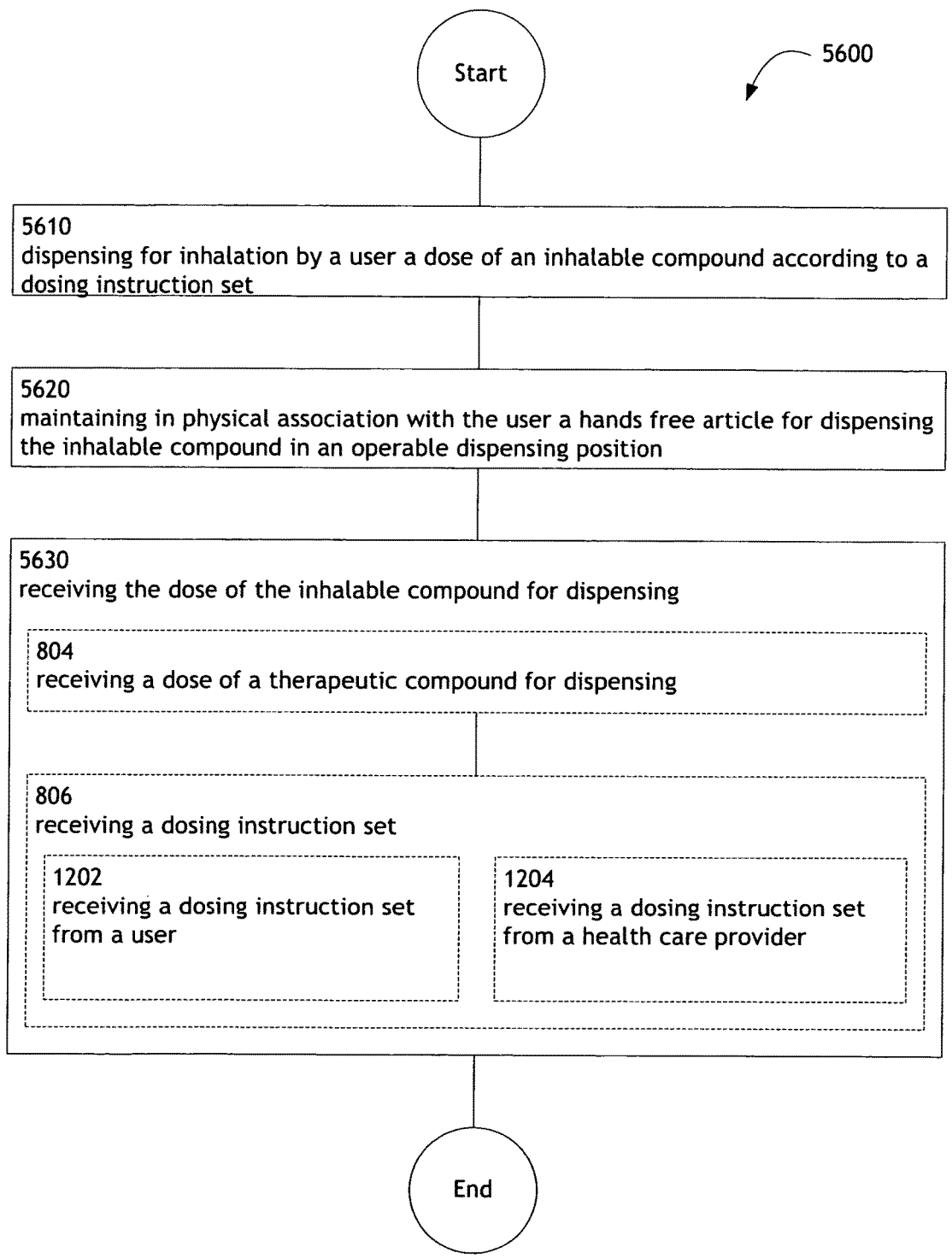

FIG. 12 illustrates alternative embodiments of the example operational flow 5600 of FIG. 56. FIG. 12 illustrates example embodiments where the operation 5630 may include at least one additional operation. Additional operations may include an operation 1202, and/or an operation 1204. Further, the operation 1202 illustrates receiving a dosing instruction set from a user. For example, as shown in FIGS. 1A through 1H, the interface 164 may be utilized to receive a dosing instruction set from a user 166. Further, the operation 1204 illustrates receiving a dosing instruction set from a health care provider. A health care provider may include, for example, a physician, a physician's assistant, a nurse, a nurse practitioner, a pharmacist, or an emergency medical technician. For example, as shown in FIGS. 1A through 1H, the interface 164 may be utilized to receive a dosing instruction set from a physician 168.

Figure 13:
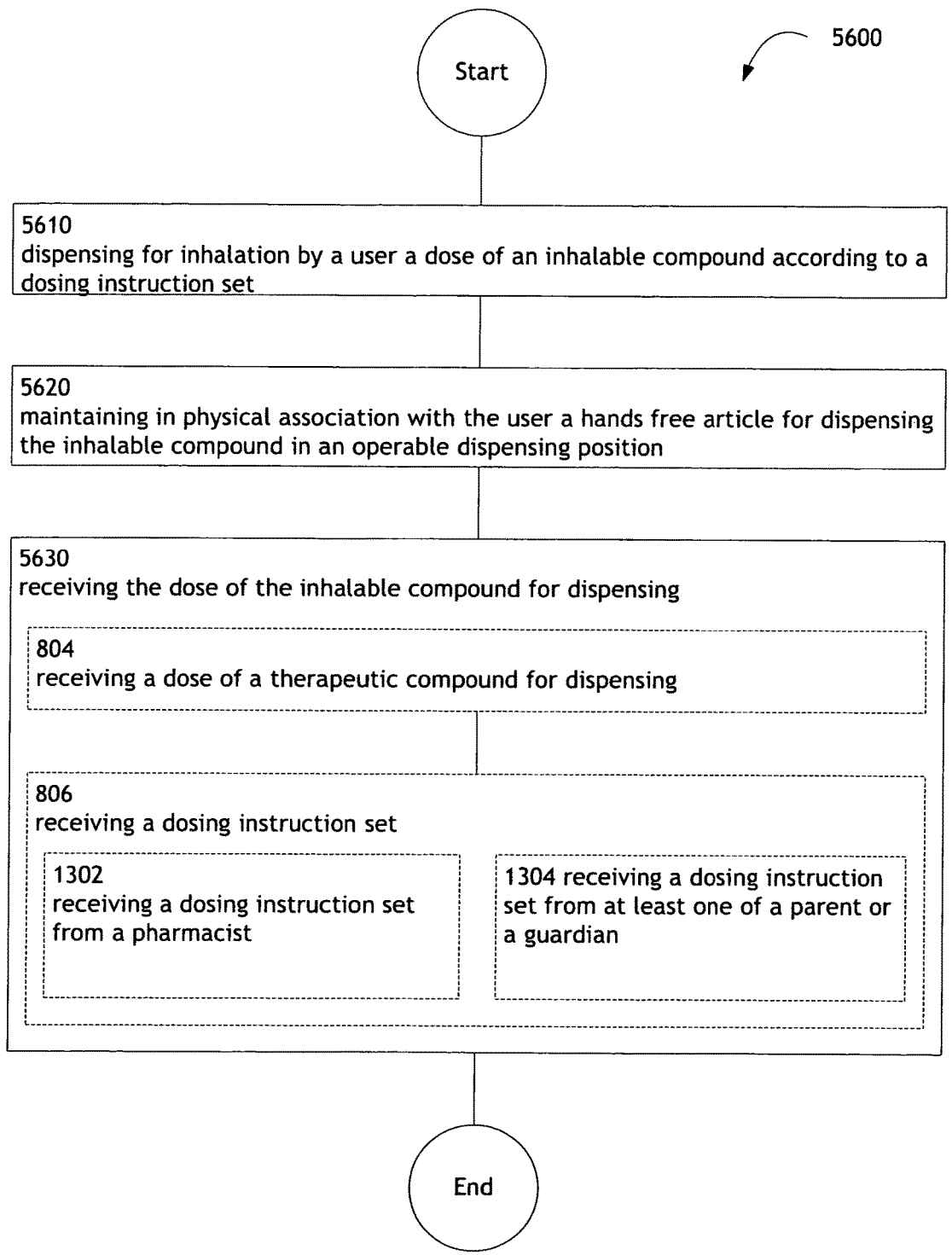

FIG. 13 illustrates alternative embodiments of the example operational flow 5600 of FIG. 56. FIG. 13 illustrates example embodiments where the operation 5630 may include at least one additional operation. Additional operations may include an operation 1302, and/or an operation 1304. Further, the operation 1302 illustrates receiving a dosing instruction set from a pharmacist. For example, as shown in FIGS. 1A through 1H, the interface 164 may be utilized to receive a dosing instruction set from a pharmacist 184. Further, the operation 1304 illustrates receiving a dosing instruction set from at least one of a parent or a guardian. For example, as shown in FIGS. 1A through 1H, the interface 164 may be utilized to receive a dosing instruction set from a parent 186.

Figure 14:
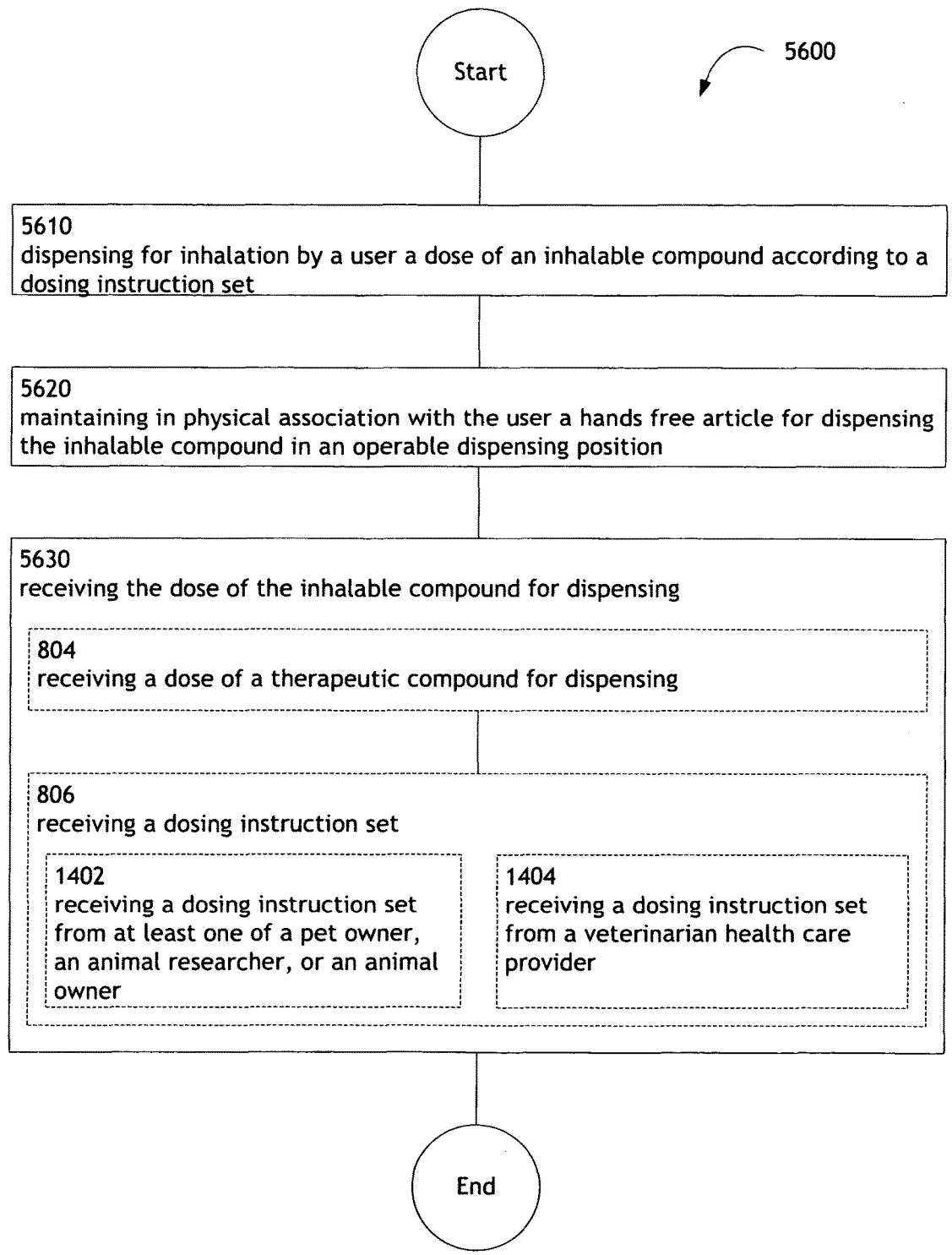

FIG. 14 illustrates alternative embodiments of the example operational flow 5600 of FIG. 56. FIG. 14 illustrates example embodiments where the operation 5630 may include at least one additional operation. Additional operations may include an operation 1402, and/or an operation 1404. Further, the operation 1402 illustrates receiving a dosing instruction set from at least one of a pet owner, an animal researcher, or an animal owner. For example, as shown in FIGS. 1A through 1H, the interface 164 may be utilized to receive a dosing instruction set from a pet owner 188. Further, the operation 1404 illustrates receiving a dosing instruction set from a veterinarian health care provider. A veterinarian health care provider may include, among others, a veterinarian, a veterinarian's assistant, or a veterinarian technician. For example, as shown in FIGS. 1A through 1H, the interface 164 may be utilized to receive a dosing instruction set from a veterinarian 190. In an embodiment, the interface 164, may be utilized to receive a dosing instruction set from a researcher.

Figure 15:
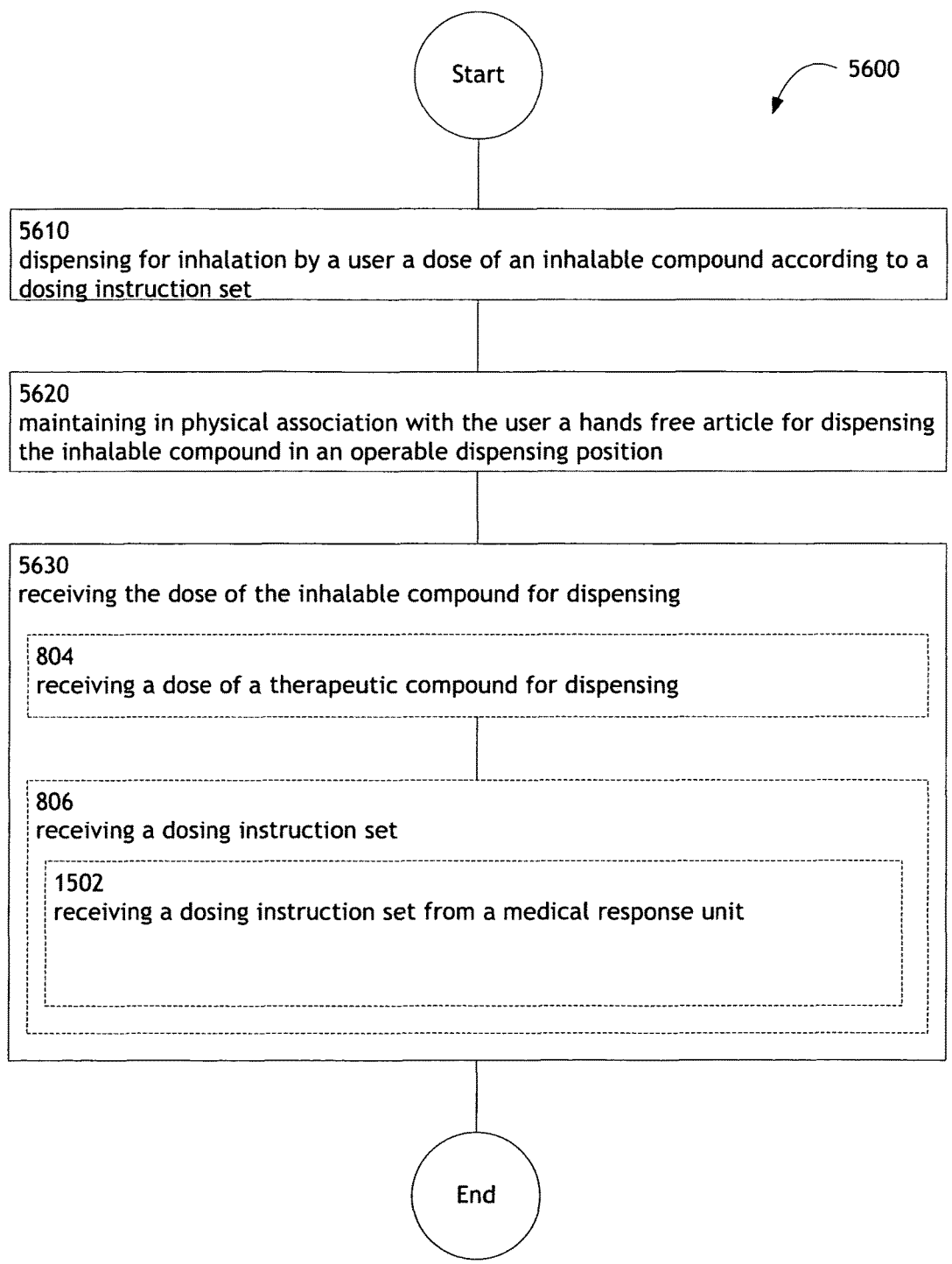

FIG. 15 illustrates alternative embodiments of the example operational flow 5600 of FIG. 56. FIG. 15 illustrates example embodiments where the operation 5630 may include at least one additional operation. Additional operations may include an operation 1502. Further, the operation 1502 illustrates receiving a dosing instruction set from a medical response unit. For example, as shown in FIGS. 1A through 1H, the interface 164 may be utilized to receive a dosing instruction set from a medical response unit 192.

Figure 16:
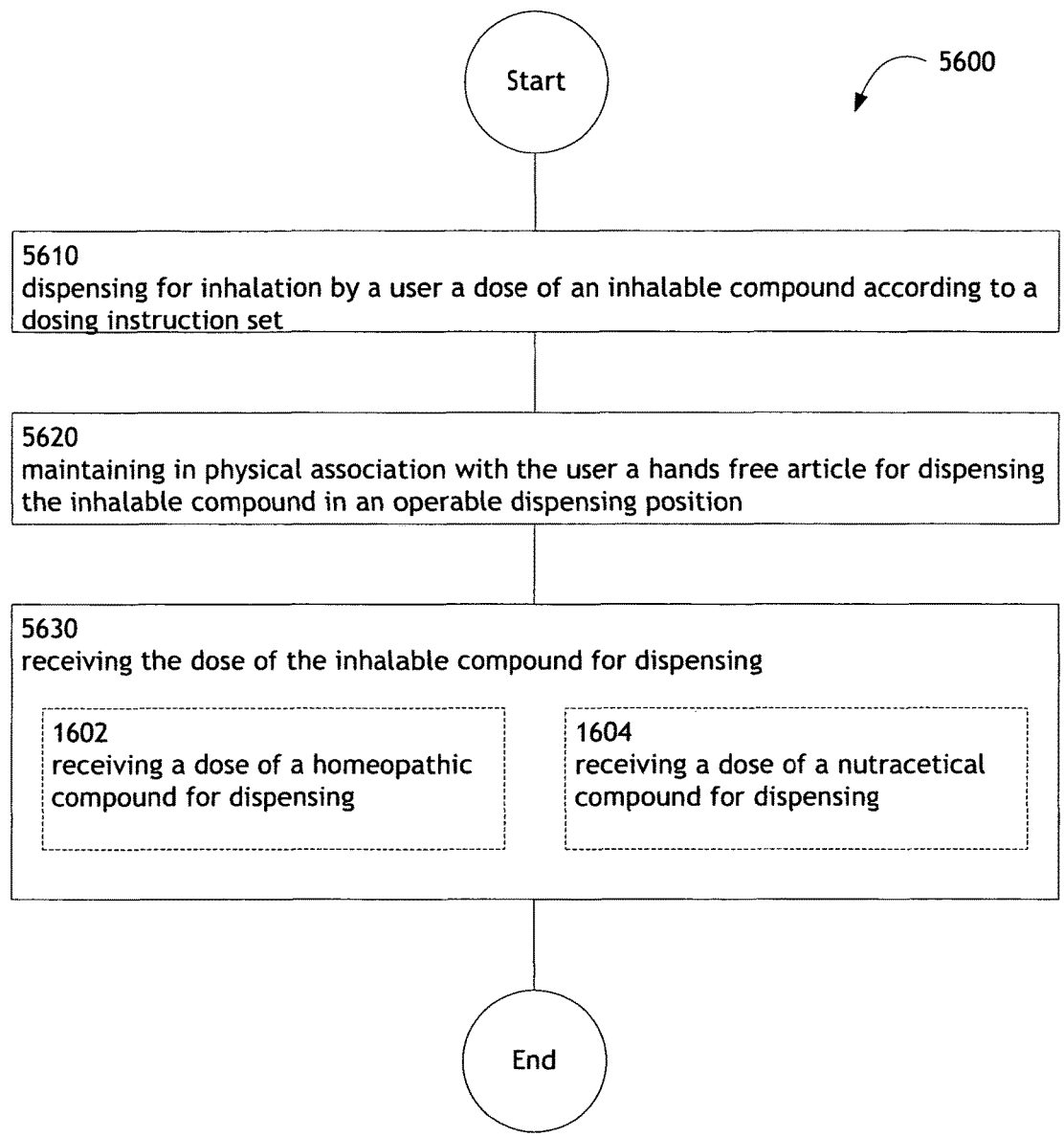

FIG. 16 illustrates alternative embodiments of the example operational flow 5600 of FIG. 56. FIG. 16 illustrates example embodiments where the operation 5630 may include at least one additional operation. Additional operations may include an operation 1602, and/or an operation 1604.

The operation 1602 illustrates receiving a dose of a homeopathic compound for dispensing. For example, as shown in FIGS. 1A through 1H, the compound 104 may include one or more homeopathic compounds 176.

The operation 1604 illustrates receiving a dose of a nutracetical compound for dispensing. For example, as shown in FIGS. 1A through 1H, the compound 104 may include one or more nutraceutical compounds 172.

Figure 17:
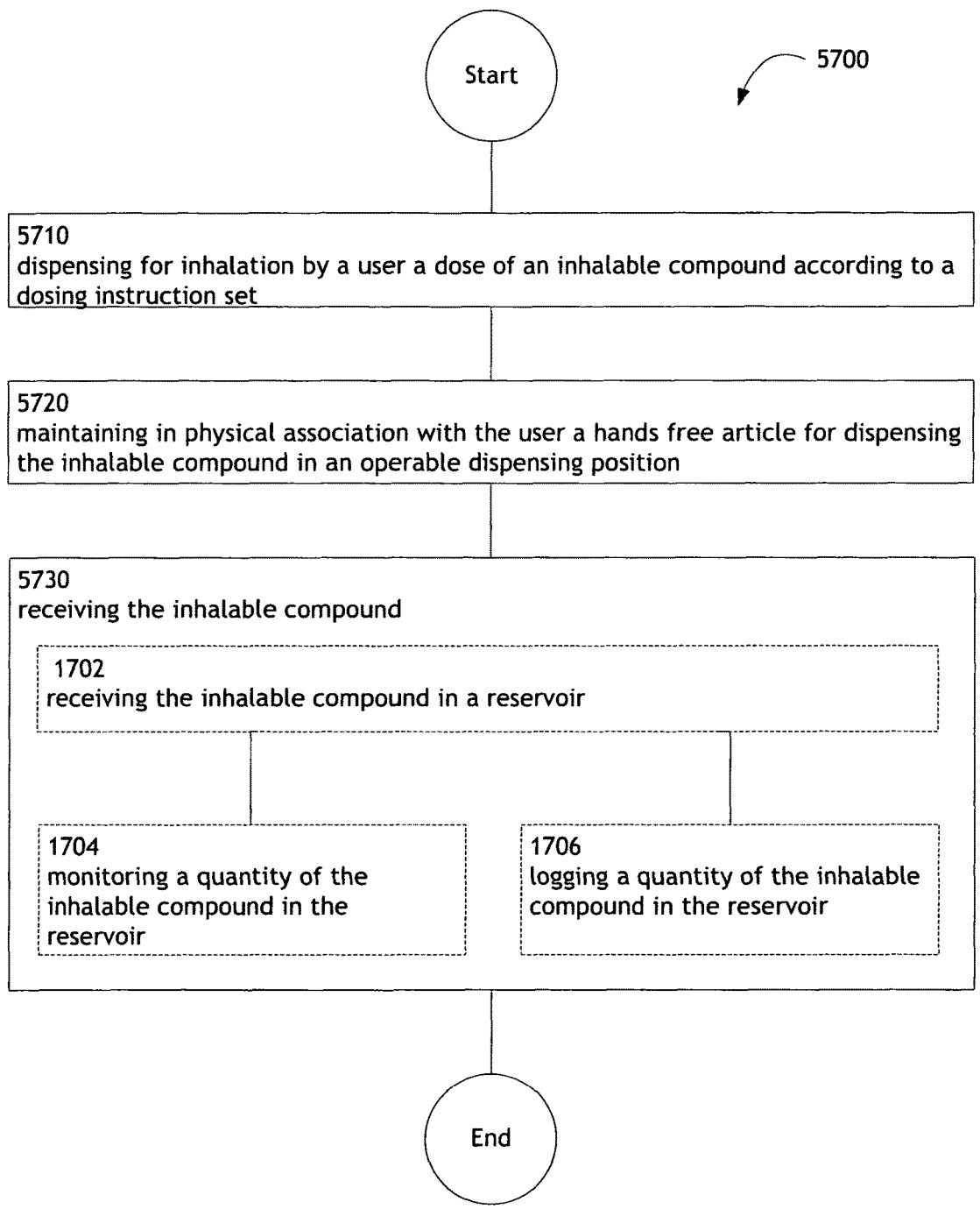
Figure 57:
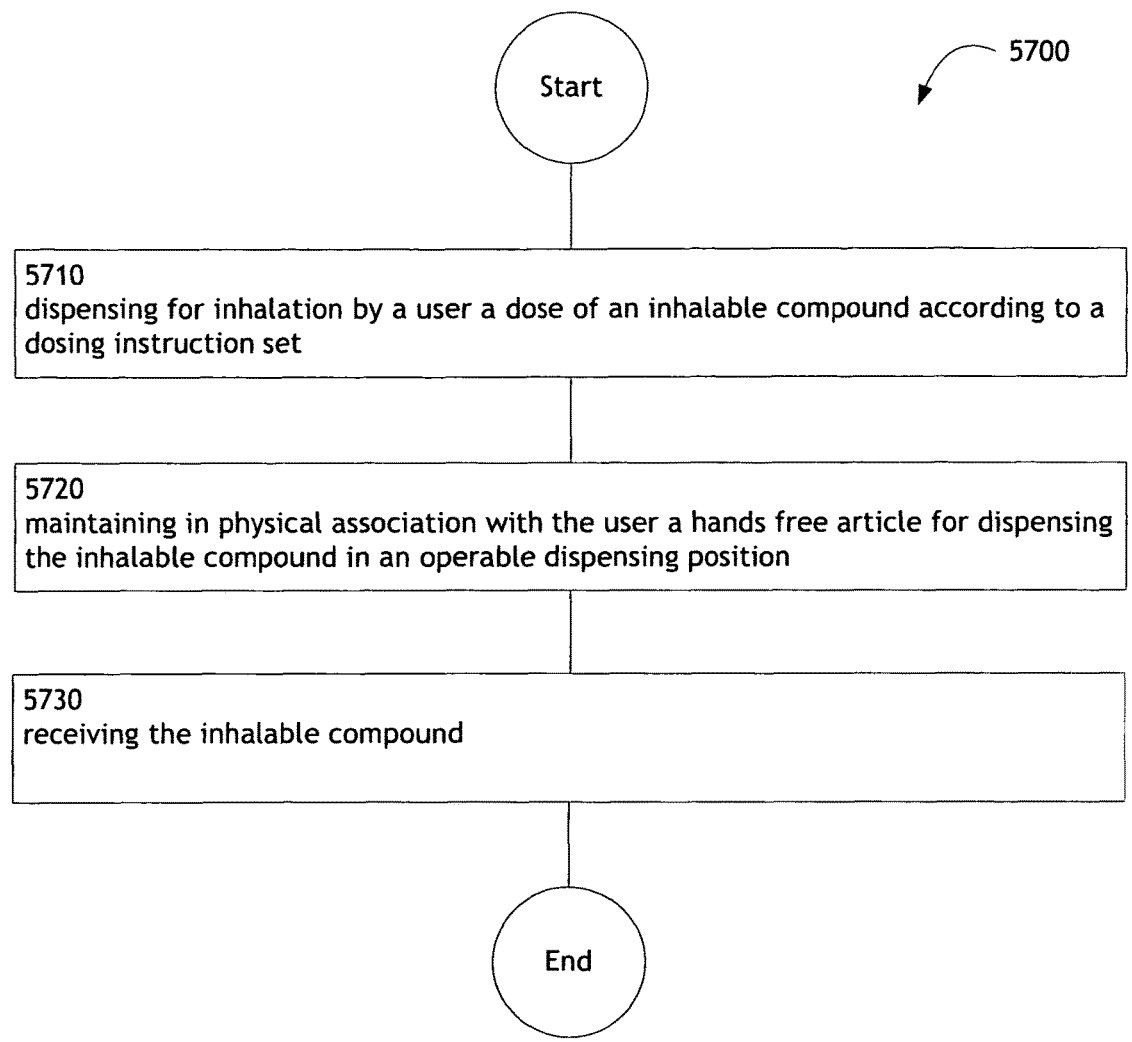
FIG. 57 illustrates an operational flow representing example operations related to maintaining a hands-free article for dispensing an inhalable compound according to a dosing instruction set, where the hands-free article is maintained in an operable dispensing position.

FIG. 17 illustrates alternative embodiments of the example operational flow 5700 of FIG. 57. FIG. 17 illustrates example embodiments where the operation 5730 may include at least one additional operation. Additional operations may include an operation 1702, an operation 1704, and/or an operation 1706.

The operation 1702 illustrates receiving the inhalable compound in a reservoir. For example, as shown in FIGS. 1A through 1H, the compound 104 may be received in a reservoir 180. Further, the operation 1704 illustrates monitoring a quantity of the inhalable compound in the reservoir. For example, as shown in FIGS. 1A through 1H, the processor 156 may be utilized to monitor the compound 104 in the reservoir 180. Further, the operation 1706 illustrates logging a quantity of the inhalable compound in the reservoir. For example, as shown in FIGS. 1A through 1H, the processor 156 may be utilized to monitor the compound 104 in the reservoir 180, and the memory 154 may be utilized to keep a log of a quantity of the compound 104 in the reservoir 180.

Figure 18:
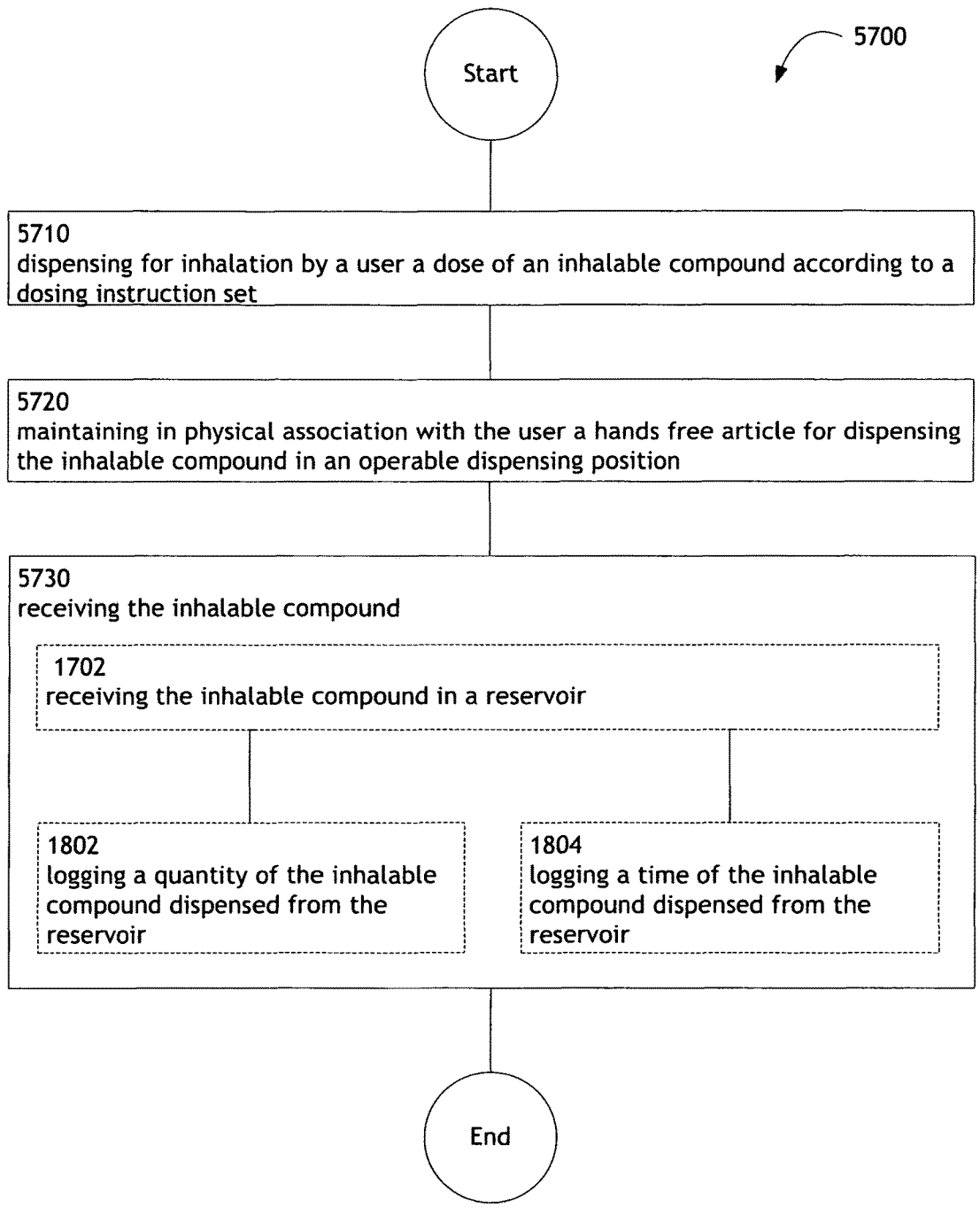

FIG. 18 illustrates alternative embodiments of the example operational flow 5700 of FIG. 57. FIG. 18 illustrates example embodiments where the operation 5730 may include at least one additional operation. Additional operations may include an operation 1802, and/or an operation 1804. Further, the operation 1802 illustrates logging a quantity of the inhalable compound dispensed from the reservoir. For example, as shown in FIGS. 1A through 1H, the processor 156 may be utilized to monitor an amount of the compound 104 dispensed from the reservoir 180, and the memory 154 may be utilized to keep a log of a quantity of the compound 104 dispensed from the reservoir 180. Further, the operation 1804 illustrates logging a time of the inhalable compound dispensed from the reservoir. For example, as shown in FIGS. 1A through 1H, the processor 156 may be utilized to monitor a time of dispensing the compound 104 from the reservoir 180 (e.g., by utilizing the time keeping module 162), and the memory 154 may be utilized to keep a tog of a time of dispensing the compound 104 from the reservoir 180.

Figure 19:
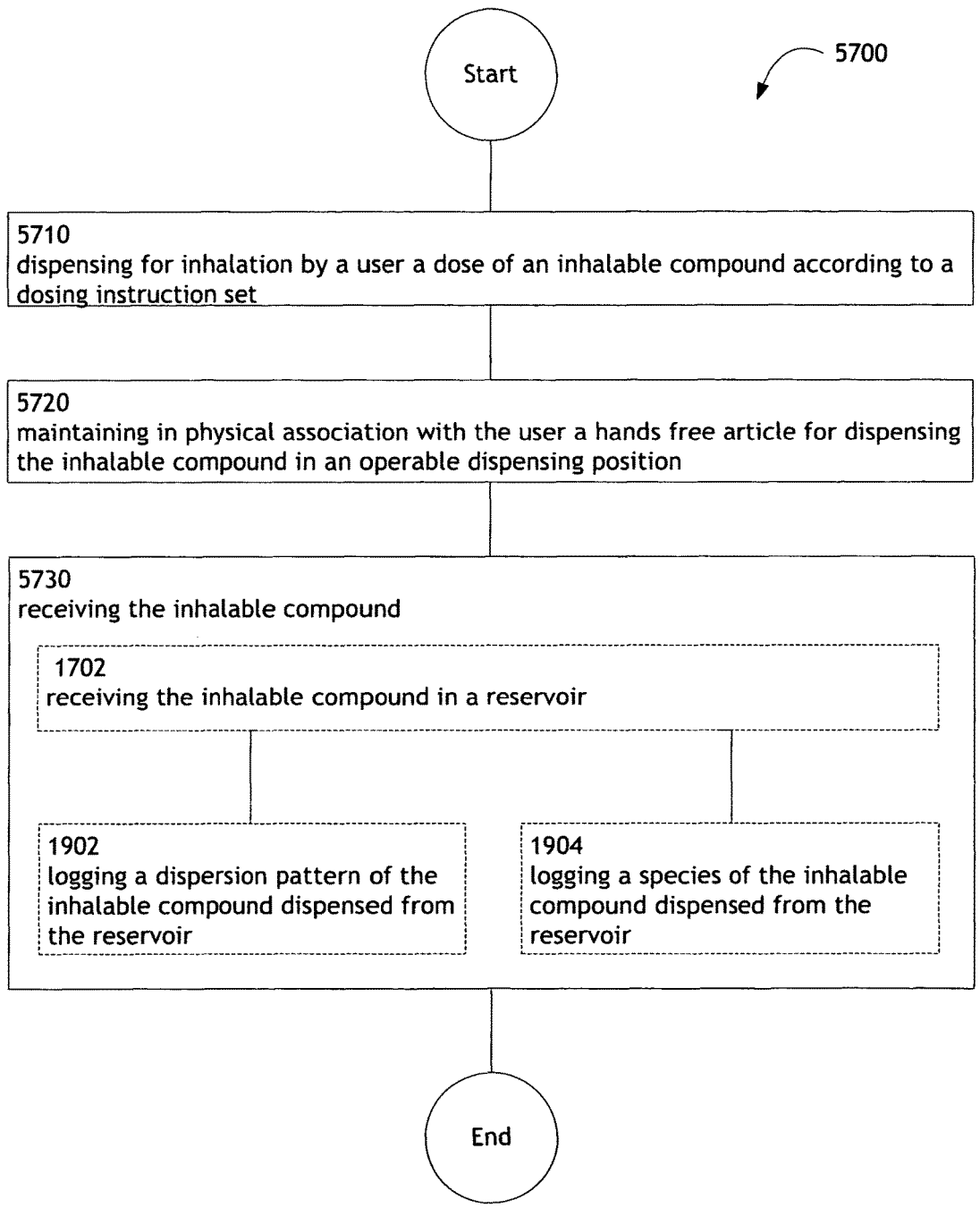

FIG. 19 illustrates alternative embodiments of the example operational flow 5700 of FIG. 57. FIG. 19 illustrates example embodiments where the operation 5730 may include at least one additional operation. Additional operations may include an operation 1902, and/or an operation 1904. Further, the operation 1902 illustrates logging a dispersion pattern of the inhalable compound dispensed from the reservoir. For example, as shown in FIGS. 1A through 1H, the collar 100 may include a camera 194 for monitoring a dispersion pattern of the dispensed compound 104, and the memory 154 may be utilized to log the dispersion pattern. Further, the operation 1904 illustrates logging a species of the inhalable compound dispensed from the reservoir. For example, as shown in FIGS. 1A through 1H, the processor 156 may be utilized to determine a species of the compound 104 dispensed from the reservoir 180, and the memory 154 may be utilized to log the determined species.

Figure 20:
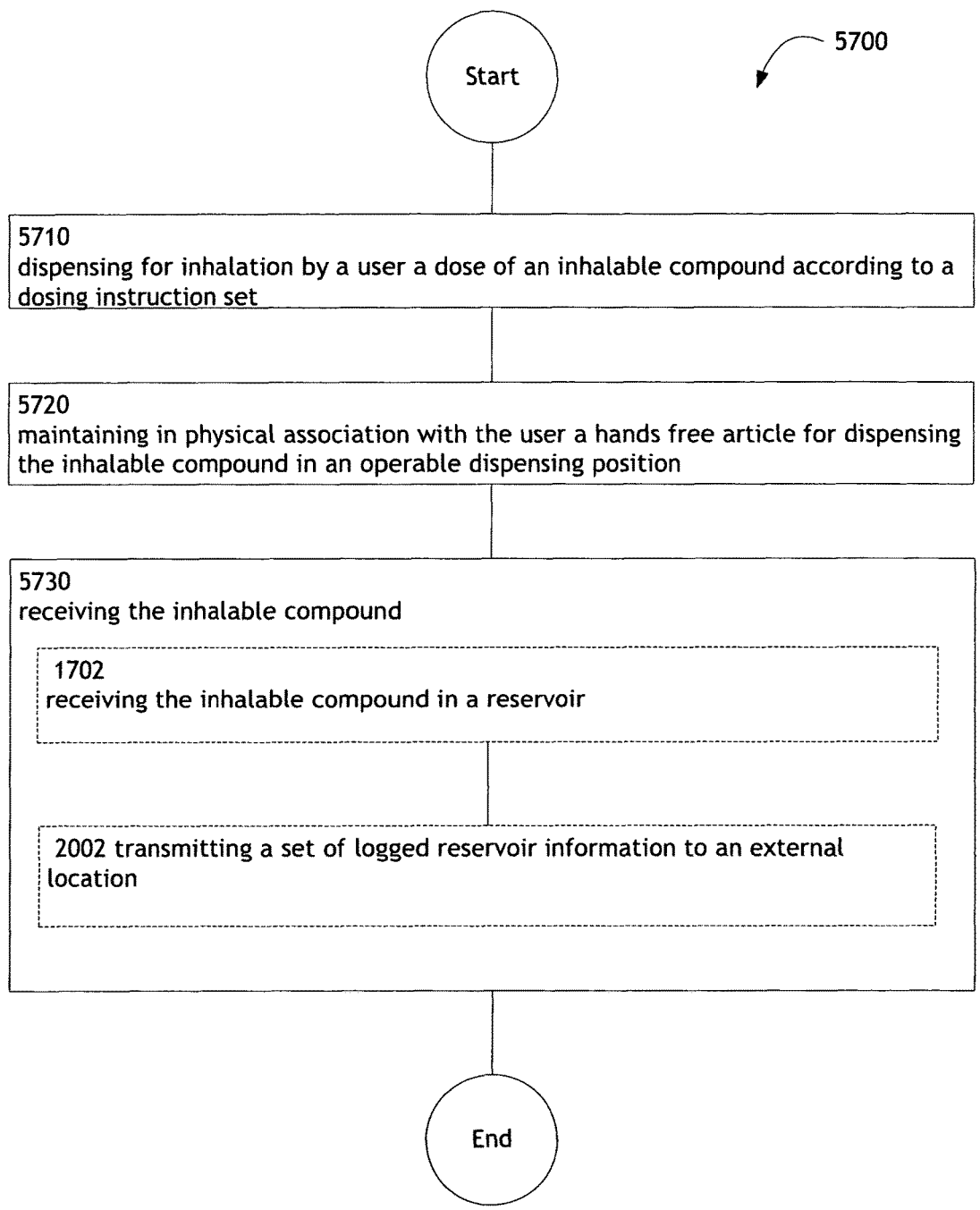

FIG. 20 illustrates alternative embodiments of the example operational flow 5700 of FIG. 57. FIG. 20 illustrates example embodiments where the operation 5730 may include at least one additional operation. Additional operations may include an operation 2002. Further, the operation 2002 illustrates transmitting a set of logged reservoir information to an external location. For example, as shown in FIGS. 1A through 1H, the information logged by the memory 154 may be transmitted to an external location via the interface 164.

Figure 21:
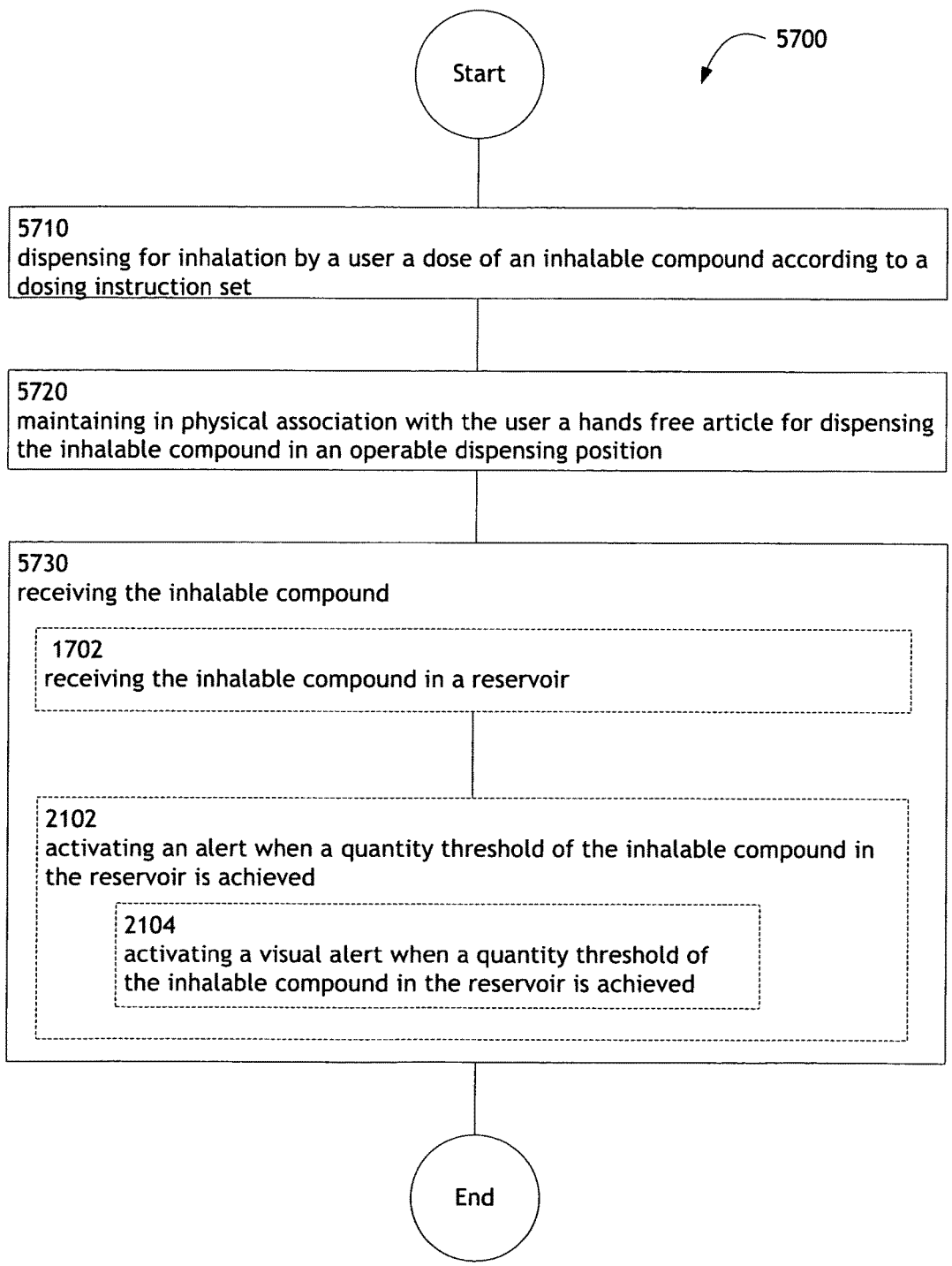

FIG. 21 illustrates alternative embodiments of the example operational flow 5700 of FIG. 57. FIG. 21 illustrates example embodiments where the operation 5730 may include at least one additional operation. Additional operations may include an operation 2102, and/or an operation 2104. Further, the operation 2102 illustrates activating an alert when a quantity threshold of the inhalable compound in the reservoir is achieved. For example, as shown in FIGS. 1A through 1H, the collar 100 may include a visual indicator 196 for issuing an alert when a quantity threshold of the compound 104 is achieved (e.g., as determined by the processor 156). Further, the operation 2104 illustrates activating a visual alert when a quantity threshold of the inhalable compound in the reservoir is achieved. For example, as shown in FIGS. 1A through 1H, the visual indicator 196 may be activated when a quantity threshold of the compound 104 is achieved.

Figure 22:
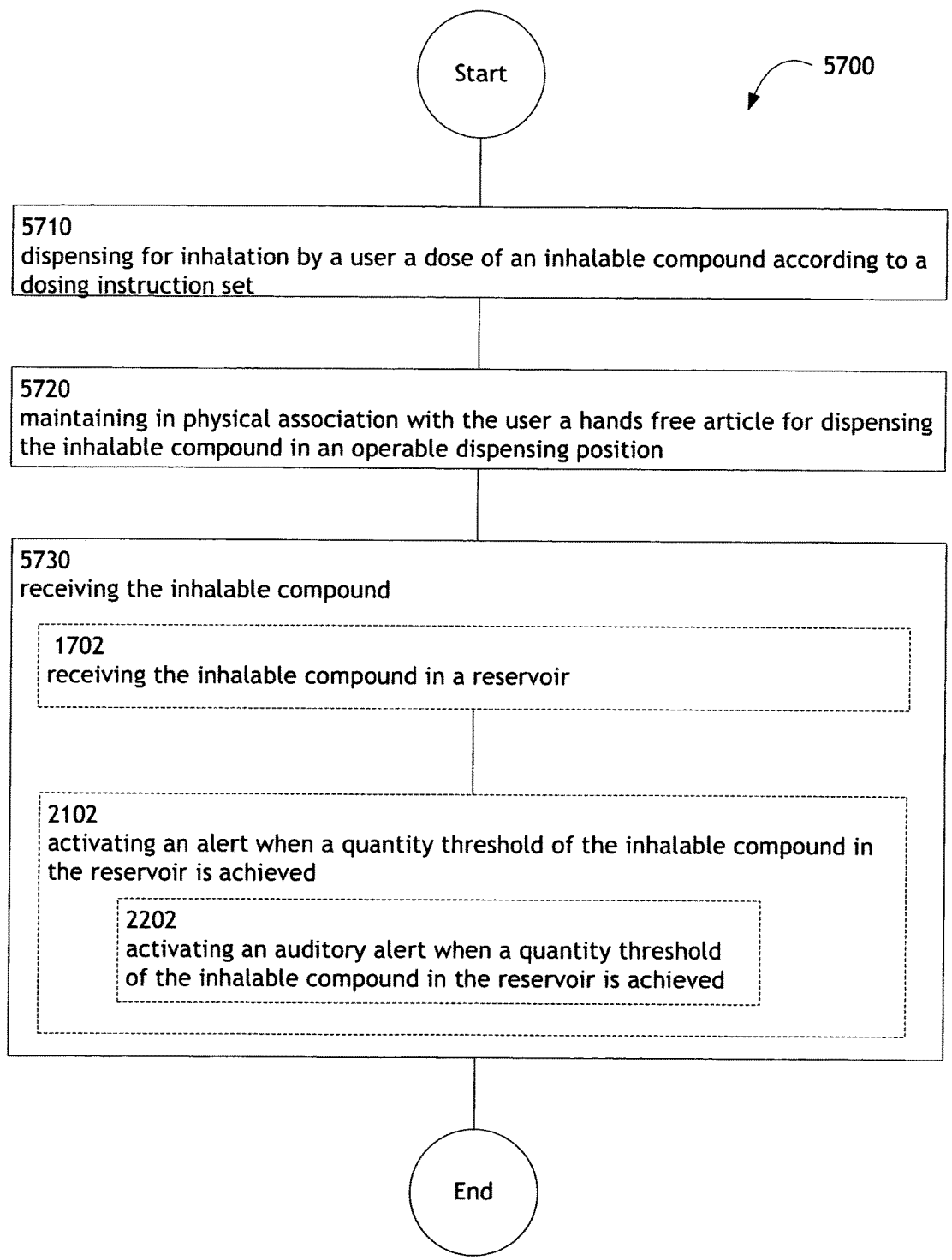

FIG. 22 illustrates alternative embodiments of the example operational flow 5700 of FIG. 57. FIG. 22 illustrates example embodiments where the operation 5730 may include at least one additional operation. Additional operations may include an operation 2202. Further, the operation 2202 illustrates activating an auditory alert when a quantity threshold of the inhalable compound in the reservoir is achieved. For example, as shown in FIGS. 1A through 1H, the collar 100 may include an audible indicator 198 for issuing an auditory alert when a quantity threshold of the compound 104 is achieved.

Figure 23:
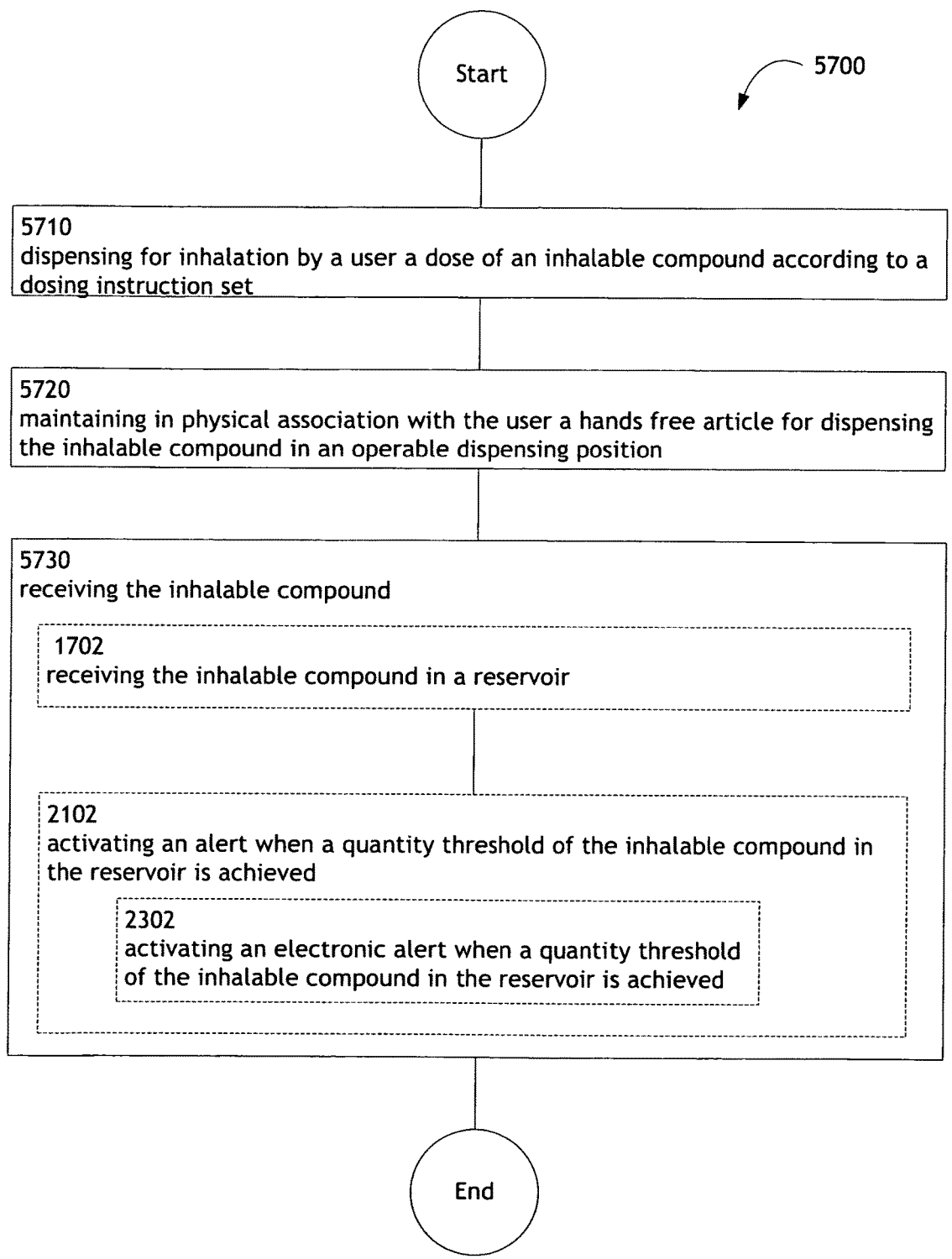

FIG. 23 illustrates alternative embodiments of the example operational flow 5700 of FIG. 57. FIG. 23 illustrates example embodiments where the operation 5730 may include at least one additional operation. Additional operations may include an operation 2302. Further, the operation 2302 illustrates activating an electronic alert when a quantity threshold of the inhalable compound in the reservoir is achieved. For example, as shown in FIGS. 1A through 1H, the collar 100 may include an electronic indicator 50 for issuing an electronic alert when a quantity threshold of the compound 104 is achieved.

Figure 24:
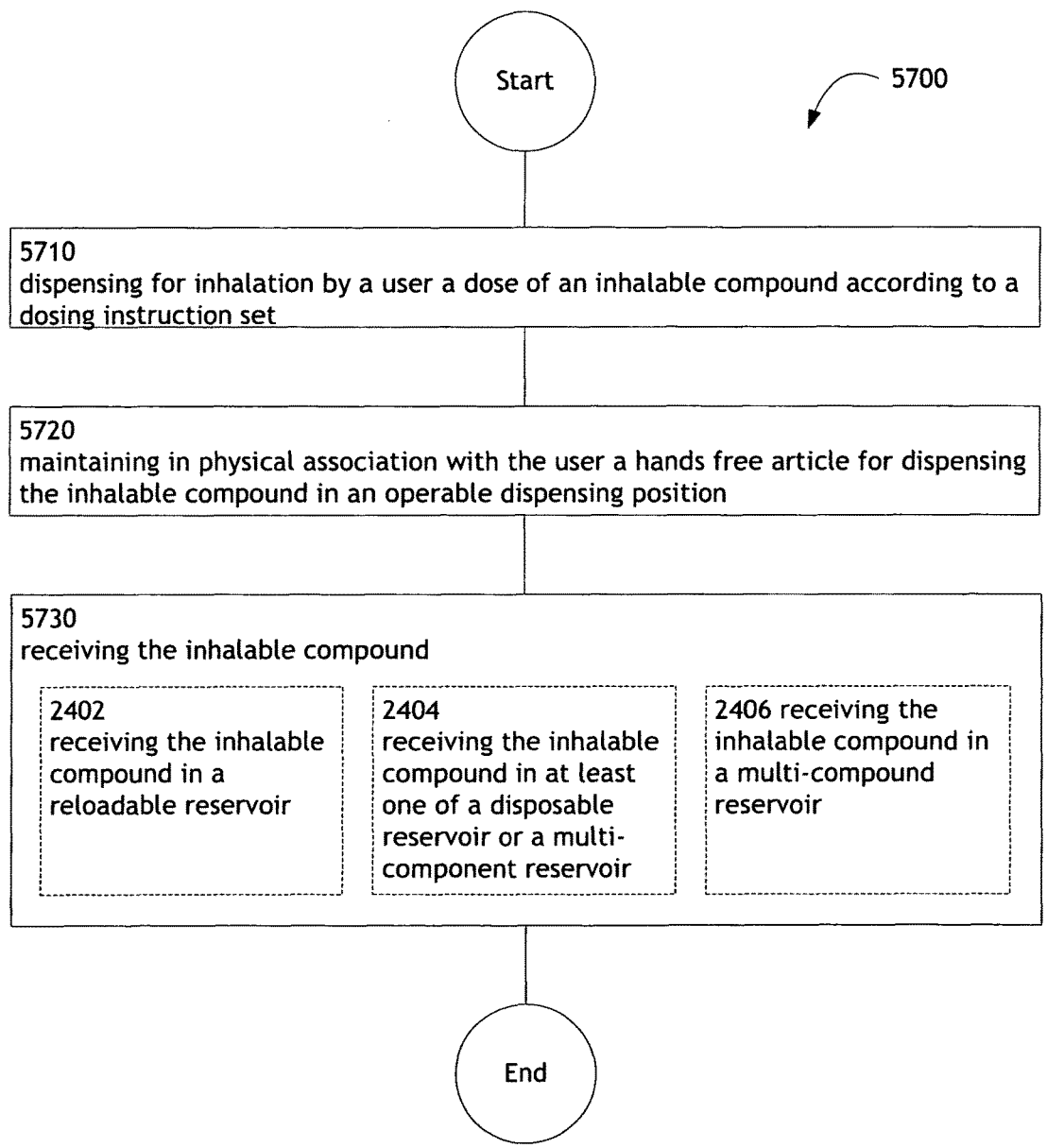

FIG. 24 illustrates alternative embodiments of the example operational flow 5700 of FIG. 57. FIG. 24 illustrates example embodiments where the operation 5730 may include at least one additional operation. Additional operations may include an operation 2402, an operation 2404, and/or an operation 2406.

The operation 2402 illustrates receiving the inhalable compound in a reloadable reservoir. For example, as shown in FIGS. 1A through 1H, the reservoir 180 may include one or more reloadable reservoirs.

The operation 2404 illustrates receiving the inhalable compound in at least one of a disposable reservoir or a multi-component reservoir. For example, as shown in FIGS. 1A through 1H, the reservoir 180 may include one or more disposable reservoirs.

The operation 2406 illustrates receiving the inhalable compound in a multi-compound reservoir. For example, as shown in FIGS. 1A through 1H, the reservoir 180 may include one or more compounds, such as a first compound 104 and a second compound.

Figure 25:
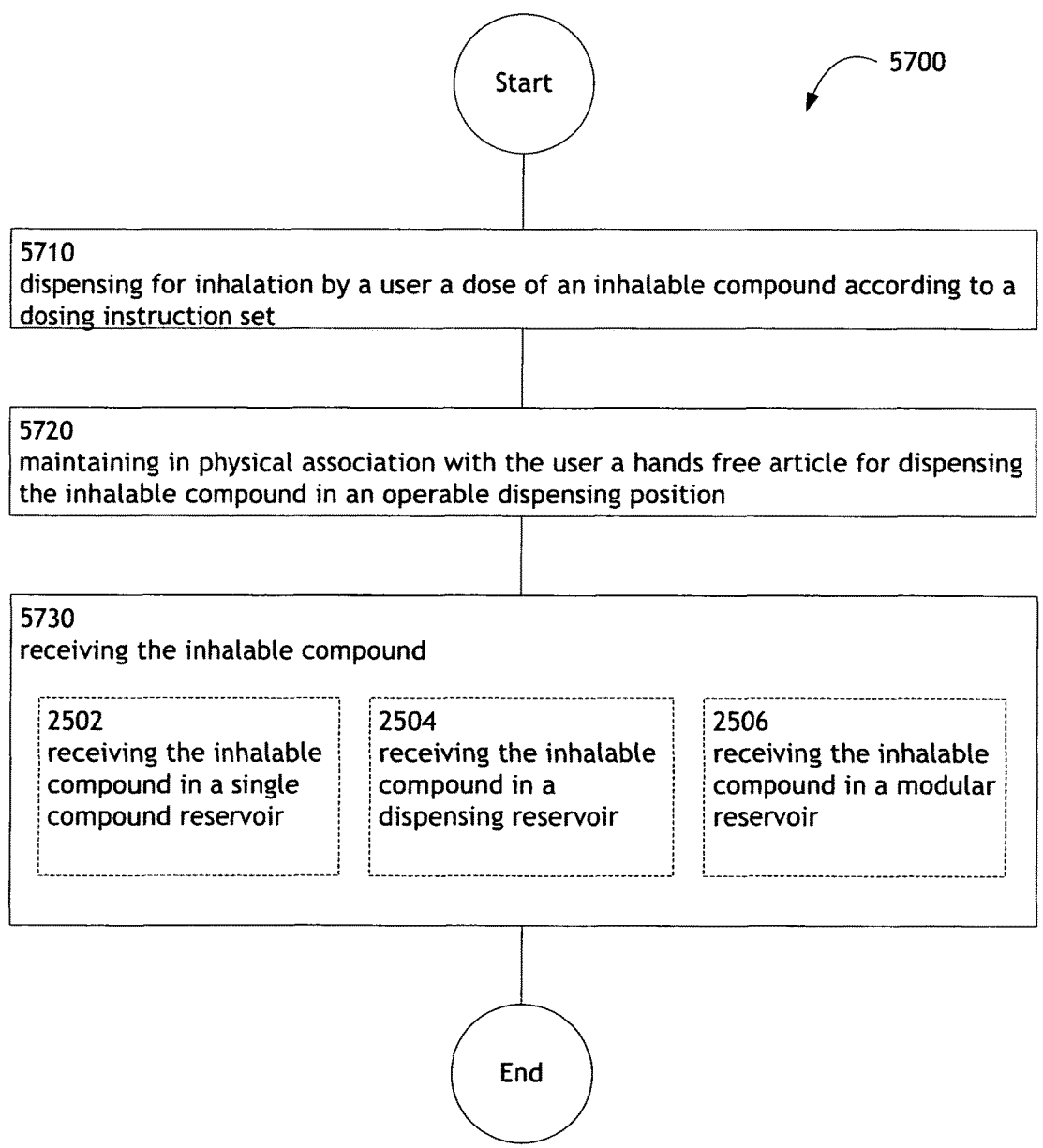

FIG. 25 illustrates alternative embodiments of the example operational flow 5700 of FIG. 57. FIG. 25 illustrates example embodiments where the operation 5730 may include at least one additional operation. Additional operations may include an operation 2502, an operation 2504, and/or an operation 2506.

The operation 2502 illustrates receiving the inhalable compound in a single compound reservoir. For example, as shown in FIGS. 1A through 1H, the reservoir 180 may include a single compound, such as the first compound 104.

The operation 2504 illustrates receiving the inhalable compound in a dispensing reservoir. For example, as shown in FIGS. 1A through 1H, the compound 104 received in the reservoir 180 may be an inhalable compound.

The operation 2506 illustrates receiving the inhalable compound in a modular reservoir. For example, as shown in FIGS. 1A through 1H, the reservoir 180 may include a module reservoir.

Figure 26:
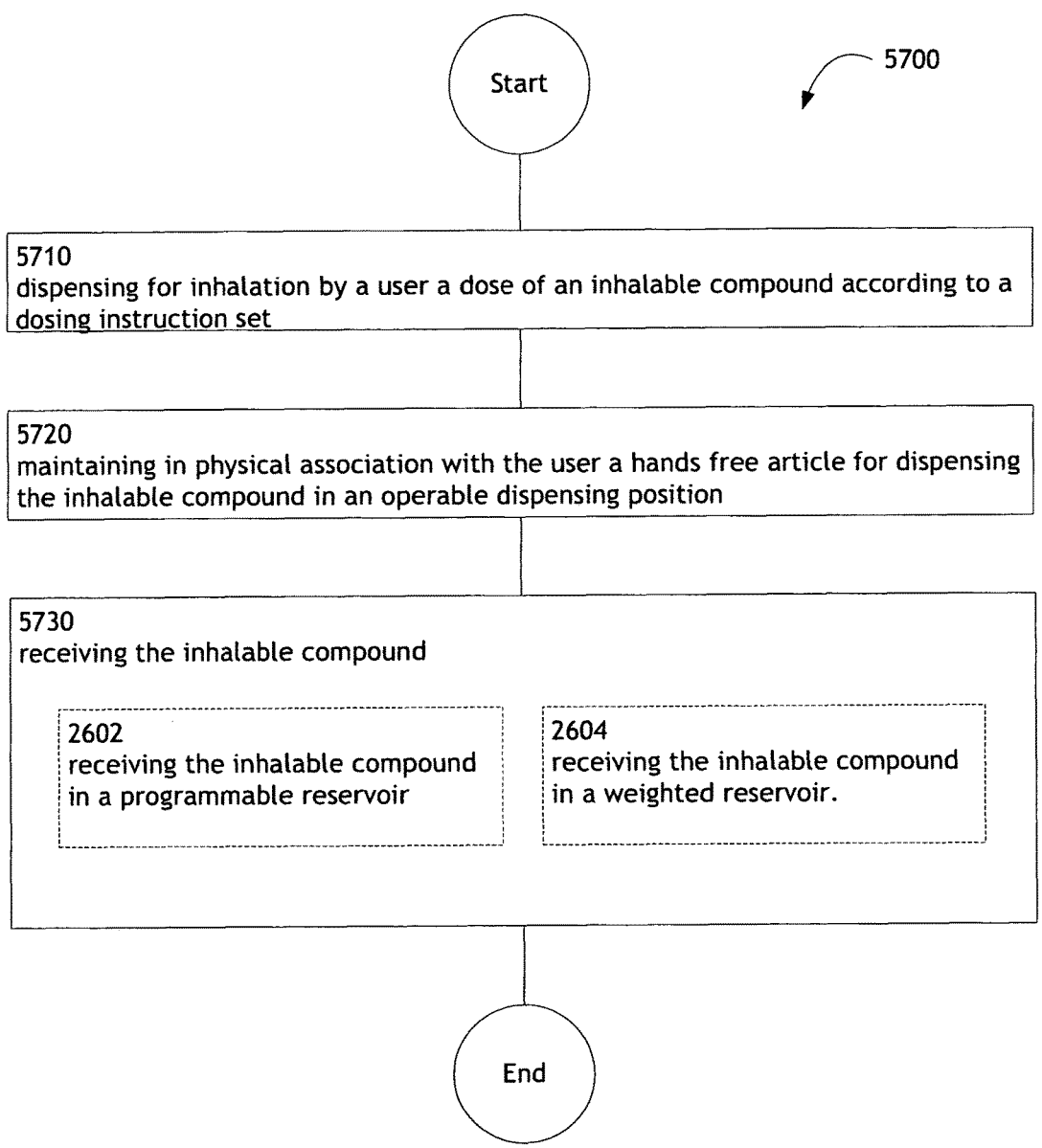

FIG. 26 illustrates alternative embodiments of the example operational flow 5700 of FIG. 57. FIG. 26 illustrates example embodiments where the operation 5730 may include at least one additional operation. Additional operations may include an operation 2602, and/or an operation 2604.

The operation 2602 illustrates receiving the inhalable compound in a programmable reservoir. For example, as shown in FIGS. 1A through 1H, the reservoir 180 may include a programmable reservoir, which may be programmable via the processor 156.

The operation 2604 illustrates receiving the inhalable compound in a weighted reservoir. For example, as shown in FIGS. 1A through 1H, the reservoir 180 may include a weighted reservoir, which may be weighted with a weight 136.

FIG. 27 illustrates alternative embodiments of the example operational flow 5900 of FIG. 59. FIG. 27 illustrates example embodiments where the operation 5930 may include at least one additional operation. Additional operations may include an operation 2702, an operation 2704, and/or an operation 2706.

The operation 2702 illustrates disposing the hands-free aerosol delivery system substantially around a portion of the body of a mammal. For example, as shown in FIGS. 1A through 1H, the collar 100 may encircle the neck portion 106 of a subject 102. Further, the operation 2704 illustrates encircling a neck portion of the body of a mammal with a support member of the hands-free aerosol delivery device. For example, as shown in FIGS. 1A through 1H, the collar 100 may encircle the neck portion 106 of a subject 102. Further, the operation 2706 illustrates encircling a wrist portion of the body of a mammal with a support member of the hands-free aerosol delivery device. For example, as shown in FIGS. 1A through 1H, the collar 100 may encircle the wrist portion 108 of a subject 102.

FIG. 28 illustrates alternative embodiments of the example operational flow 5900 of FIG. 59. FIG. 28 illustrates example embodiments where the operation 5930 may include at least one additional operation. Additional operations may include an operation 2802, and/or an operation 2804. Further, the operation 2802 illustrates encircling a chest portion of the body of a mammal with a support member of the hands-free aerosol delivery device. For example, as shown in FIGS. 1A through 1H, the collar 100 may encircle a chest portion 110 of the subject 102. Further, the operation 2804 illustrates encircling a head portion of the body of a mammal with a support member of the hands-free aerosol delivery device. For example, as shown in FIGS. 1A through 1H, the collar 100 may encircle a head portion 112 of the subject 102.

FIG. 29 illustrates alternative embodiments of the example operational flow 5900 of FIG. 59. FIG. 29 illustrates example embodiments where the operation 5930 may include at least one additional operation. Additional operations may include an operation 2902, and/or an operation 2904. Further, the operation 2902 illustrates connecting a first end of a support member of a hands-free aerosol delivery device to a second end of a support member of a hands-free aerosol delivery device while creating a circle about the body part of a mammal. For example, as shown in FIGS. 1A through 1H, the collar 100 may comprise a support member having a first end 114 and a second end 116. The first end 114 may be connected to the second end 116, encircling and creating a closed loop (e.g., a circle) about the body part of the subject 102. Further, the operation 2904 illustrates connecting the first end of a support member of the hands-free aerosol delivery device to the second end of a support member of the hands-free aerosol delivery device via a magnet. For example, as shown in FIGS. 1A through 1H, the first end 114 may be connected to the second end 116 via a magnet 118.

FIG. 30 illustrates alternative embodiments of the example operational flow 5900 of FIG. 59. FIG. 30 illustrates example embodiments where the operation 5930 may include at least one additional operation. Additional operations may include an operation 3002. Further, the operation 3002 illustrates connecting the first end of a support member of the hands-free aerosol delivery device to the second end of a support member of the hands-free aerosol delivery device via a hook. For example, as shown in FIGS. 1A through 1H, the first end 114 of the collar 100 may be connected to the second end 116 of the collar 100 via a hook 120.

Figure 31:
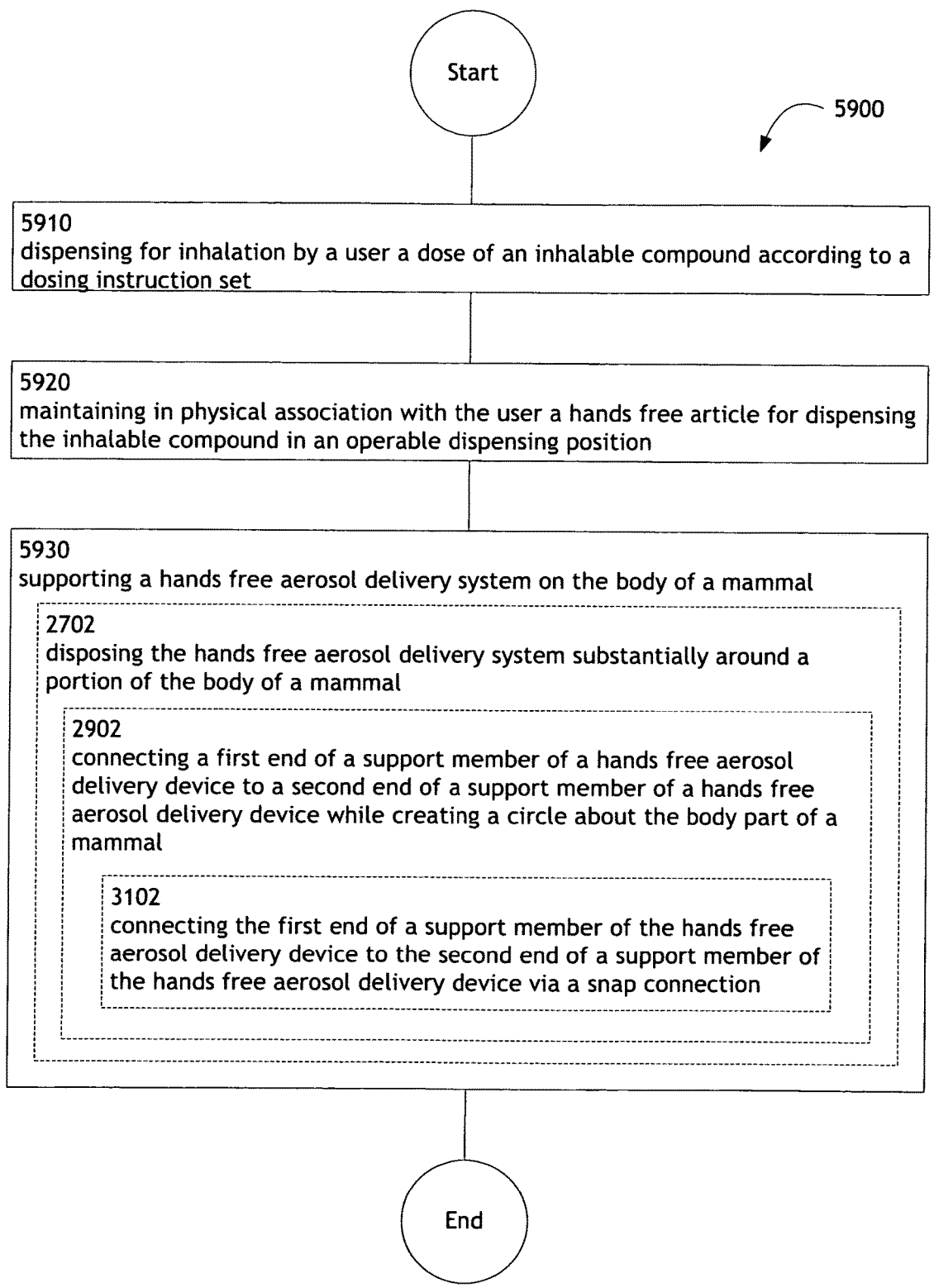
FIG. 31 illustrates an alternative embodiment of the operational flow of FIG. 59.

FIG. 31 illustrates alternative embodiments of the example operational flow 5900 of FIG. 59. FIG. 31 illustrates example embodiments where the operation 5930 may include at least one additional operation. Additional operations may include an operation 3102. Further, the operation 3102 illustrates connecting the first end of a support member of the hands-free aerosol delivery device to the second end of a support member of the hands-free aerosol delivery device via a snap connection. For example, as shown in FIGS. 1A through 1H, the first end 114 may be connected to the second end 116 via a snap connection 122.

FIG. 32 illustrates alternative embodiments of the example operational flow 5900 of FIG. 59. FIG. 32 illustrates example embodiments where the operation 5930 may include at least one additional operation. Additional operations may include an operation 3202. Further, the operation 3202 illustrates connecting the first end of a support member of the hands-free aerosol delivery device to the second end of a support member of the hands-free aerosol delivery device via a threaded connection. For example, as shown in FIGS. 1A through 1H, the first end 114 of the collar 100 may be connected to the second end 116 of the collar 100 via a threaded connection 124.

FIG. 33 illustrates alternative embodiments of the example operational flow 5900 of FIG. 59. FIG. 33 illustrates example embodiments where the operation 5930 may include at least one additional operation. Additional operations may include an operation 3302. Further, the operation 3302 illustrates connecting the first end of a support member of the hands-free aerosol delivery device to the second end of a support member of the hands-free aerosol delivery device via a belt-like connection. For example, as shown in FIGS. 1A through 1H, the first end 114 may be connected to the second end 116 via a belt-like connection 126.

Figure 34:
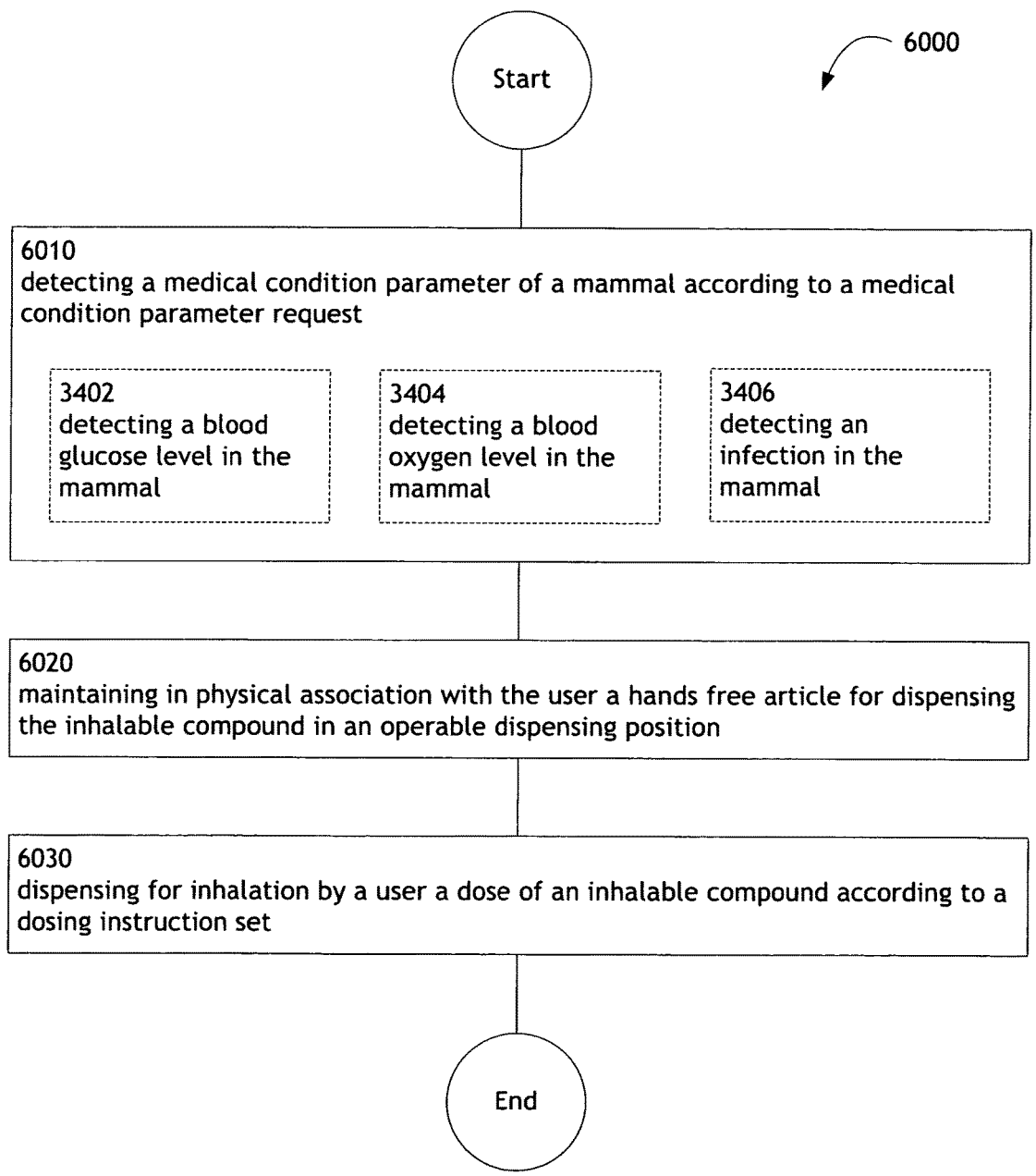
FIG. 34 illustrates an alternative embodiment of the operational flow of FIG. 60.
Figure 60:
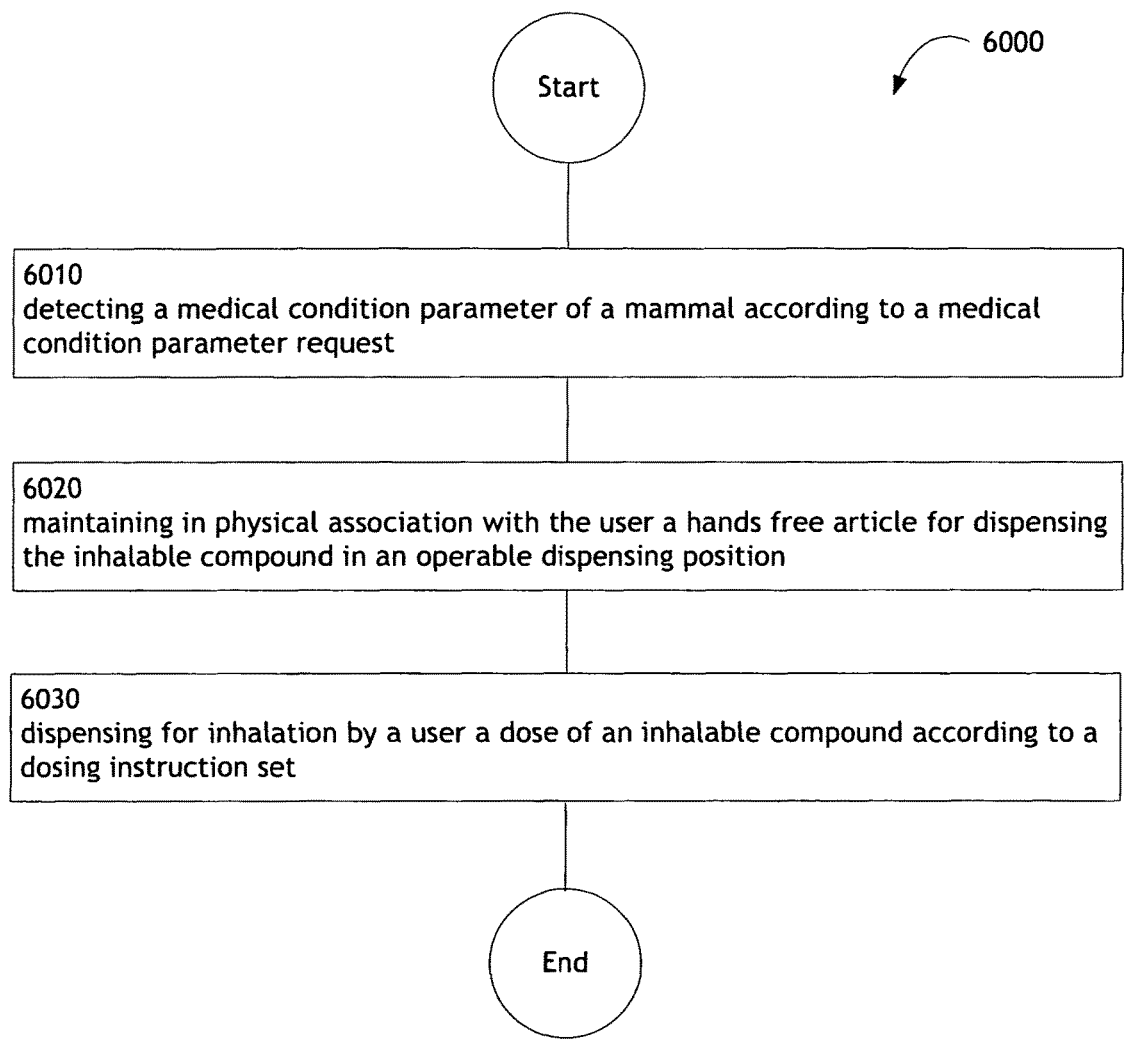
FIG. 60 illustrates an operational flow representing example operations related to maintaining a hands-free article for dispensing an inhalable compound according to a dosing instruction set, where the hands-free article is maintained in an operable dispensing position.

FIG. 34 illustrates alternative embodiments of the example operational flow 6000 of FIG. 60. FIG. 34 illustrates example embodiments where the operation 6010 may include at least one additional operation. Additional operations may include an operation 3402, an operation 3404, and/or an operation 3406.

The operation 3402 illustrates detecting a blood glucose level in the mammal. For example, as shown in FIGS. 1A through 1H, the sensor module 170 may be utilized to detect a blood glucose level in the subject 102.

The operation 3404 illustrates detecting a blood oxygen level in the mammal. For example, as shown in FIGS. 1A through 1H, the sensor module 170 may be utilized to detect a blood oxygen level in the subject 102.

The operation 3406 illustrates detecting an infection in the mammal. For example, as shown in FIGS. 1A through 1H, the sensor module 170 may be utilized to detect an infection in the subject 102.

Figure 35:
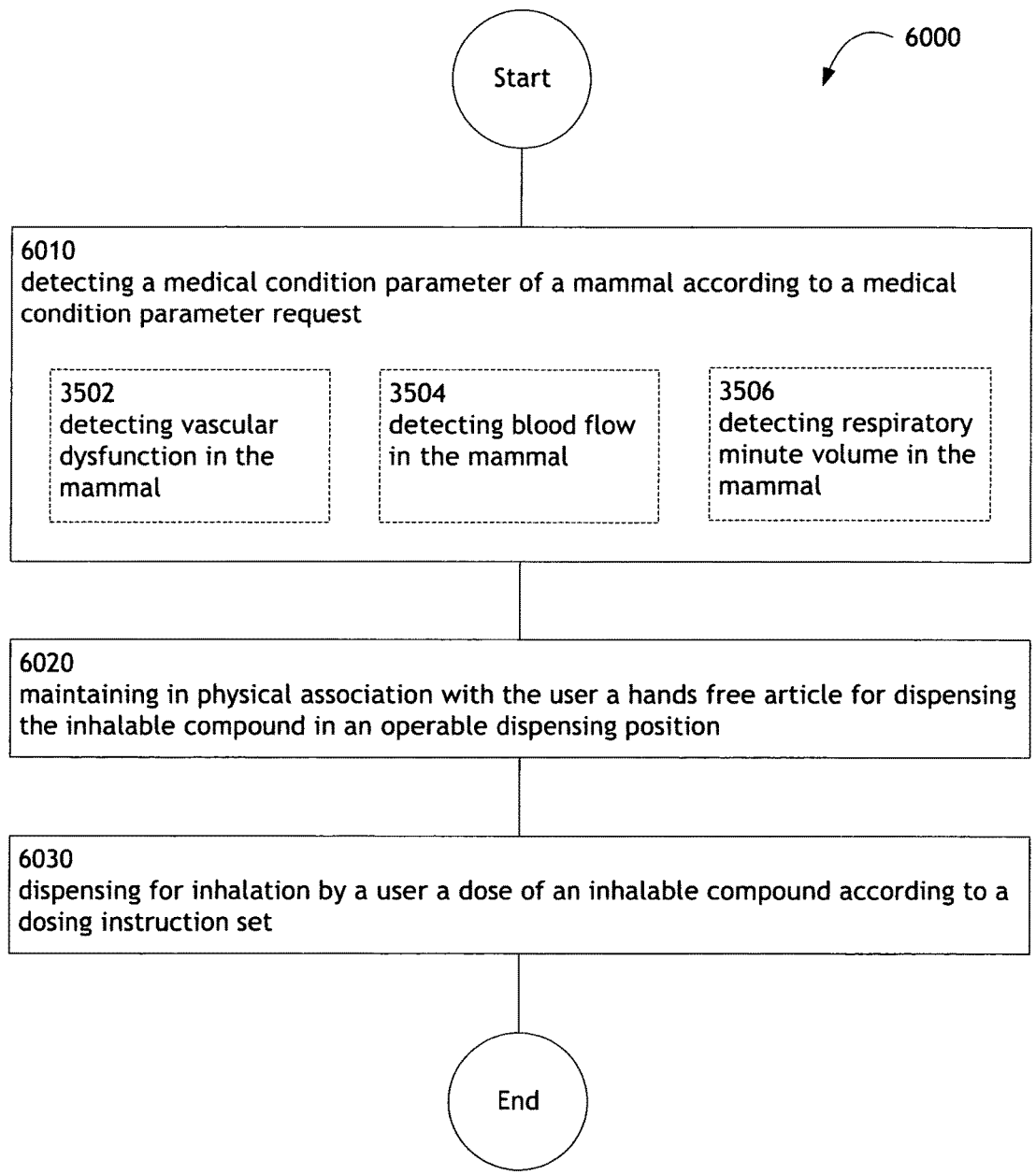
FIG. 35 illustrates an alternative embodiment of the operational flow of FIG. 60.

FIG. 35 illustrates alternative embodiments of the example operational flow 6000 of FIG. 60. FIG. 35 illustrates example embodiments where the operation 6010 may include at least one additional operation. Additional operations may include an operation 3502, an operation 3504, and/or an operation 3506.

The operation 3502 illustrates detecting vascular dysfunction in the mammal. For example, as shown in FIGS. 1A through 1H, the sensor module 170 may be utilized to detect a vascular dysfunction in the subject 102.

The operation 3504 illustrates detecting blood flow in the mammal. For example, as shown in FIGS. 1A through 1H, the sensor module 170 may be utilized to detect blood flow in the subject 102.

The operation 3506 illustrates detecting respiratory minute volume in the mammal. For example, as shown in FIGS. 1A through 1H, the sensor module 170 may be utilized to detect a respiratory volume in the subject 102. In an embodiment, the sensor module 170 may be utilized to detect a sneeze of the subject 102. In an embodiment, the sensor module 170 may be utilized to detect a cough of the subject 102. In an embodiment, the sensor module 170 may be utilized to detect a wheeze of the subject 102. In an embodiment, the sensor module 170 may be utilized to detect a rhonchus of the subject 102. In an embodiment, the sensor module 170 may be utilized to detect a snore of the subject 102. In an embodiment, the sensor module 170 may be utilized to detect a temperature (e.g., a body temperature) of the subject 102. In an embodiment, the sensor module 170 may be utilized to detect an expelled gas from the subject 102, such as a gas exhaled by the subject.

Figure 36:
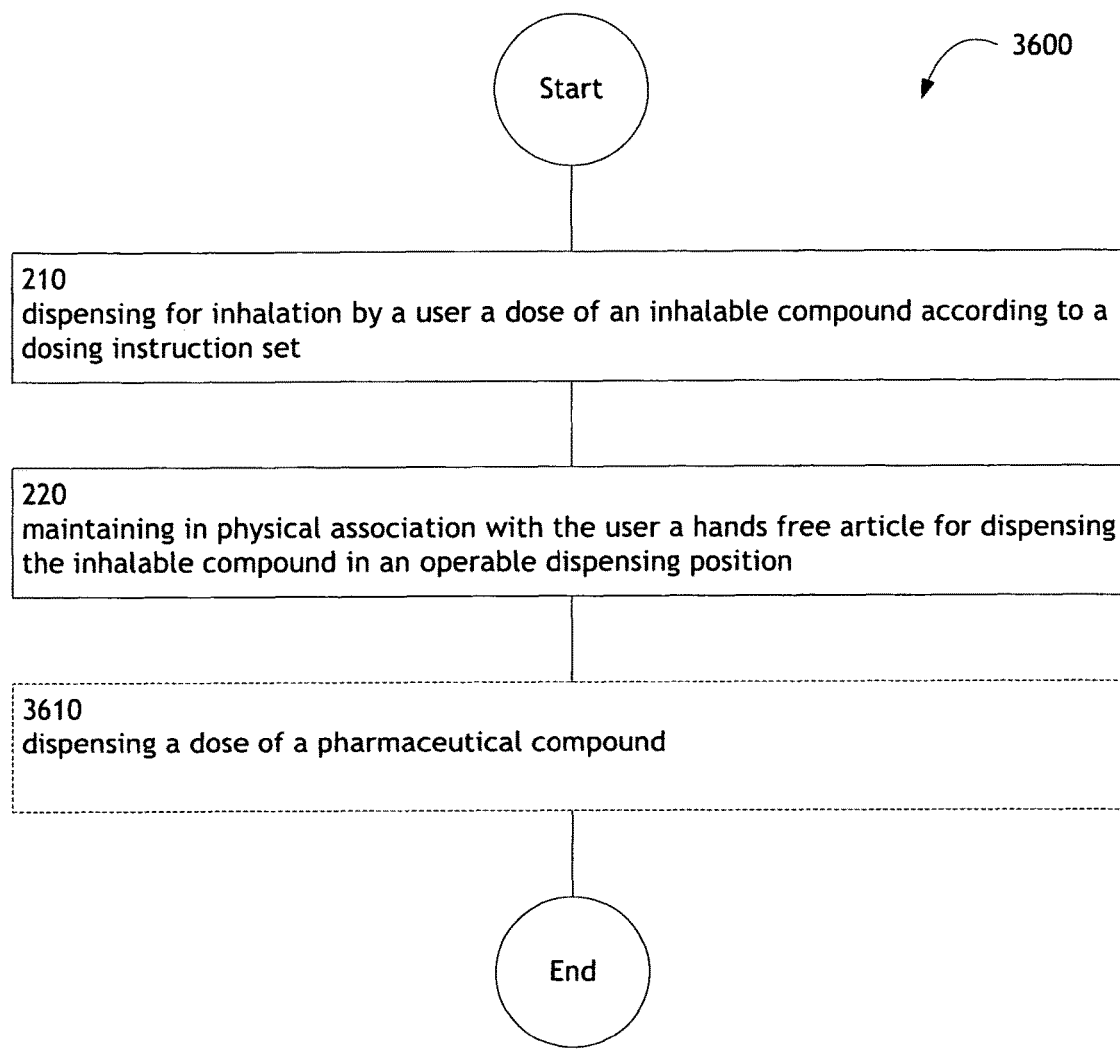
FIG. 36 illustrates an operational flow representing example operations related to maintaining a hands-free article for dispensing an inhalable compound according to a dosing instruction set, where the hands-free article is maintained in an operable dispensing position.

FIG. 36 illustrates an operational flow 3600 representing example operations related to maintaining a hands-free article for dispensing an inhalable compound according to a dosing instruction set, where the hands-free article is maintained in an operable dispensing position. FIG. 36 illustrates an example embodiment where the example operational flow 200 of FIG. 2 may include at least one additional operation. Additional operations may include an operation 3610.

After a start operation, an operation 210, and an operation 220, the operational flow 3600 moves to an operation 3610.

Operation 3610 illustrates dispensing a dose of a pharmaceutical compound. For example, as shown in FIGS. 1A through 1H, the collar 100 may be utilized to dispense a dose 158 of a pharmaceutical compound 178 to the subject 102.

Figure 37:
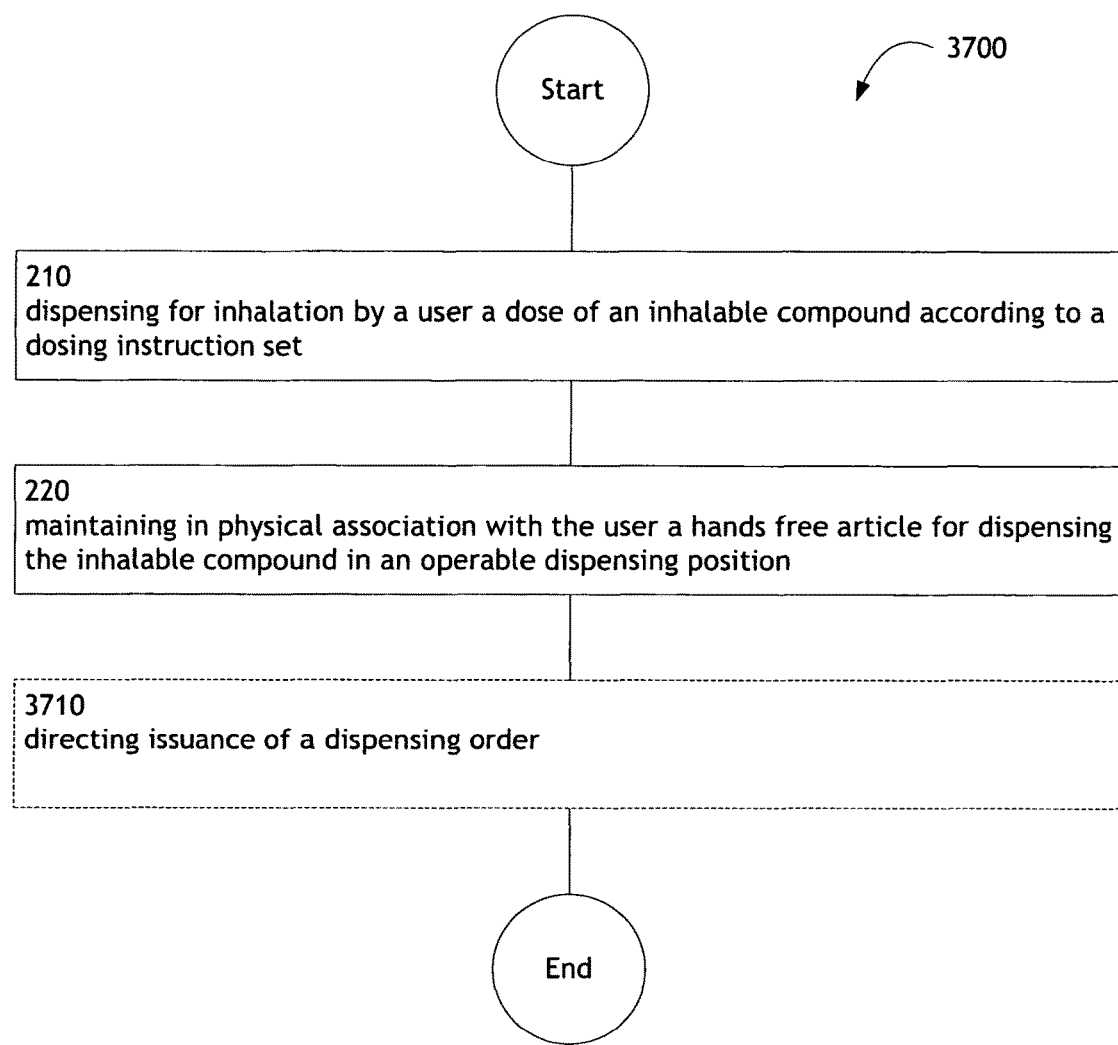
FIG. 37 illustrates an operational flow representing example operations related to maintaining a hands-free article for dispensing an inhalable compound according to a dosing instruction set, where the hands-free article is maintained in an operable dispensing position.

FIG. 37 illustrates an operational flow 3700 representing example operations related to maintaining a hands-free article for dispensing an inhalable compound according to a dosing instruction set, where the hands-free article is maintained in an operable dispensing position. FIG. 37 illustrates an example embodiment where the example operational flow 200 of FIG. 2 may include at least one additional operation. Additional operations may include an operation 3710.

After a start operation, an operation 210, and an operation 220, the operational flow 3700 moves to an operation 3710. Operation 3710 illustrates directing issuance of a dispensing order. For example, as shown in FIGS. 1A through 1H, the processor 156 may direct issuance of a dispensing order (e.g., to the pump 160).

Figure 38:
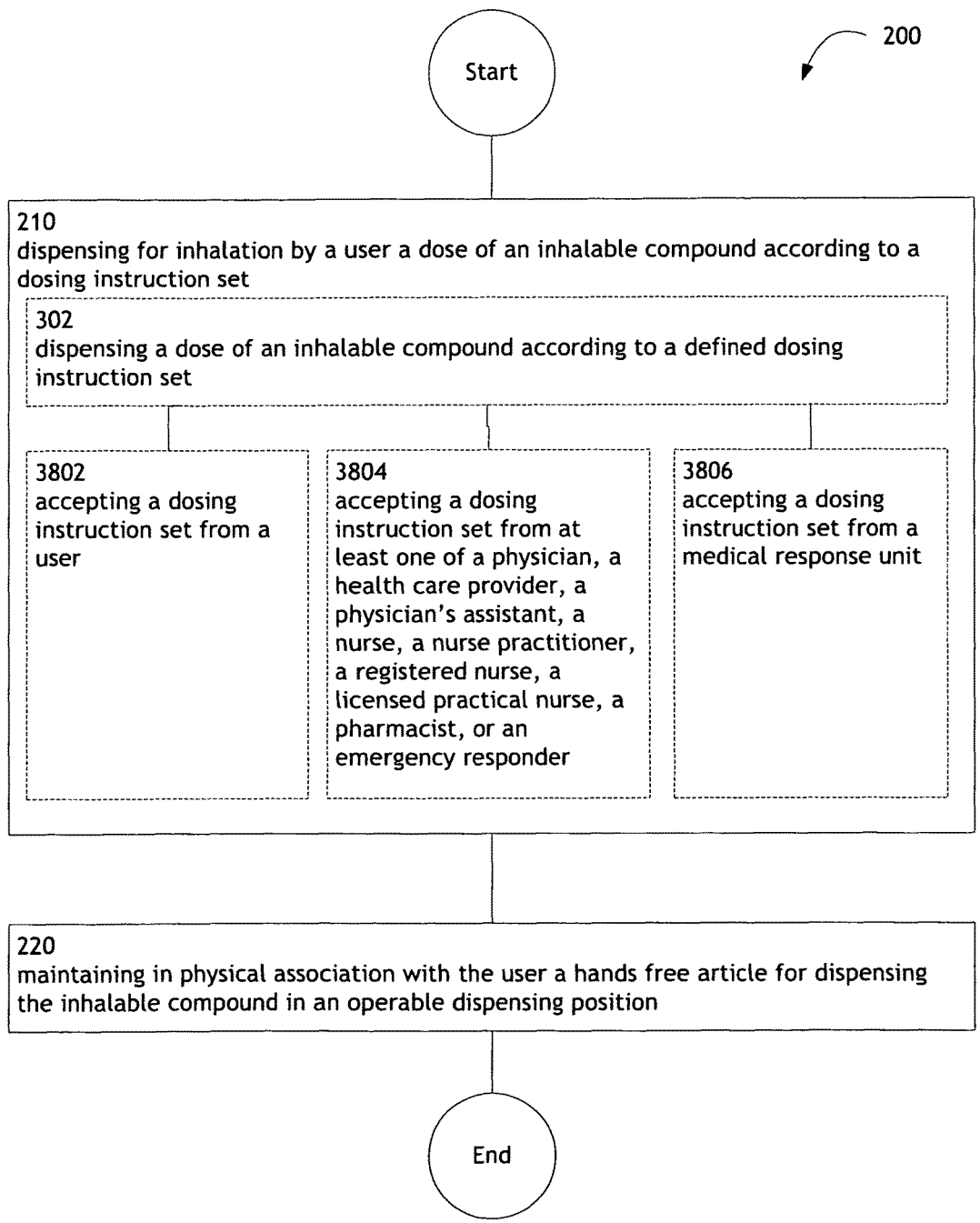
FIG. 38 illustrates an alternative embodiment of the operational flow of FIG. 2.

FIG. 38 illustrates alternative embodiments of the example operational flow 200 of FIG. 2. FIG. 38 illustrates example embodiments where the operation 210 may include at least one additional operation. Additional operations may include an operation 3802, an operation 3804, and/or an operation 3806. Further, the operation 3802 illustrates accepting a dosing instruction set from a user. For example, as shown in FIGS. 1A through 1H, the interface 164 may be utilized to receive a dosing instruction set from a user 166. Further, the operation 3804 illustrates accepting a dosing instruction set from at least one of a physician, a health care provider, a physician's assistant, a nurse, a nurse practitioner, a registered nurse, a licensed practical nurse, a pharmacist, or an emergency responder. For example, as shown in FIGS. 1A through 1H, the interface 164 may be utilized to receive a dosing instruction set from a physician 168. Further, the operation 3806 illustrates accepting a dosing instruction set from a medical response unit. For example, as shown in FIGS. 1A through 1H, the interface 164 may be utilized to receive a dosing instruction set from a medical response unit 192.

Figure 39:
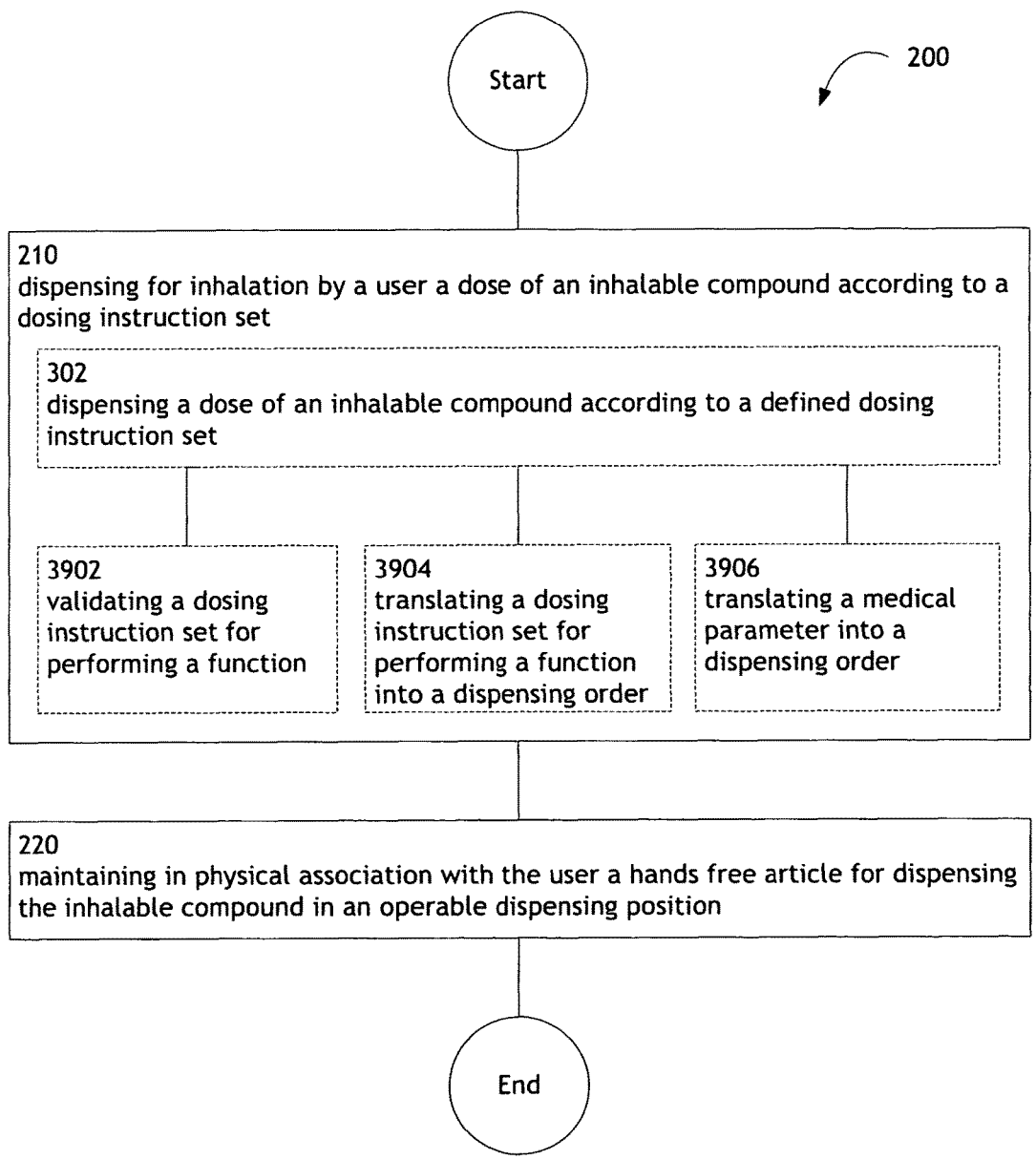
FIG. 39 illustrates an alternative embodiment of the operational flow of FIG. 2.

FIG. 39 illustrates alternative embodiments of the example operational flow 200 of FIG. 2. FIG. 39 illustrates example embodiments where the operation 210 may include at least one additional operation. Additional operations may include an operation 3902, an operation 3904, and/or an operation 3906. Further, the operation 3902 illustrates validating a dosing instruction set for performing a function. For example, as shown in FIGS. 1A through 1H, the processor 156 may be utilized to validate a dosing instruction set (e.g., by check the dosing instruction set against information stored in the memory 154). Further, the operation 3904 illustrates translating a dosing instruction set for performing a function into a dispensing order. For example, as shown in FIGS. 1A through 1H, the processor 156 may be utilized to translate a dosing instruction set into a dispensing order (e.g., by referencing the dosing instruction set to a lookup table stored in the memory 154). Further, the operation 3906 illustrates translating a medical parameter into a dispensing order. For example, as shown in FIGS. 1A through 1H, the processor 156 may be utilized to translate a medical parameter into a dispensing order (e.g., by referencing the medical parameter to a lookup table stored in the memory 154).

Figure 40:
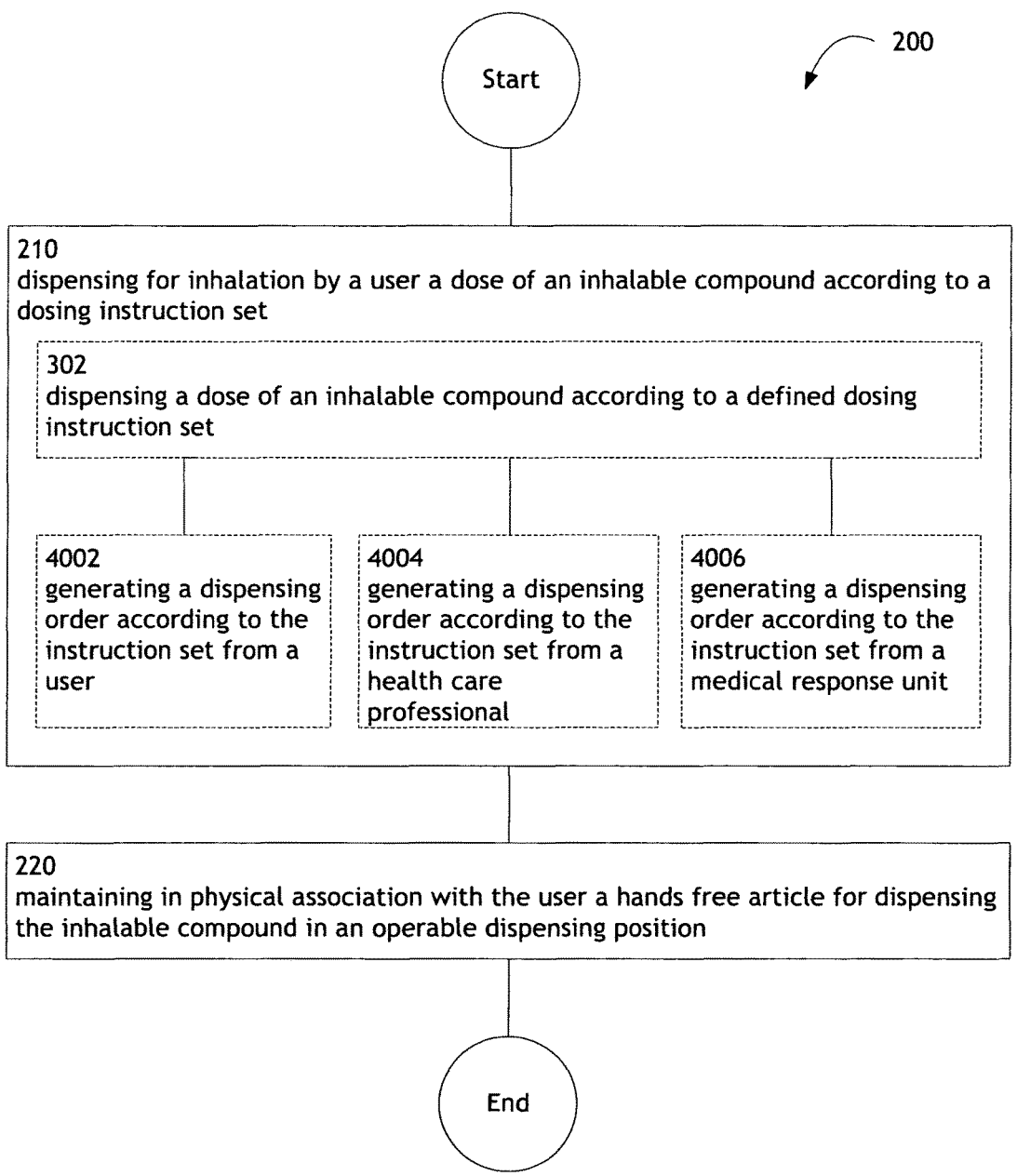
FIG. 40 illustrates an alternative embodiment of the operational flow of FIG. 2.

FIG. 40 illustrates alternative embodiments of the example operational flow 200 of FIG. 2. FIG. 40 illustrates example embodiments where the operation 210 may include at least one additional operation. Additional operations may include an operation 4002, an operation 4004, and/or an operation 4006. Further, the operation 4002 illustrates generating a dispensing order according to the instruction set from a user. For example, as shown in FIGS. 1A through 1H, the processor 156 may be utilized to generate a dispensing order according to an instruction set from a user 166 stored in the memory 154. Further, the operation 4004 illustrates generating a dispensing order according to the instruction set from a health care professional. For example, as shown in FIGS. 1A through 1H, the processor 156 may be utilized to generate a dispensing order according to an instruction set from a physician 168 stored in the memory 154. Further, the operation 4006 illustrates generating a dispensing order according to the instruction set from a medical response unit. For example, as shown in FIGS. 1A through 1H, the processor 156 may be utilized to generate a dispensing order according to an instruction set from a medical response unit 192 stored in the memory 154.

Figure 41:
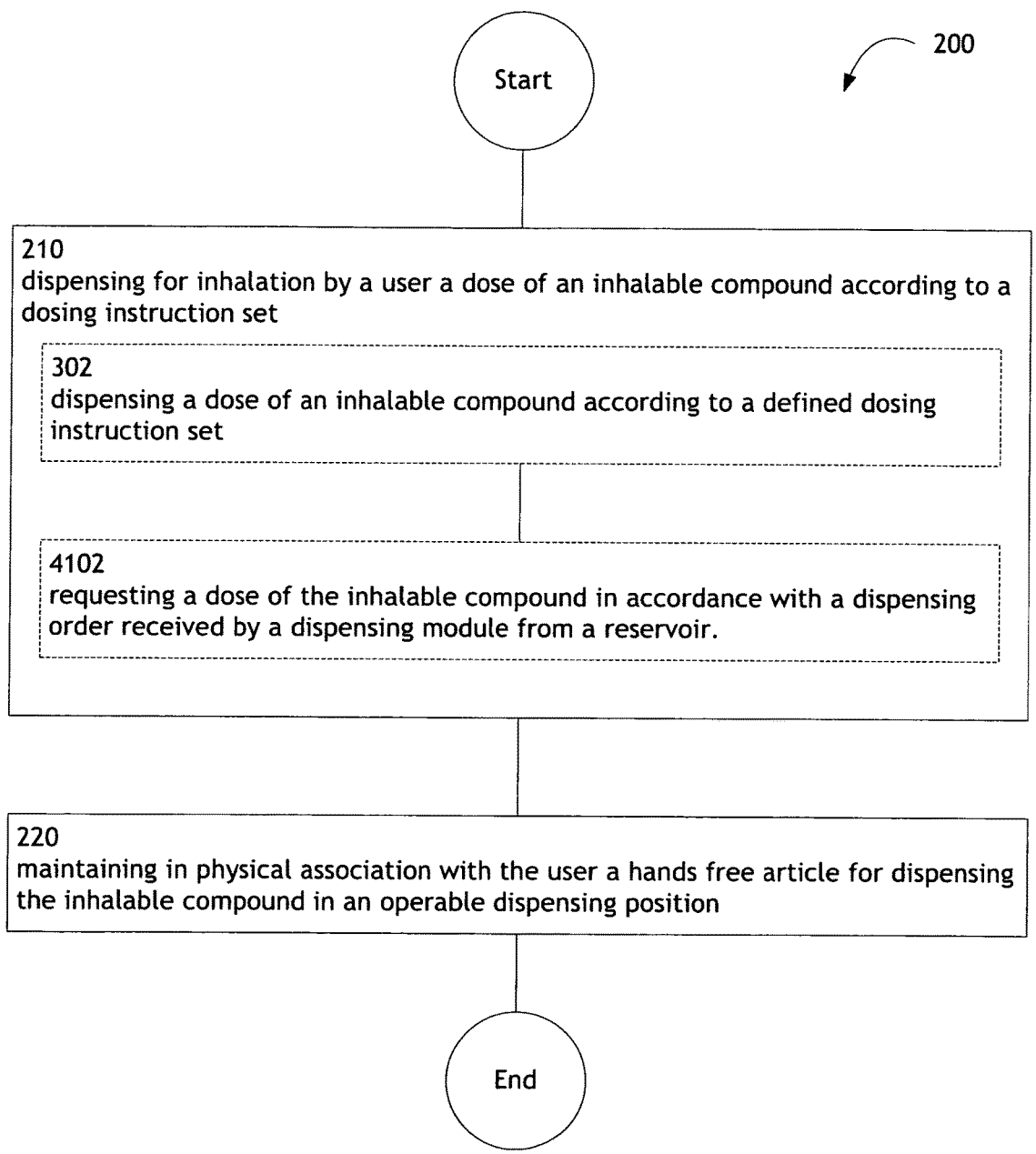
FIG. 41 illustrates an alternative embodiment of the operational flow of FIG. 2.

FIG. 41 illustrates alternative embodiments of the example operational flow 200 of FIG. 2. FIG. 41 illustrates example embodiments where the operation 210 may include at least one additional operation. Additional operations may include an operation 4102. Further, the operation 4102 illustrates requesting a dose of the inhalable compound in accordance with a dispensing order received by a dispensing module from a reservoir. For example, as shown in FIGS. 1A through 1H, the dispensing module 128 may receive a request from the reservoir 180 for a dose of the compound 104.

Figure 42:
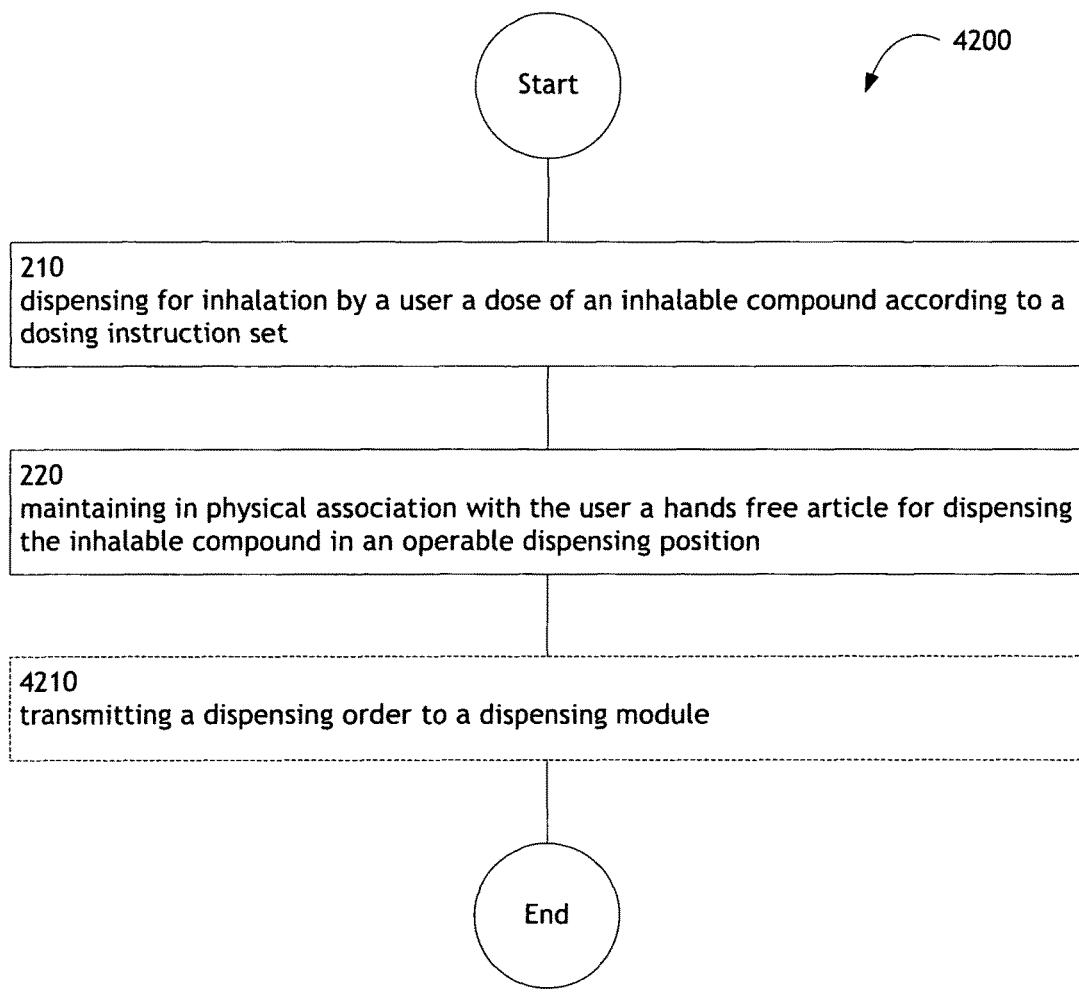
FIG. 42 illustrates an operational flow representing example operations related to maintaining a hands-free article for dispensing an inhalable compound according to a dosing instruction set, where the hands-free article is maintained in an operable dispensing position.

FIG. 42 illustrates an operational flow 4200 representing example operations related to maintaining a hands-free article for dispensing an inhalable compound according to a dosing instruction set, where the hands-free article is maintained in an operable dispensing position. FIG. 42 illustrates an example embodiment where the example operational flow 200 of FIG. 2 may include at least one additional operation. Additional operations may include an operation 4210.

After a start operation, an operation 210, and an operation 220, the operational flow 4200 moves to an operation 4210. Operation 4210 illustrates transmitting a dispensing order to a dispensing module. For example, as shown in FIGS. 1A through 1H, the processor 156 may transmit a dispensing order to the dispensing module 128 (e.g., to the reservoir 180).

Figure 43:
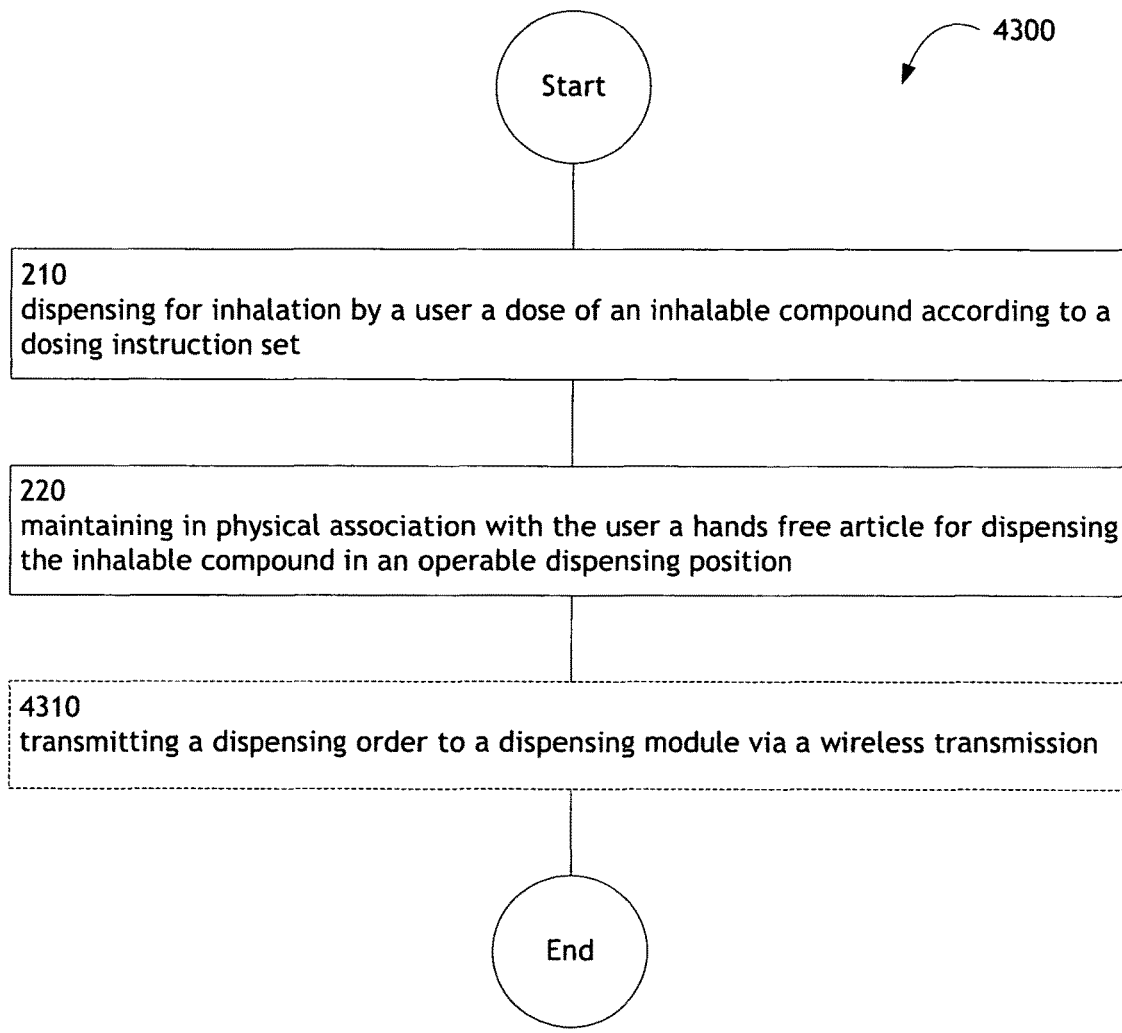
FIG. 43 illustrates an operational flow representing example operations related to maintaining a hands-free article for dispensing an inhalable compound according to a dosing instruction set, where the hands-free article is maintained in an operable dispensing position.

FIG. 43 illustrates an operational flow 4300 representing example operations related to maintaining a hands-free article for dispensing an inhalable compound according to a dosing instruction set, where the hands-free article is maintained in an operable dispensing position. FIG. 43 illustrates an example embodiment where the example operational flow 200 of FIG. 2 may include at least one additional operation. Additional operations may include an operation 4310.

After a start operation, an operation 210, and an operation 220, the operational flow 4300 moves to an operation 4310. Operation 4310 illustrates transmitting a dispensing order to a dispensing module via a wireless transmission. For example, as shown in FIGS. 1A through 1H, the dispensing module 128 may receive a dispensing order from a physician 168 via a wireless transmission received by the interface 164.

FIG. 44 illustrates an operational flow 4400 representing example operations related to maintaining a hands-free article for dispensing an inhalable compound according to a dosing instruction set, where the hands-free article is maintained in an operable dispensing position. FIG. 44 illustrates an example embodiment where the example operational flow 200 of FIG. 2 may include at least one additional operation. Additional operations may include an operation 4410.

After a start operation, an operation 210, and an operation 220, the operational flow 4400 moves to an operation 4410. Operation 4410 illustrates transmitting a dispensing order to a dispensing module via an optical transmission. For example, as shown in FIGS. 1A through 1H, the dispensing module 128 may receive a dispensing order from a physician 168 via an optical transmission received by the interface 164.

Figure 45:
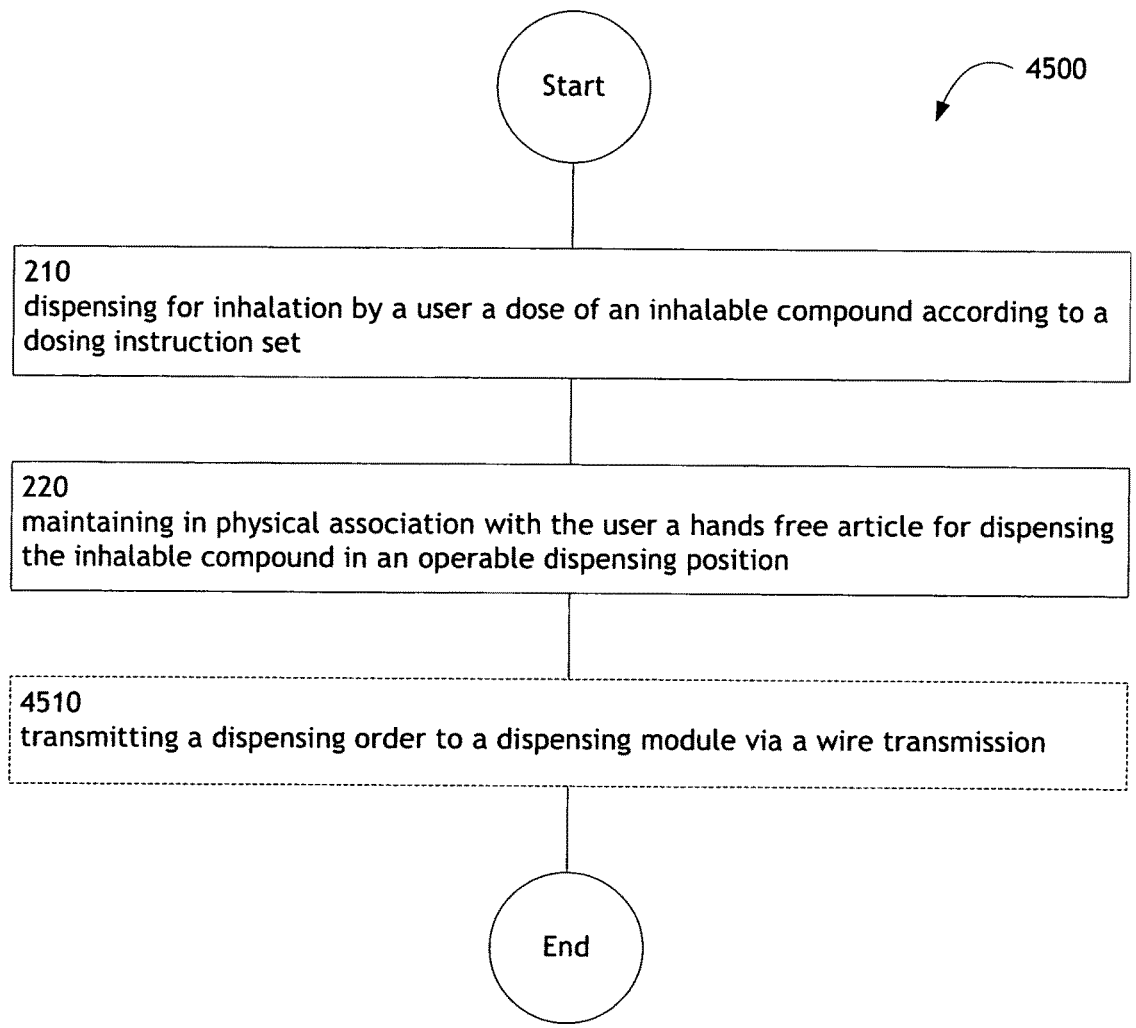
FIG. 45 illustrates an operational flow representing example operations related to maintaining a hands-free article for dispensing an inhalable compound according to a dosing instruction set, where the hands-free article is maintained in an operable dispensing position.

FIG. 45 illustrates an operational flow 4500 representing example operations related to maintaining a hands-free article for dispensing an inhalable compound according to a dosing instruction set, where the hands-free article is maintained in an operable dispensing position. FIG. 45 illustrates an example embodiment where the example operational flow 200 of FIG. 2 may include at least one additional operation. Additional operations may include an operation 4510.

After a start operation, an operation 210, and an operation 220, the operational flow 4500 moves to an operation 4510. Operation 4510 illustrates transmitting a dispensing order to a dispensing module via a wire transmission. For example, as shown in FIGS. 1A through 1H, the dispensing module 128 may receive a dispensing order from a physician 168 via an wire transmission received by the interface 164.

Figure 46:
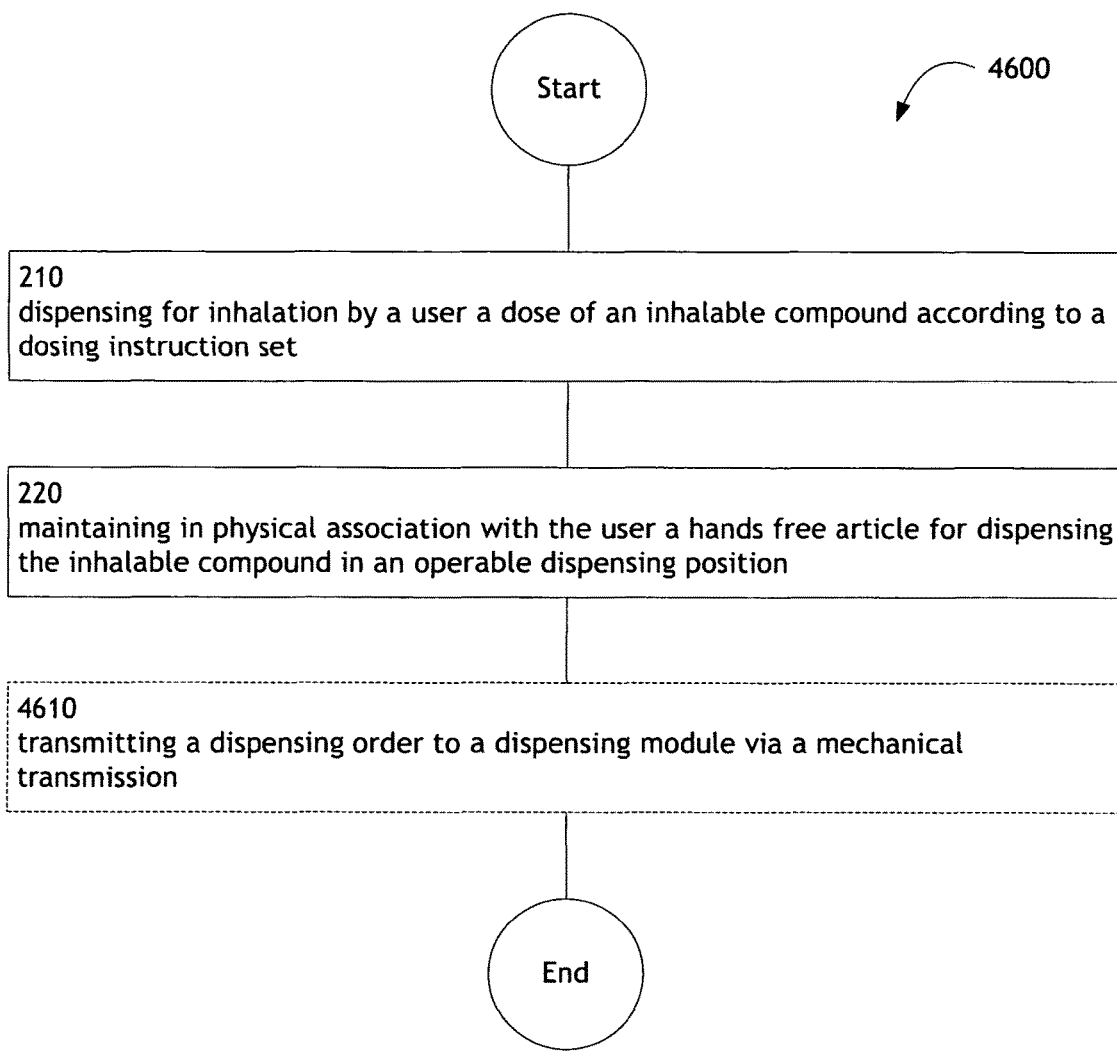
FIG. 46 illustrates an operational flow representing example operations related to maintaining a hands-free article for dispensing an inhalable compound according to a dosing instruction set, where the hands-free article is maintained in an operable dispensing position.

FIG. 46 illustrates an operational flow 4600 representing example operations related to maintaining a hands-free article for dispensing an inhalable compound according to a dosing instruction set, where the hands-free article is maintained in an operable dispensing position. FIG. 46 illustrates an example embodiment where the example operational flow 200 of FIG. 2 may include at least one additional operation. Additional operations may include an operation 4610.

After a start operation, an operation 210, and an operation 220, the operational flow 4600 moves to an operation 4610. Operation 4610 illustrates transmitting a dispensing order to a dispensing module via a mechanical transmission. For example, as shown in FIGS. 1A through 1H, the dispensing module 128 may receive a dispensing order from a physician 168 via a mechanical transmission received by the interface 164.

Figure 47:
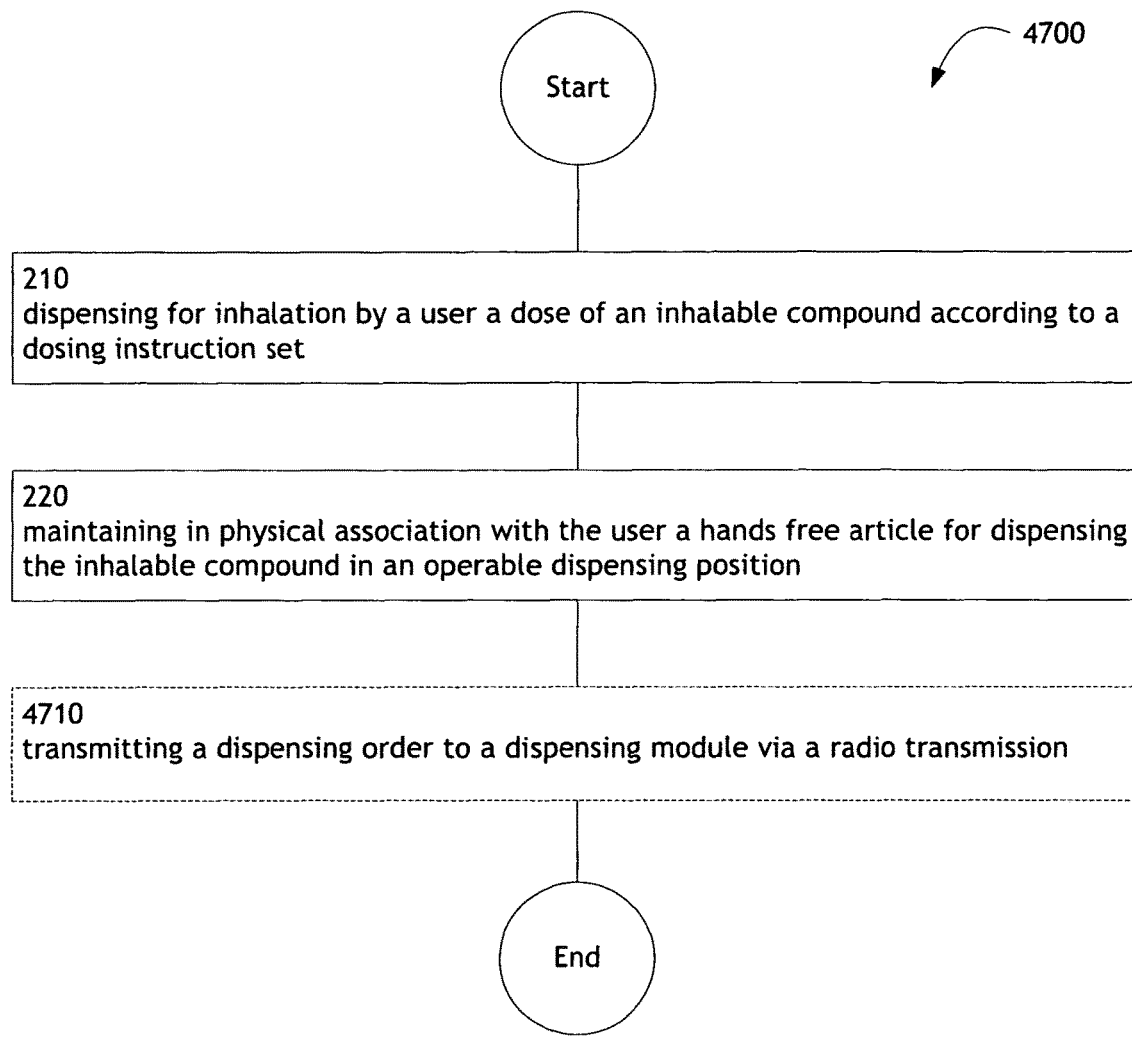
FIG. 47 illustrates an operational flow representing example operations related to maintaining a hands-free article for dispensing an inhalable compound according to a dosing instruction set, where the hands-free article is maintained in an operable dispensing position.

FIG. 47 illustrates an operational flow 4700 representing example operations related to maintaining a hands-free article for dispensing an inhalable compound according to a dosing instruction set, where the hands-free article is maintained in an operable dispensing position. FIG. 47 illustrates an example embodiment where the example operational flow 200 of FIG. 2 may include at least one additional operation. Additional operations may include an operation 4710.

After a start operation, an operation 210, and an operation 220, the operational flow 4700 moves to an operation 4710. Operation 4710 illustrates transmitting a dispensing order to a dispensing module via a radio transmission. For example, as shown in FIGS. 1A through 1H, the dispensing module 128 may receive a dispensing order from a physician 168 via a radio transmission received by the interface 164.

Figure 48:
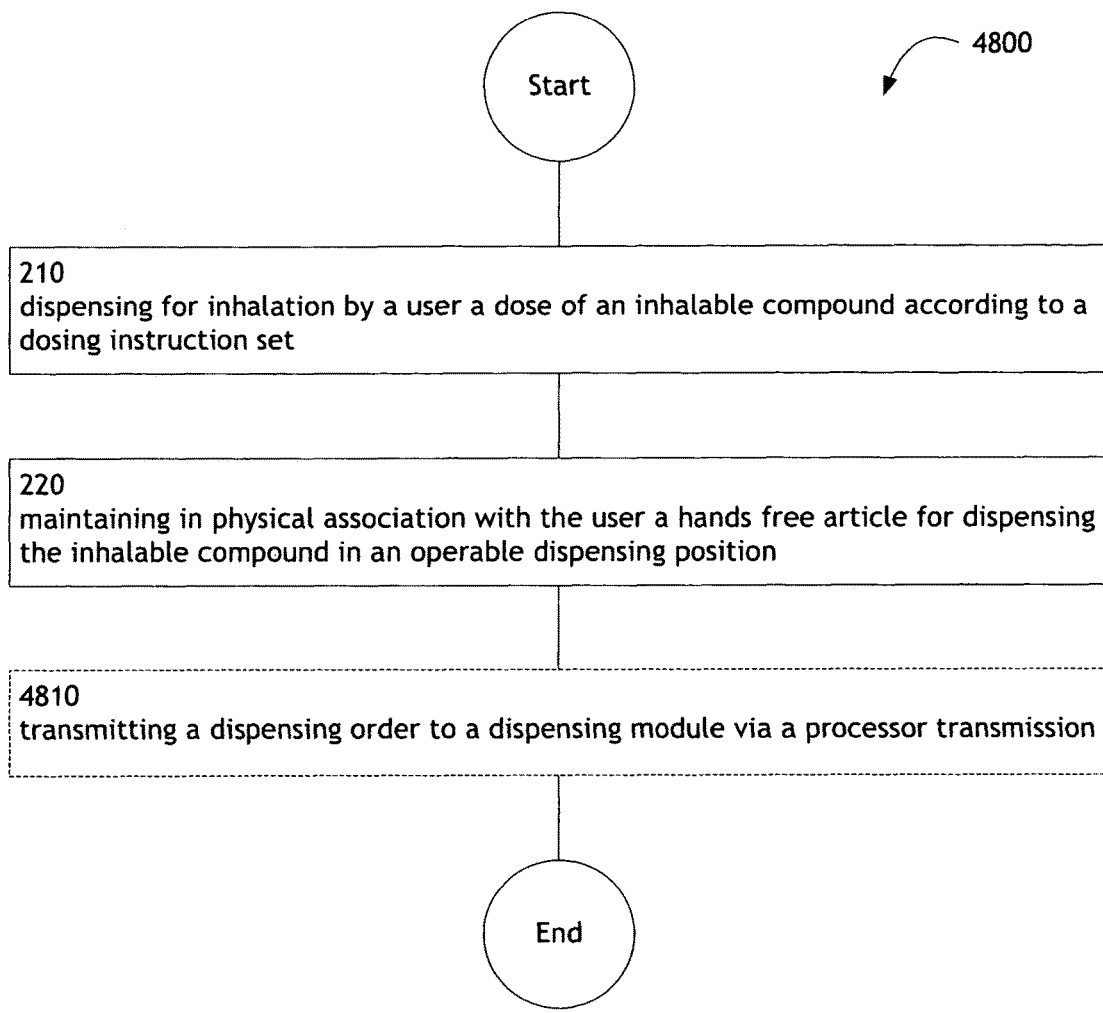
FIG. 48 illustrates an operational flow representing example operations related to maintaining a hands-free article for dispensing an inhalable compound according to a dosing instruction set, where the hands-free article is maintained in an operable dispensing position.

FIG. 48 illustrates an operational flow 4800 representing example operations related to maintaining a hands-free article for dispensing an inhalable compound according to a dosing instruction set, where the hands-free article is maintained in an operable dispensing position. FIG. 48 illustrates an example embodiment where the example operational flow 200 of FIG. 2 may include at least one additional operation. Additional operations may include an operation 4810.

After a start operation, an operation 210, and an operation 220, the operational flow 4800 moves to an operation 4810. Operation 4810 illustrates transmitting a dispensing order to a dispensing module via a processor transmission. For example, as shown in FIGS. 1A through 1H, the dispensing module 128 may receive a dispensing order from the processor 156.

Figure 49:
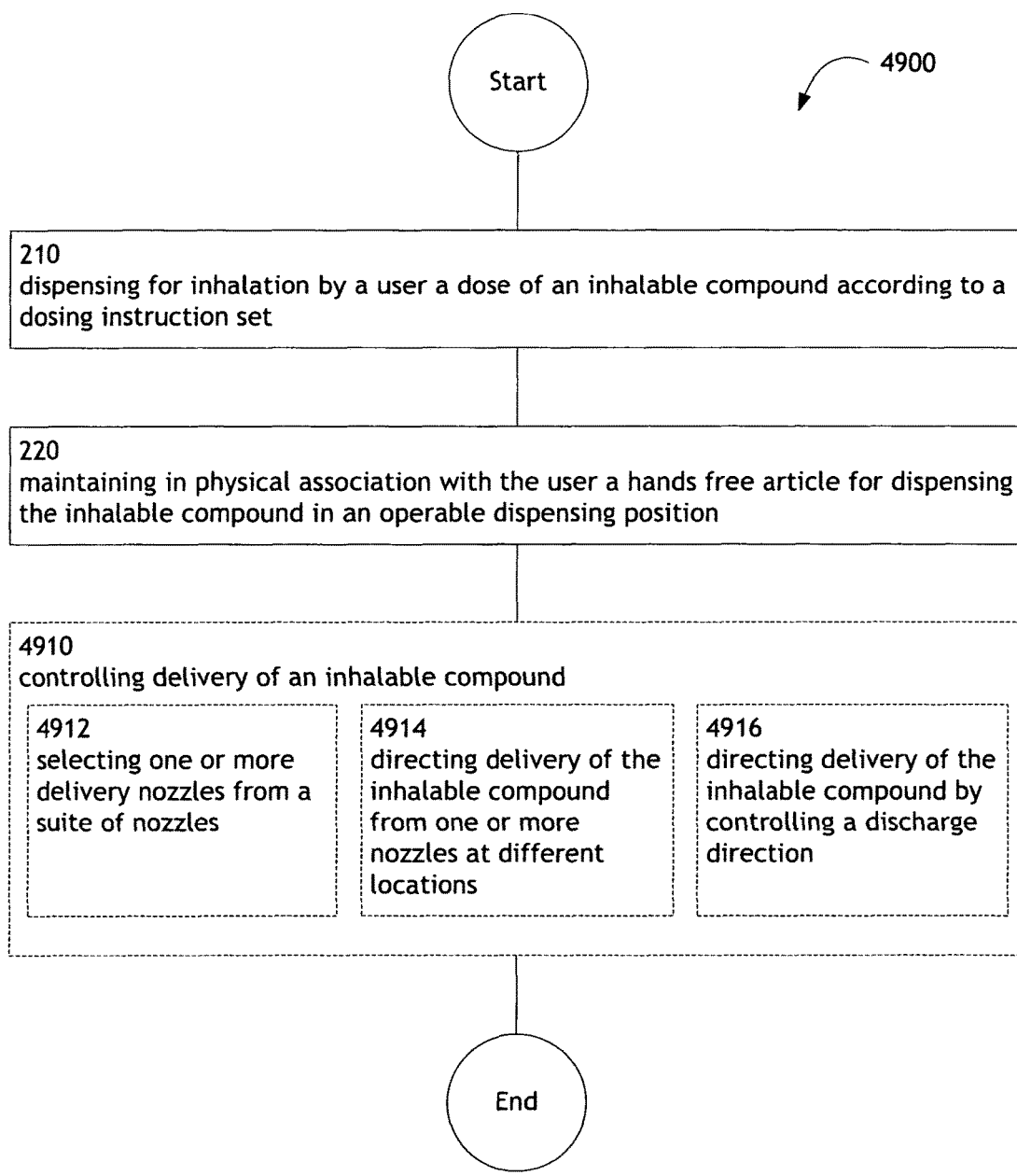
FIG. 49 illustrates an operational flow representing example operations related to maintaining a hands-free article for dispensing an inhalable compound according to a dosing instruction set, where the hands-free article is maintained in an operable dispensing position.
Figure 50:
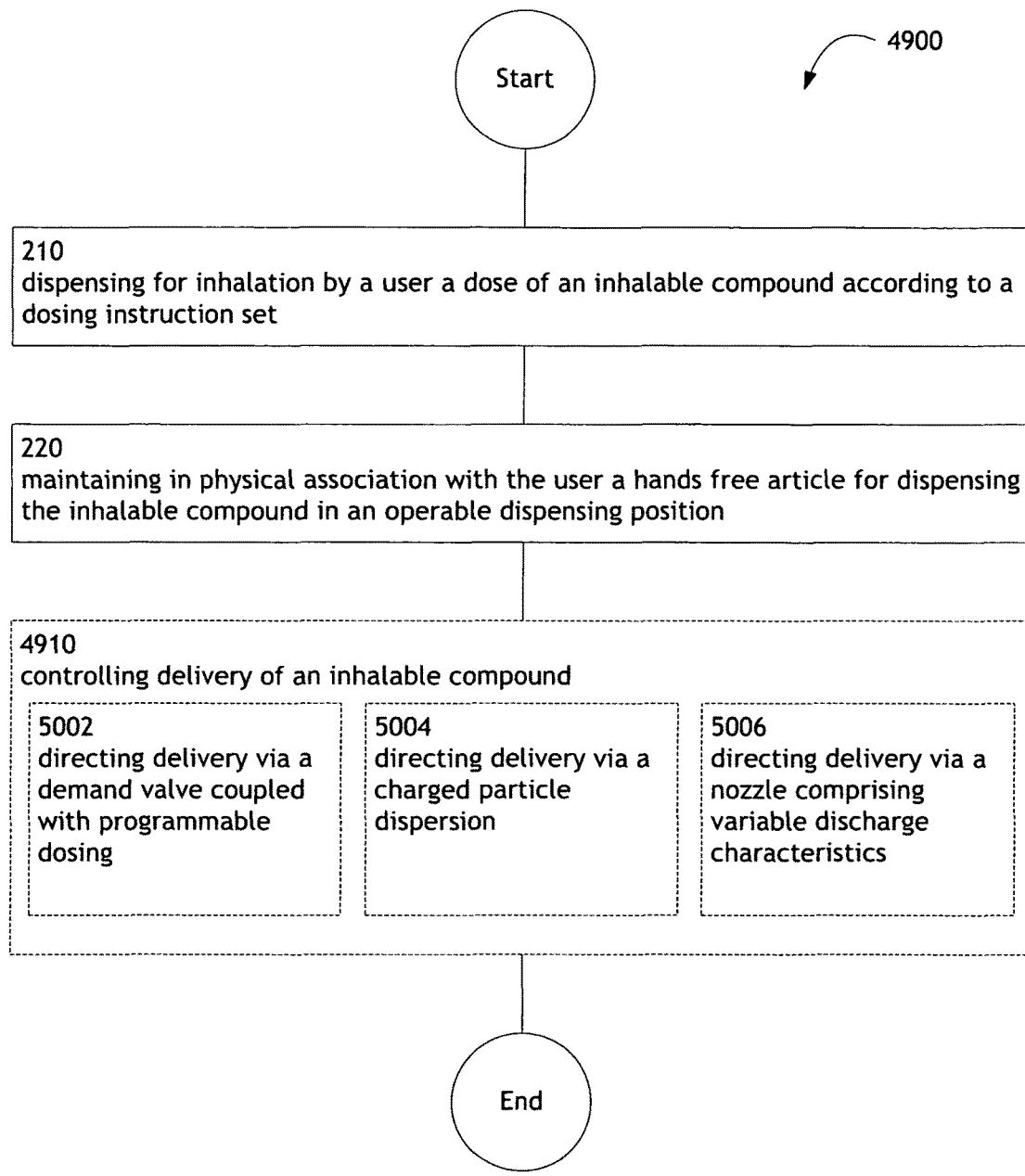
FIG. 50 illustrates an alternative embodiment of the operational flow of FIG. 49.
Figure 51:
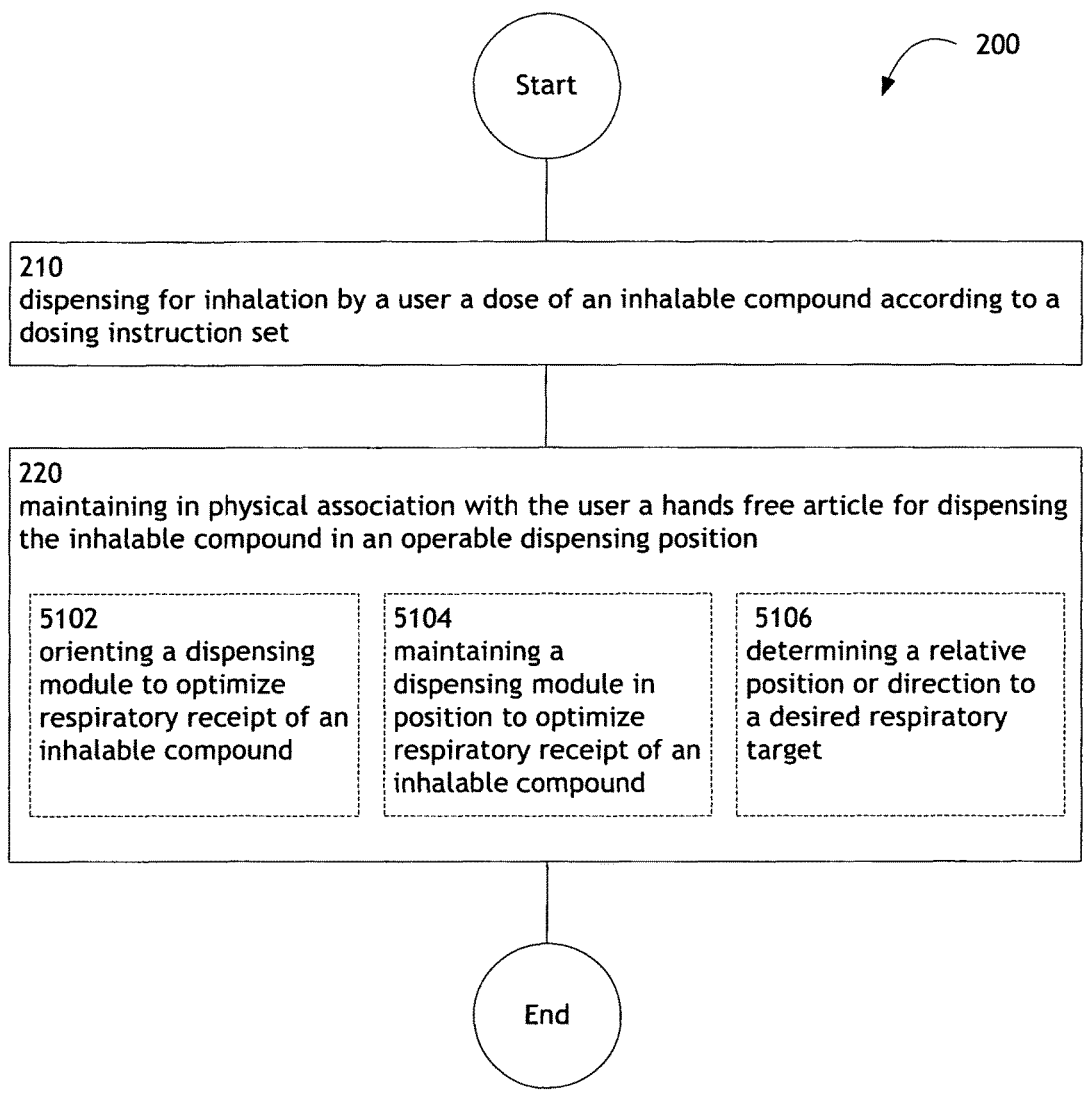
FIG. 51 illustrates an alternative embodiment of the operational flow of FIG. 2.

FIG. 49 illustrates an operational flow 4900 representing example operations related to maintaining a hands-free article for dispensing an inhalable compound according to a dosing instruction set, where the hands-free article is maintained in an operable dispensing position. FIG. 49 illustrates an example embodiment where the example operational flow 200 of FIG. 2 may include at least one additional operation. Additional operations may include an operation 4910, an operation 4912, an operation 4914, and/or an operation 4916.

After a start operation, an operation 210, and an operation 220, the operational flow 4900 moves to an operation 4910. Operation 4910 illustrates controlling delivery of an inhalable compound. For example, as shown in FIGS. 1A through 1H, the demand valve 152 may be utilized to control delivery of the compound 104.

The operation 4912 illustrates selecting one or more delivery nozzles from a suite of nozzles. For example, as shown in FIGS. 1A through 1H, the second nozzle 150 may be selected from the suite of nozzles 148.

The operation 4914 illustrates directing delivery of the inhalable compound from one or more nozzles at different locations. For example, as shown in FIGS. 1A through 1H, the compound 104 may be delivered from the first nozzle 130 or the second nozzle 150.

The operation 4916 illustrates directing delivery of the inhalable compound by controlling a discharge direction. For example, as shown in FIGS. 1A through 1H, the direction of the subject's nose 132 may be calculated. Then, a discharge direction for the dispensing module 128 may be controlled for optimizing delivery of the compound 104.

FIG. 50 illustrates alternative embodiments of the example operational flow 4900 of FIG. 49. FIG. 50 illustrates example embodiments where the operation 4910 may include at least one additional operation. Additional operations may include an operation 5002, an operation 5004, and/or an operation 5006.

The operation 5002 illustrates directing delivery via a demand valve coupled with programmable dosing. For example, as shown in FIGS. 1A through 1H, the demand valve 152 may be operatively configured to dispense the compound 104 in accordance with a dosing schedule stored in the memory 154.

The operation 5004 illustrates directing delivery via a charged particle dispersion. For example, as shown in FIGS. 1A through 1H, the dispensing module 128 may dispense the compound 104 as a charged particle dispersion.

The operation 5006 illustrates directing delivery via a nozzle comprising variable discharge characteristics. For example, as shown in FIGS. 1A through 1H, the first nozzle 130, the second nozzle 150, or the suite of nozzles 148 may include nozzles having variable discharge characteristics, such as directional, volumetric, spray area, or other characteristics.

FIG. 51 illustrates alternative embodiments of the example operational flow 200 of FIG. 2. FIG. 51 illustrates example embodiments where the operation 220 may include at least one additional operation. Additional operations may include an operation 5102, an operation 5104, and/or an operation 5106.

The operation 5102 illustrates orienting a dispensing module to optimize respiratory receipt of an inhalable compound. For example, as shown in FIGS. 1A through 1H, the dispensing module 128 may be maintained in an optimal position for optimizing delivery of the compound 104 to the subject 102.

The operation 5104 illustrates maintaining a dispensing module in position to optimize respiratory receipt of an inhalable compound. For example, as shown in FIGS. 1A through 1H, the orientation of the nozzle 130 may be maintained in the direction determined for the subject's nose 132.

The operation 5106 illustrates determining a relative position or direction to a desired respiratory target. For example, as shown in FIGS. 1A through 1H, the direction to the subject's nose 132 may be calculated.

Figure 52:
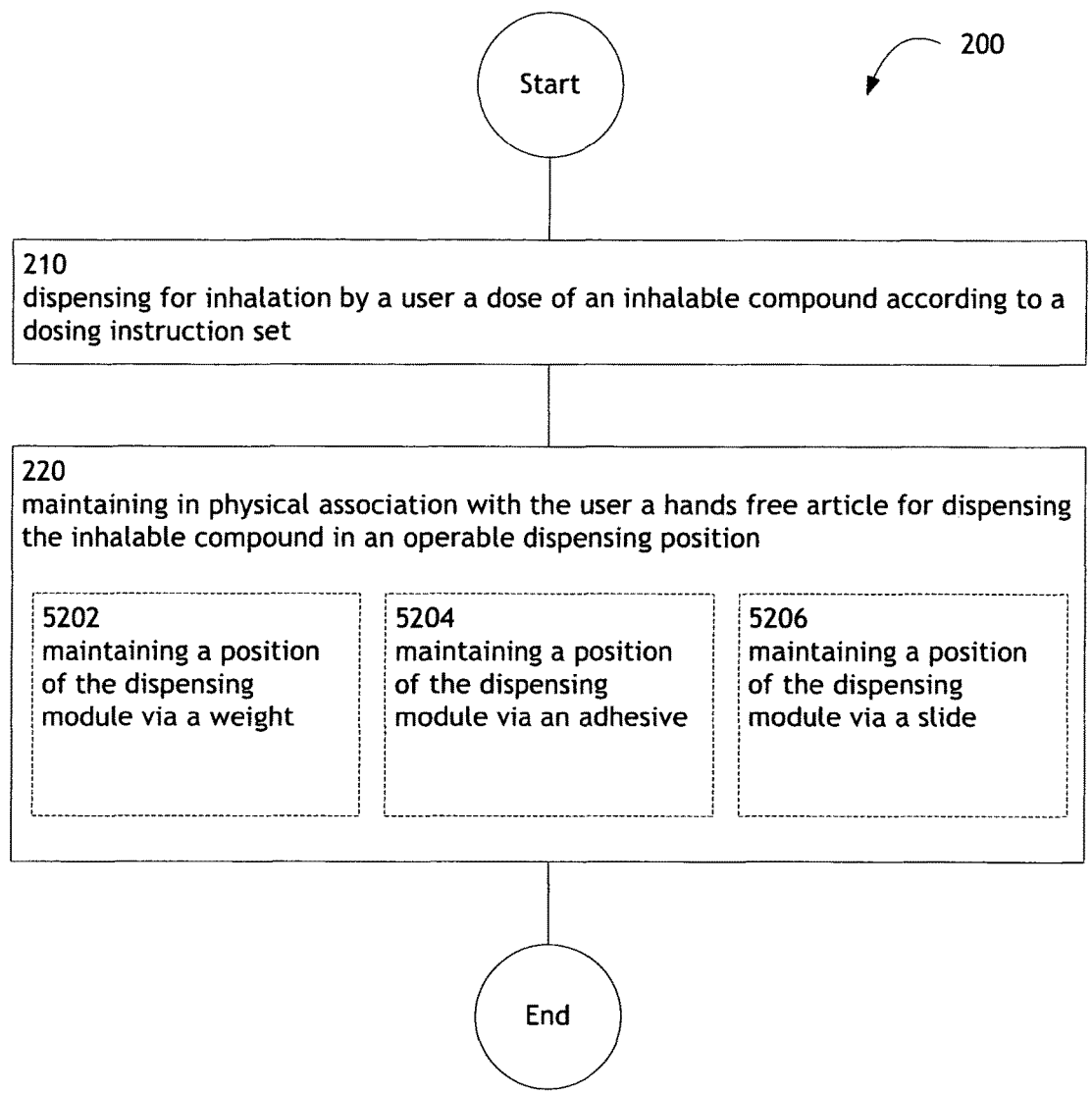
FIG. 52 illustrates an alternative embodiment of the operational flow of FIG. 2.

FIG. 52 illustrates alternative embodiments of the example operational flow 200 of FIG. 2. FIG. 52 illustrates example embodiments where the operation 220 may include at least one additional operation. Additional operations may include an operation 5202, an operation 5204, and/or an operation 5206.

The operation 5202 illustrates maintaining a position of the dispensing module via a weight. For example, as shown in FIGS. 1A through 1H, the position of the dispensing module 128 may be maintained via a weight 136.

The operation 5204 illustrates maintaining a position of the dispensing module via an adhesive. For example, as shown in FIGS. 1A through 1H, the position of the dispensing module may be maintained via an adhesive 138.

The operation 5206 illustrates maintaining a position of the dispensing module via a slide. For example, as shown in FIGS. 1A through 1H, the position of the dispensing module 128 may be maintained via a slide 140.

Figure 53:
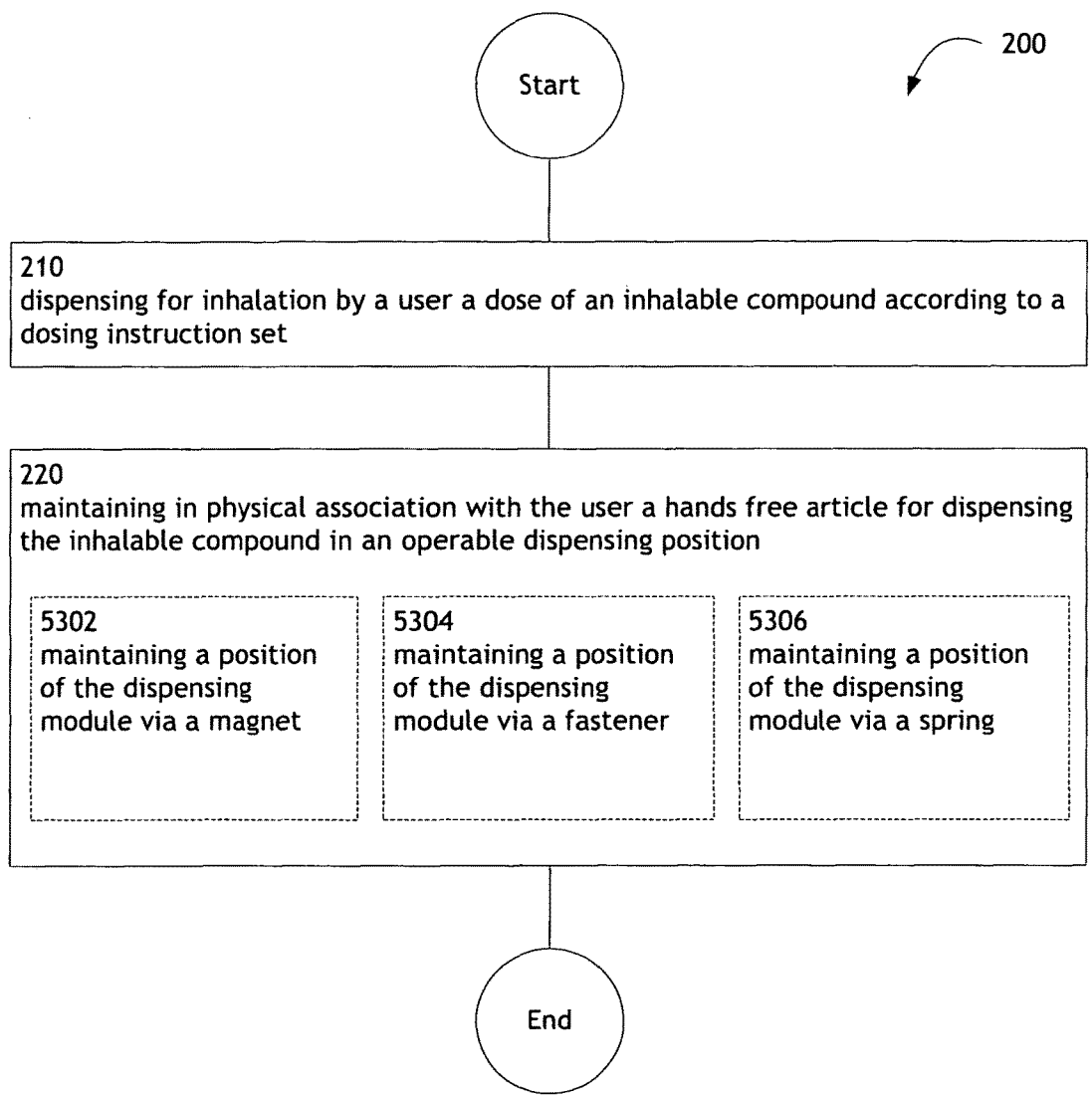
FIG. 53 illustrates an alternative embodiment of the operational flow of FIG. 2.

FIG. 53 illustrates alternative embodiments of the example operational flow 200 of FIG. 2. FIG. 53 illustrates example embodiments where the operation 220 may include at least one additional operation. Additional operations may include an operation 5302, an operation 5304, and/or an operation 5306.

The operation 5302 illustrates maintaining a position of the dispensing module via a magnet. For example, as shown in FIGS. 1A through 1H, the position of the dispensing module 128 may be maintained via a magnet 142.

The operation 5304 illustrates maintaining a position of the dispensing module via a fastener. For example, as shown in FIGS. 1A through 1H, the position of the dispensing module 128 may be maintained via a fastener 144 (e.g., a button or a snap).

The operation 5306 illustrates maintaining a position of the dispensing module via a spring. For example, as shown in FIG. 1A through 1H, the position of the dispensing module 128 may be maintained via a spring 146.

FIG. 54 illustrates an operational flow 5400 representing example operations related to maintaining a hands-free article for dispensing an inhalable compound according to a dosing instruction set, where the hands-free article is maintained in an operable dispensing position. FIG. 54 illustrates an example embodiment where the example operational flow 200 of FIG. 2 may include at least one additional operation. Additional operations may include an operation 5410, an operation 5412, an operation 5414, and/or an operation 5416.

After a start operation, an operation 210, and an operation 220, the operational flow 5400 moves to an operation 5410. Operation 5410 illustrates dispensing a tracer compound in association with the inhalable compound. For example, as shown in FIGS. 1A through 1H, the compound 104 may comprise an inhalable compound 52 and one or more tracer compounds.

The operation 5412 illustrates dispensing a visual tracer compound. For example, as shown in FIGS. 1A through 1H, the compound 104 may include a visual tracer 54.

The operation 5414 illustrates dispensing an olfactory tracer compound. For example, as shown in FIGS. 1A through 1H, the compound 104 may include an olfactory tracer 56.

The operation 5416 illustrates dispensing a tastable tracer compound. For example, as shown in FIGS. 1A through 1H, the compound 104 may include a tastable tracer 58.

Figure 55:
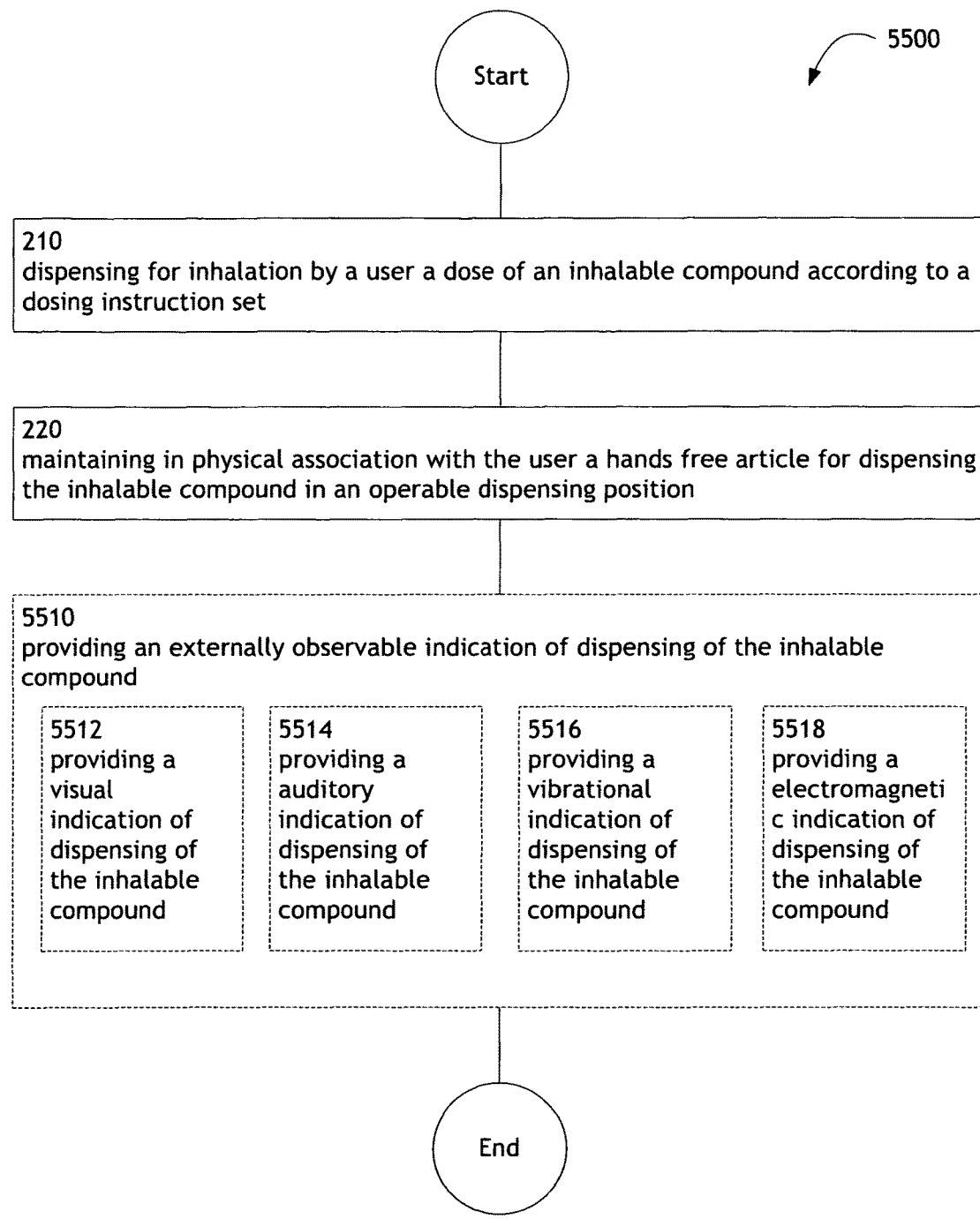
FIG. 55 illustrates an operational flow representing example operations related to maintaining a hands-free article for dispensing an inhalable compound according to a dosing instruction set, where the hands-free article is maintained in an operable dispensing position.

FIG. 55 illustrates an operational flow 5500 representing example operations related to maintaining a hands-free article for dispensing an inhalable compound according to a dosing instruction set, where the hands-free article is maintained in an operable dispensing position. FIG. 55 illustrates an example embodiment where the example operational flow 200 of FIG. 2 may include at least one additional operation. Additional operations may include an operation 5510, an operation 5512, an operation 5514, an operation 5516, and/or an operation 5518.

After a start operation, an operation 210, and an operation 220, the operational flow 5500 moves to an operation 5510. Operation 5510 illustrates providing an externally observable indication of dispensing of the inhalable compound. For example, as shown in FIGS. 1A through 1H, the collar 100 may include a visual indicator 196 for indicating dispensing of the inhalable compound.

The operation 5512 illustrates providing a visual indication of dispensing of the inhalable compound. For example, as shown in FIGS. 1A through 1H, the collar 100 may include the visual indicator 196 for indicating dispensing of the inhalable compound.

The operation 5514 illustrates providing a auditory indication of dispensing of the inhalable compound. For example, as shown in FIGS. 1A through 1H, the collar 100 may include an audible indicator 198.

The operation 5516 illustrates providing a vibrational indication of dispensing of the inhalable compound. For example, as shown in FIGS. 1A through 1H, the collar 100 may include a vibrational indicator 60.

The operation 5518 illustrates providing an electromagnetic indication of dispensing of the inhalable compound. For example, as shown in FIGS. 1A through 1H, the collar 100 may include an electromagnetic indicator 62.

FIG. 56 illustrates an operational flow 5600 representing example operations related to maintaining a hands-free article for dispensing an inhalable compound according to a dosing instruction set, where the hands-free article is maintained in an operable dispensing position. In FIG. 56 and in following figures that include various examples of operational flows, discussion and explanation may be provided with respect to the above-described examples of FIGS. 1A through 1H, and/or with respect to other examples and contexts. However, it should be understood that the operational flows may be executed in a number of other environments and contexts, and/or in modified versions of FIGS. 1A through 1H. Also, although the various operational flows are presented in the sequence(s) illustrated, it should be understood that the various operations may be performed in other orders than those which are illustrated, or may be performed concurrently.

After a start operation, the operational flow 5600 moves to an operation 5610. Operation 5610 depicts dispensing for inhalation by a user a dose of an inhalable compound according to a dosing instruction set. For example, as shown in FIGS. 1A through 1H, the collar 100 may dispense a dose 158 of a compound 104 according to a dosing instruction set stored in a memory 154.

Then, operation 5620 depicts maintaining in physical association with the user a hands-free article for dispensing an inhalable compound in an operable dispensing position. For example, as shown in FIGS. 1A through 1H, the collar 100 may be maintained in an operable dispensing position with an adhesive 138.

Then, operation 5630 depicts receiving the dose of the inhalable compound for dispensing. For example, as shown in FIGS. 1A through 1H, the compound 104 may be received via the reservoir 180.

FIG. 57 illustrates an operational flow 5700 representing example operations related to maintaining a hands-free article for dispensing an inhalable compound according to a dosing instruction set, where the hands-free article is maintained in an operable dispensing position. In FIG. 57 and in following figures that include various examples of operational flows, discussion and explanation may be provided with respect to the above-described examples of FIGS. 1A through 1H, and/or with respect to other examples and contexts. However, it should be understood that the operational flows may be executed in a number of other environments and contexts, and/or in modified versions of FIGS. 1A through 1H. Also, although the various operational flows are presented in the sequence(s) illustrated, it should be understood that the various operations may be performed in other orders than those which are illustrated, or may be performed concurrently.

After a start operation, the operational flow 5700 moves to an operation 5710. Operation 5710 depicts dispensing for inhalation by a user a dose of an inhalable compound according to a dosing instruction set. For example, as shown in FIGS. 1A through 1H, the collar 100 may dispense a dose 158 of a compound 104 according to a dosing instruction set stored in a memory 154.

Then, operation 5720 depicts maintaining in physical association with the user a hands-free article for dispensing an inhalable compound in an operable dispensing position. For example, as shown in FIGS. 1A through 1H, the collar 100 may be maintained in an operable dispensing position with an adhesive 138.

Then, operation 5730 depicts receiving the inhalable compound. For example, as shown in FIGS. 1A through 1H, the compound 104 may be received via the reservoir 180.

Figure 58:
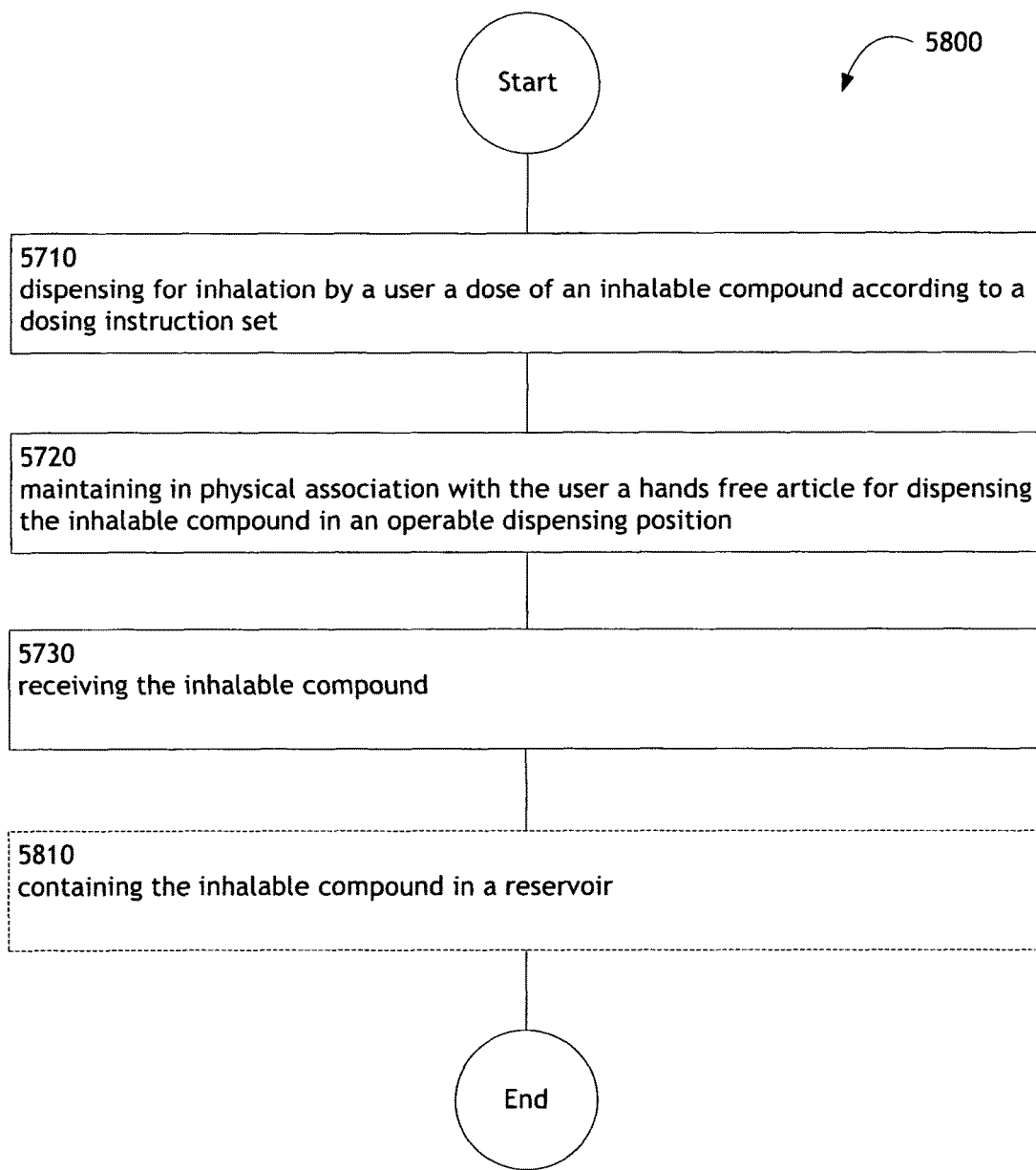
FIG. 58 illustrates an operational flow representing example operations related to maintaining a hands-free article for dispensing an inhalable compound according to a dosing instruction set, where the hands-free article is maintained in an operable dispensing position.

FIG. 58 illustrates an operational flow 5800 representing example operations related to maintaining a hands-free article for dispensing an inhalable compound according to a dosing instruction set, where the hands-free article is maintained in an operable dispensing position. FIG. 58 illustrates an example embodiment where the example operational flow 5700 of FIG. 57 may include at least one additional operation. Additional operations may include an operation 5810.

After a start operation, an operation 5710, an operation 5720, and an operation 5730, the operational flow 5800 moves to an operation 5810. Operation 5810 illustrates containing the inhalable compound in a reservoir. For example, as shown in FIGS. 1A through 1H, the compound 104 may be contained in the reservoir 180.

FIG. 59 illustrates an operational flow 5900 representing example operations related to maintaining a hands-free article for dispensing an inhalable compound according to a dosing instruction set, where the hands-free article is maintained in an operable dispensing position. In FIG. 59 and in following figures that include various examples of operational flows, discussion and explanation may be provided with respect to the above-described examples of FIGS. 1A through 1H, and/or with respect to other examples and contexts. However, it should be understood that the operational flows may be executed in a number of other environments and contexts, and/or in modified versions of FIGS. 1A through 1H. Also, although the various operational flows are presented in the sequence(s) illustrated, it should be understood that the various operations may be performed in other orders than those which are illustrated, or may be performed concurrently.

After a start operation, the operational flow 5900 moves to an operation 5910. Operation 5910 depicts dispensing for inhalation by a user a dose of an inhalable compound according to a dosing instruction set. For example, as shown in FIGS. 1A through 1H, the collar 100 may dispense a dose 158 of a compound 104 according to a dosing instruction set stored in a memory 154.

Then, operation 5920 depicts maintaining in physical association with the user a hands-free article for dispensing an inhalable compound in an operable dispensing position. For example, as shown in FIGS. 1A through 1H, the collar 100 may be maintained in an operable dispensing position with an adhesive 138.

Then, operation 5930 depicts supporting a hands-free aerosol delivery system on the body of a mammal. For example, as shown in FIGS. 1A through 1H, the collar 100 may be supported on the body of the subject 102.

FIG. 60 illustrates an operational flow 6000 representing example operations related to maintaining a hands-free article for dispensing an inhalable compound according to a dosing instruction set, where the hands-free article is maintained in an operable dispensing position. In FIG. 60 and in following figures that include various examples of operational flows, discussion and explanation may be provided with respect to the above-described examples of FIGS. 1A through 1H, and/or with respect to other examples and contexts. However, it should be understood that the operational flows may be executed in a number of other environments and contexts, and/or in modified versions of FIGS. 1A through 1H. Also, although the various operational flows are presented in the sequence(s) illustrated, it should be understood that the various operations may be performed in other orders than those which are illustrated, or may be performed concurrently.

After a start operation, the operational flow 6000 moves to an operation 6010. Operation 6010 depicts detecting a medical condition parameter of a mammal according to a medical condition parameter request. For example, as shown in FIGS. 1A through 1H, the collar 100 may utilize a sensor module 170 to detect a medical condition parameter for the subject 102 according to a request from a physician 168. The request may be received via the interface 164 and then transferred to the sensor module 170 via the processor 156.

Then, operation 6020 depicts maintaining in physical association with a user a hands-free article for dispensing an inhalable compound in an operable dispensing position. For example, as shown in FIGS. 1A through 1H, the collar 100 may be maintained in an operable dispensing position with an adhesive 138.

Then, operation 6030 depicts dispensing for inhalation by the user a dose of an inhalable compound according to a dosing instruction set. For example, as shown in FIGS. 1A through 1H, the collar 100 may dispense a dose 158 of a compound 104 according to a dosing instruction set stored in a memory 154.

Figure 61:
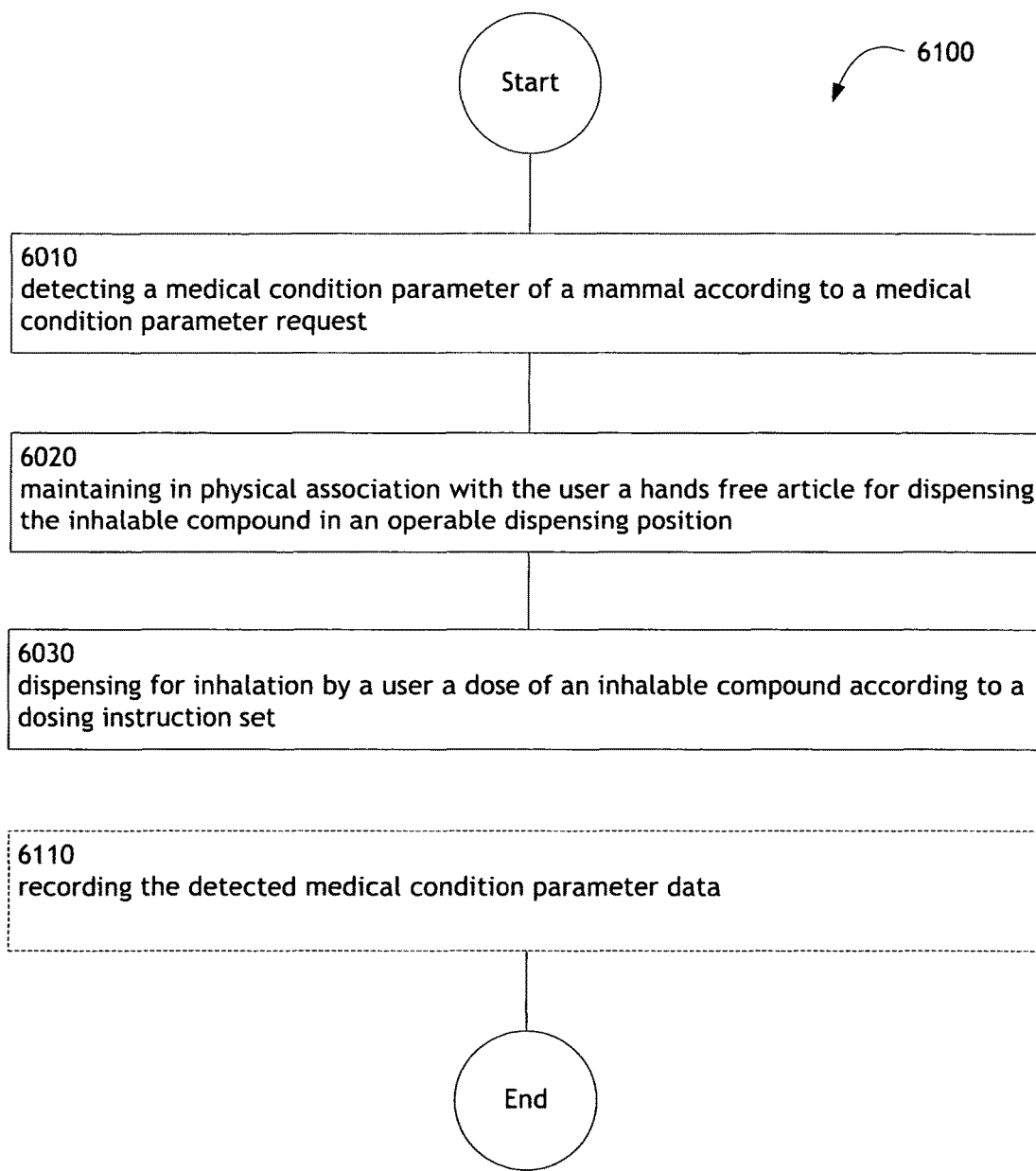
FIG. 61 illustrates an operational flow representing example operations related to maintaining a hands-free article for dispensing an inhalable compound according to a dosing instruction set, where the hands-free article is maintained in an operable dispensing position.

FIG. 61 illustrates an operational flow 6100 representing example operations related to maintaining a hands-free article for dispensing an inhalable compound according to a dosing instruction set, where the hands-free article is maintained in an operable dispensing position. FIG. 61 illustrates an example embodiment where the example operational flow 6000 of FIG. 60 may include at least one additional operation. Additional operations may include an operation 6110.

After a start operation, an operation 6010, an operation 6020, and an operation 6030, the operational flow 6100 moves to an operation 6110. Operation 6110 illustrates recording the detected medical condition parameter data. It will be appreciated that a steep state may be included as a medical condition. For example, as shown in FIGS. 1A through 1H, the detected medical condition data may be recorded to the memory 154.

Figure 62:
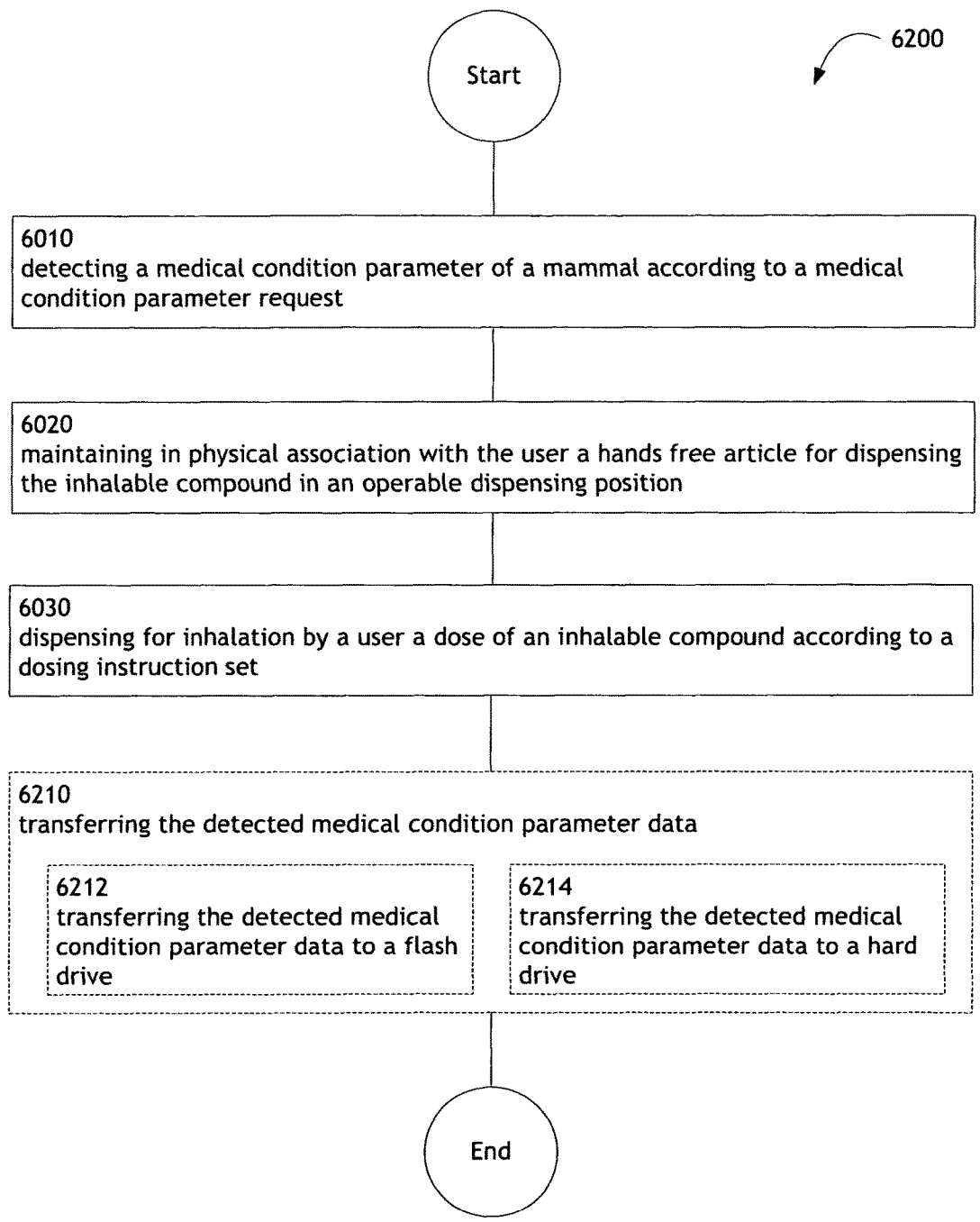
FIG. 62 illustrates an operational flow representing example operations related to maintaining a hands-free article for dispensing an inhalable compound according to a dosing instruction set, where the hands-free article is maintained in an operable dispensing position.

FIG. 62 illustrates an operational flow 6200 representing example operations related to maintaining a hands-free article for dispensing an inhalable compound according to a dosing instruction set, where the hands-free article is maintained in an operable dispensing position. FIG. 62 illustrates an example embodiment where the example operational flow 6000 of FIG. 60 may include at least one additional operation. Additional operations may include an operation 6210, an operation 6212, and/or an operation 6214.

After a start operation, an operation 6010, an operation 6020, and an operation 6030, the operational flow 6200 moves to an operation 6210. Operation 6210 illustrates transferring the detected medical condition parameter data. For example, as shown in FIGS. 1A through 1H, the detected medical condition data stored in the memory 154 may be transferred to a flash drive 64.

The operation 6212 illustrates transferring the detected medical condition parameter data to a flash drive. For example, as shown in FIGS. 1A through 1H, the detected medical condition data stored in the memory 154 may be transferred to a flash drive 64.

The operation 6214 illustrates transferring the detected medical condition parameter data to a hard drive. For example, as shown in FIGS. 1A through 1H, the detected medical condition data stored in the memory 154 may be transferred to a hard drive 66.

Figure 63:
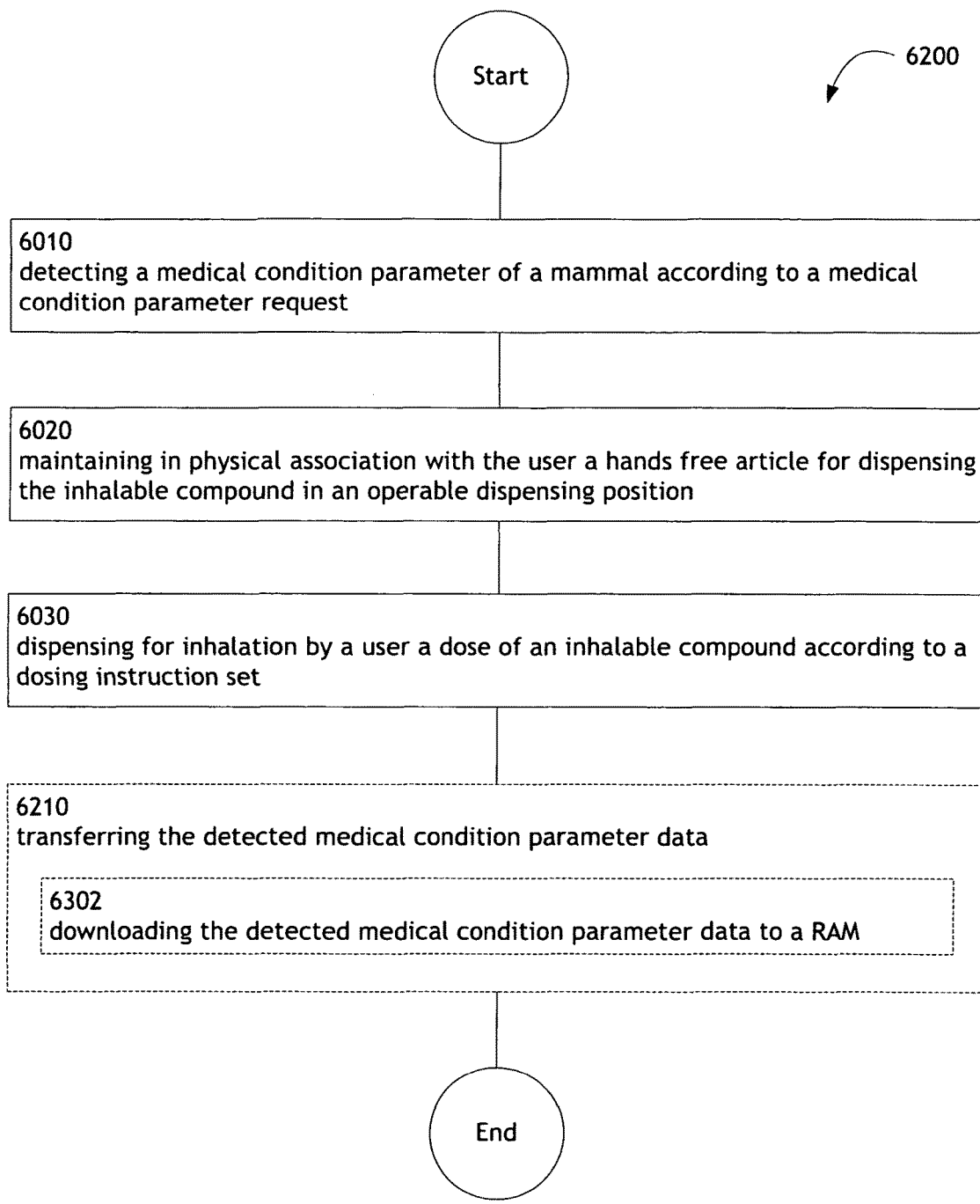
FIG. 63 illustrates an alternative embodiment of the operational flow of FIG. 62.

FIG. 63 illustrates alternative embodiments of the example operational flow 6200 of FIG. 62. FIG. 63 illustrates example embodiments where the operation 6210 may include at least one additional operation. Additional operations may include an operation 6302.

The operation 6302 illustrates downloading the detected medical condition parameter data to a RAM. For example, as shown in FIGS. 1A through 1H, the detected medical condition data stored in the memory 154 may be downloaded to a random access memory (RAM) 68. In an embodiment, the detected medical condition data may be transmitted to a processor (e.g., processor 156). In an embodiment, the detected medical condition may be transmitted to an external site (e.g., the medical response unit 192).

Figure 64:
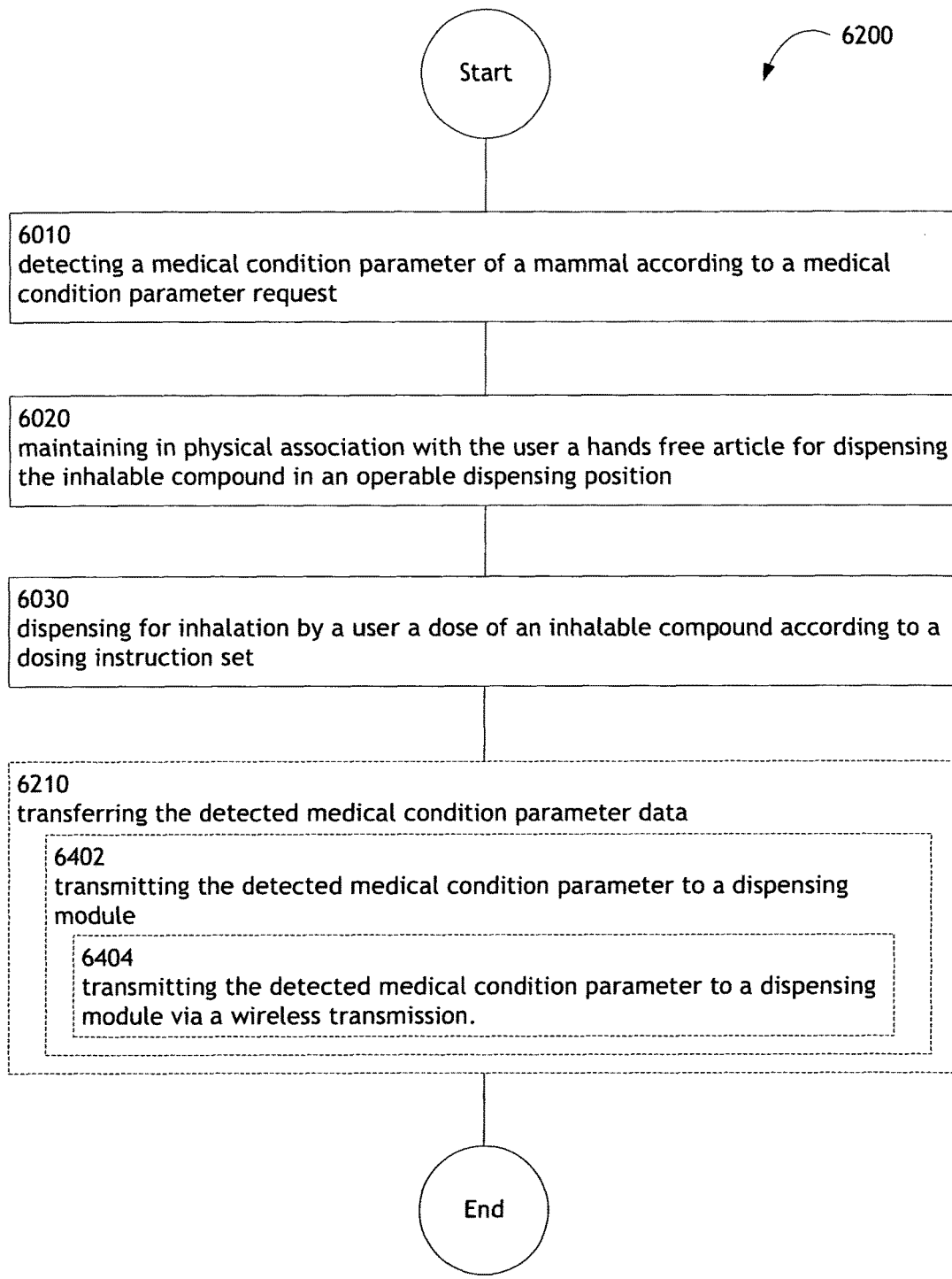
FIG. 64 illustrates an alternative embodiment of the operational flow of FIG. 62.

FIG. 64 illustrates alternative embodiments of the example operational flow 6200 of FIG. 62. FIG. 64 illustrates example embodiments where the operation 6210 may include at least one additional operation. Additional operations may include an operation 6402, and/or an operation 6404.

The operation 6402 illustrates transmitting the detected medical condition parameter to a dispensing module. For example, as shown in FIGS. 1A through 1H, the detected medical condition data stored in the memory 154 may be transmitted to the dispensing module 128. Further, the operation 6404 illustrates transmitting the detected medical condition parameter to a dispensing module via a wireless transmission. For example, as shown in FIGS. 1A through 1H, the detected medical condition data stored in the memory 154 may be transmitted to the dispensing module 128 wirelessly.

Figure 65:
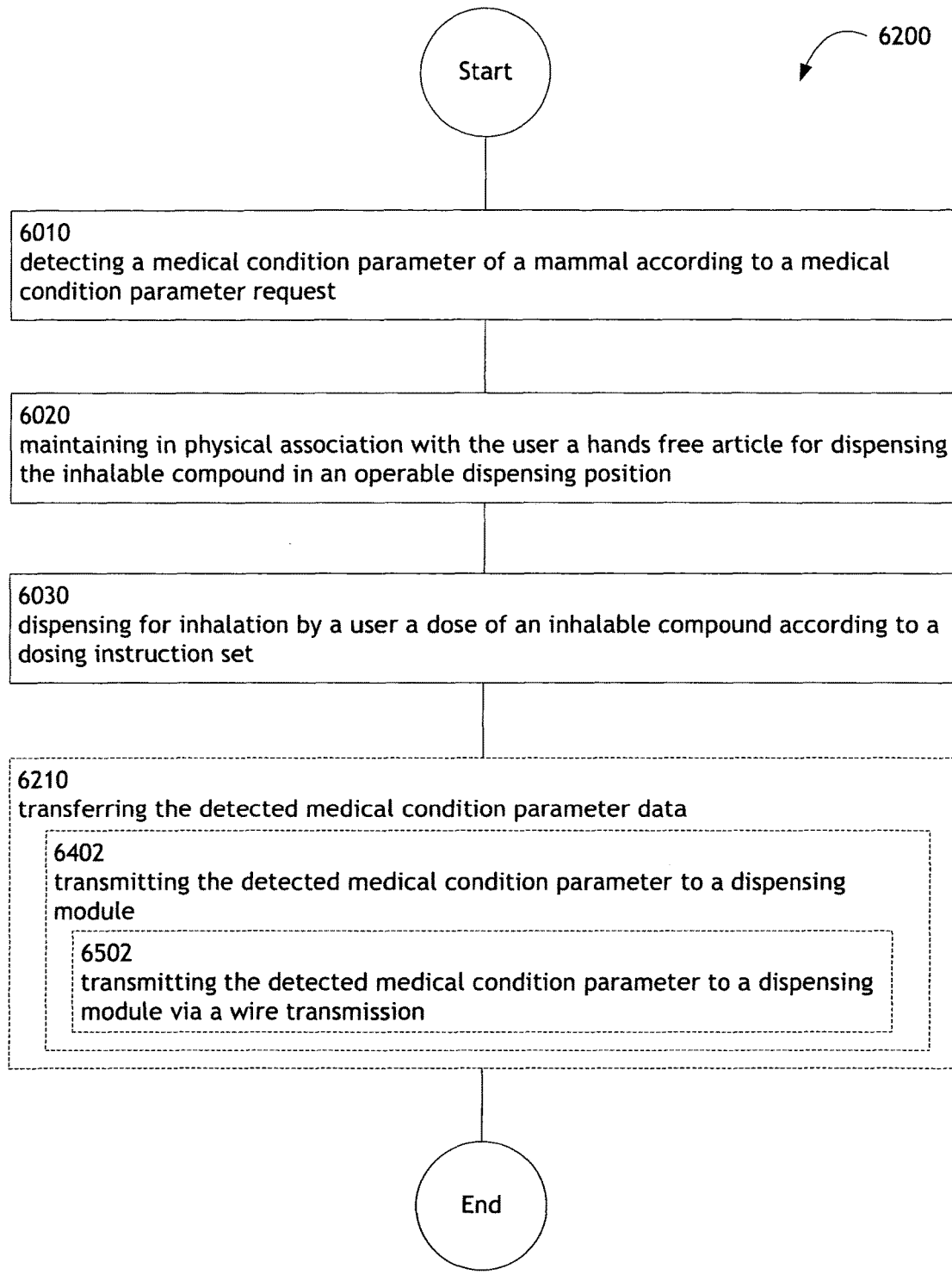
FIG. 65 illustrates an alternative embodiment of the operational flow of FIG. 62.

FIG. 65 illustrates alternative embodiments of the example operational flow 6200 of FIG. 62. FIG. 65 illustrates example embodiments where the operation 6210 may include at least one additional operation. Additional operations may include an operation 6502. Further, the operation 6502 illustrates transmitting the detected medical condition parameter to a dispensing module via a wire transmission. For example, as shown in FIGS. 1A through 1H, the detected medical condition data stored in the memory 154 may be transmitted to the dispensing module 128 via a wired connection.

Figure 66:
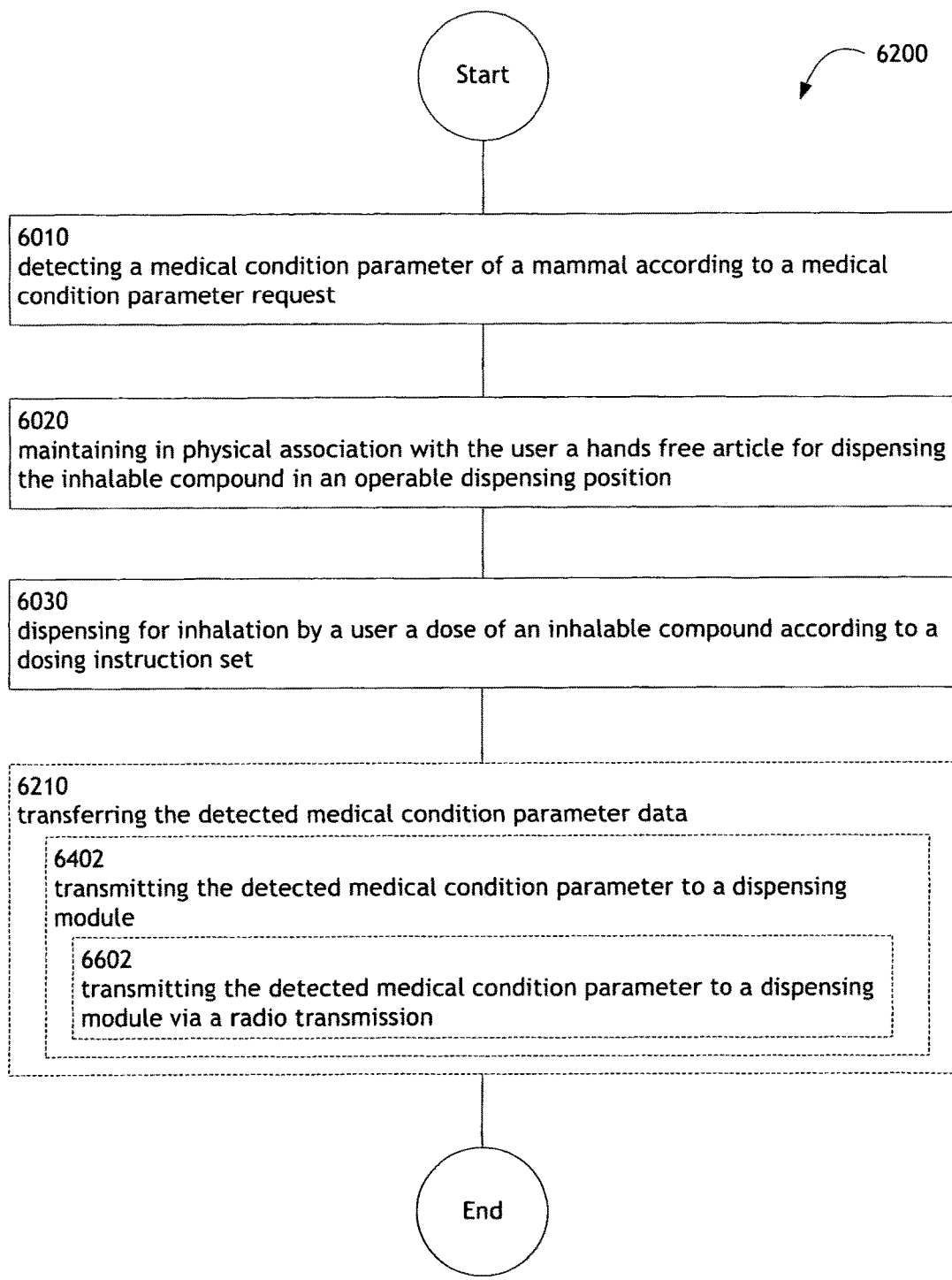
FIG. 66 illustrates an alternative embodiment of the operational flow of FIG. 62.

FIG. 66 illustrates alternative embodiments of the example operational flow 6200 of FIG. 62. FIG. 66 illustrates example embodiments where the operation 6210 may include at least one additional operation. Additional operations may include an operation 6602. Further, the operation 6602 illustrates transmitting the detected medical condition parameter to a dispensing module via a radio transmission. For example, as shown in FIGS. 1A through 1H, the detected medical condition data stored in the memory 154 may be transmitted to the dispensing module 128 via a radio signal.

Figure 67:
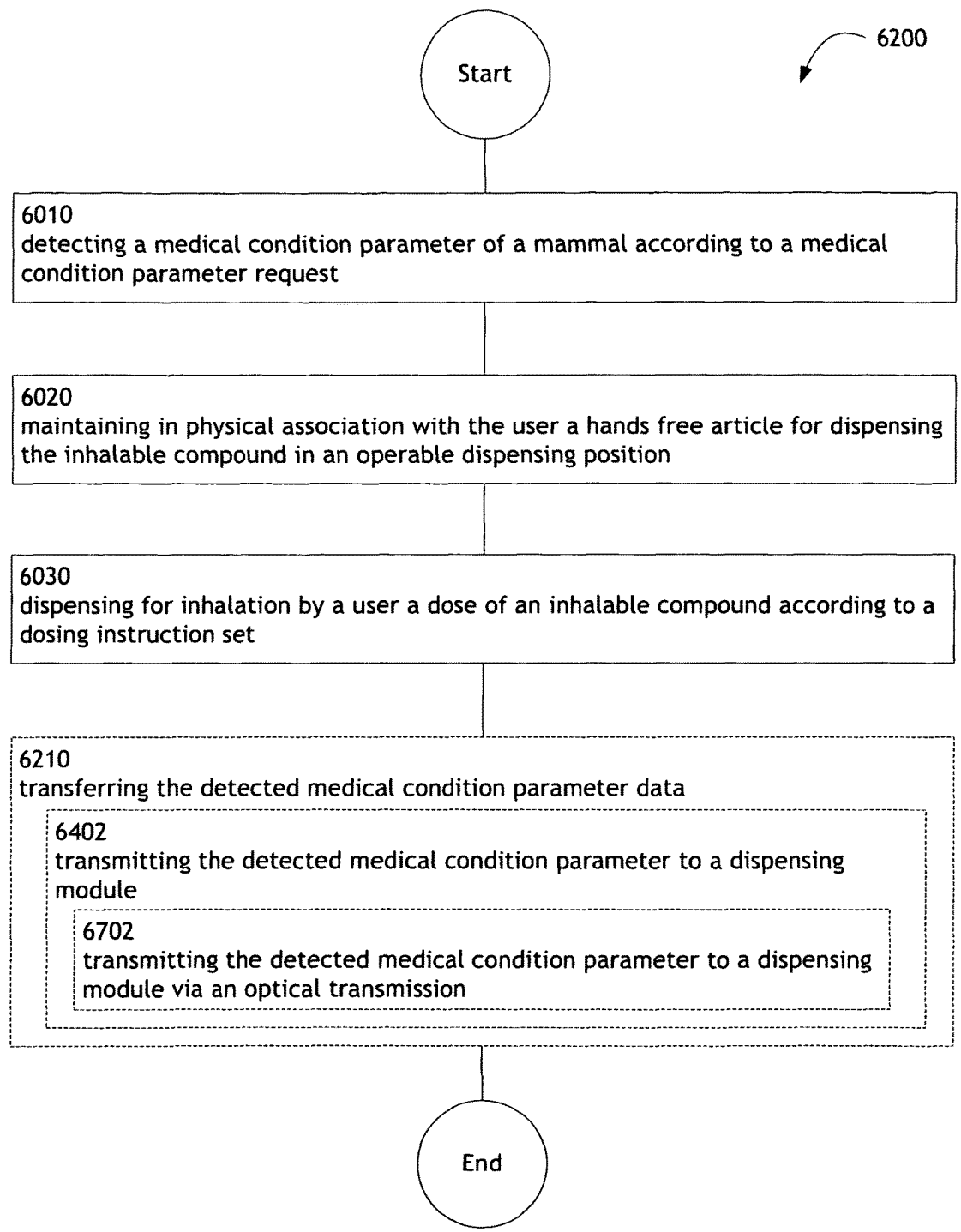
FIG. 67 illustrates an alternative embodiment of the operational flow of FIG. 62.

FIG. 67 illustrates alternative embodiments of the example operational flow 6200 of FIG. 62. FIG. 67 illustrates example embodiments where the operation 6210 may include at least one additional operation. Additional operations may include an operation 6702. Further, the operation 6702 illustrates transmitting the detected medical condition parameter to a dispensing module via an optical transmission. For example, as shown in FIGS. 1A through 1H, the detected medical condition data stored in the memory 154 may be transmitted to the dispensing module 128 via an optical transmission.

Figure 68:
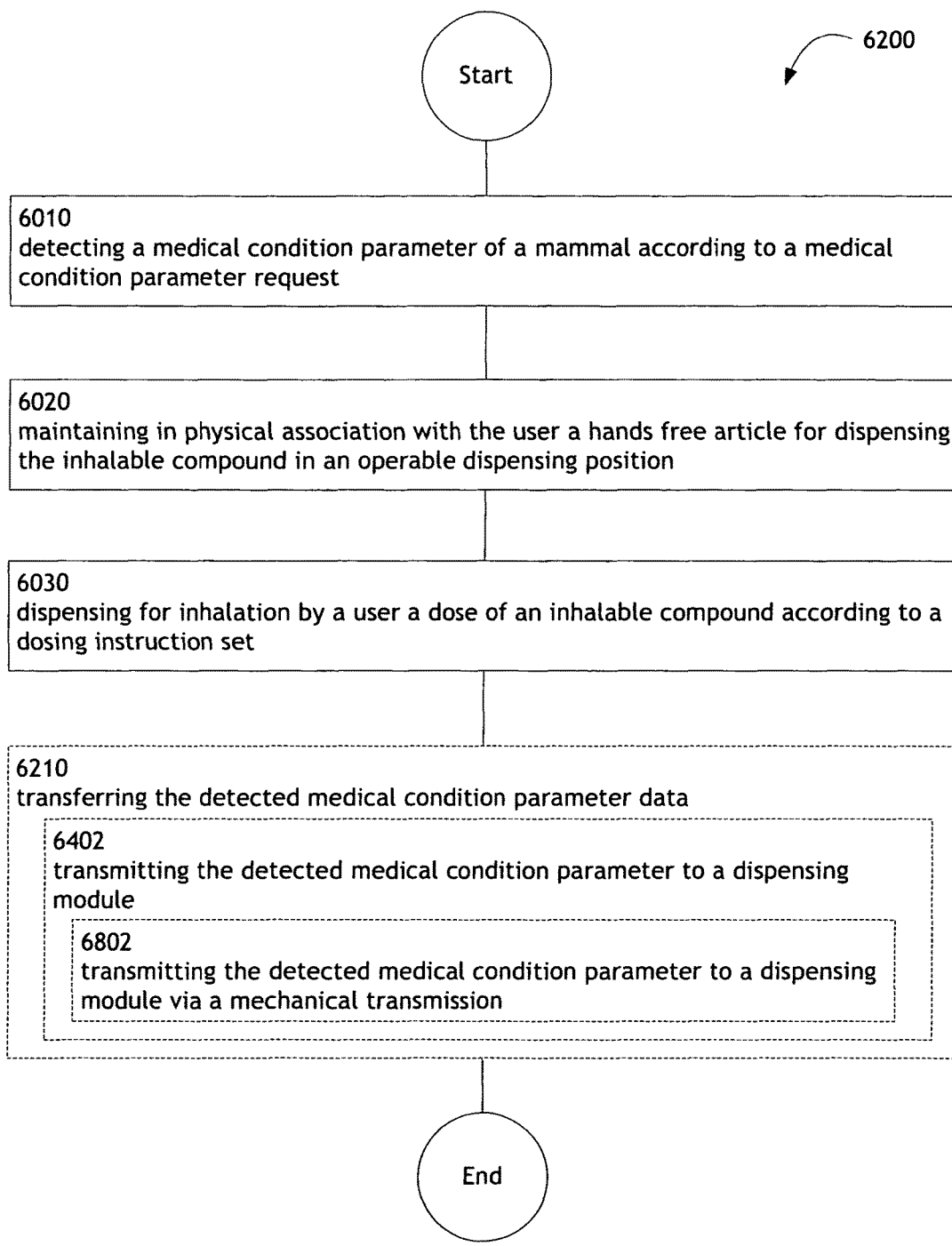
FIG. 68 illustrates an alternative embodiment of the operational flow of FIG. 62.

FIG. 68 illustrates alternative embodiments of the example operational flow 6200 of FIG. 62. FIG. 68 illustrates example embodiments where the operation 6210 may include at least one additional operation. Additional operations may include an operation 6802. Further, the operation 6802 illustrates transmitting the detected medical condition parameter to a dispensing module via a mechanical transmission. For example, as shown in FIGS. 1A through 1H, the detected medical condition data stored in the memory 154 may be transmitted to the dispensing module 128 via a mechanical transmission.

In an embodiment, the collar 100 may include a metered dose inhaler for delivering a metered dosage of an inhaled bronchodilator when the sensor module 170 detects a condition (e.g., an asthmatic incident including narrowing of the subject's airways) or a symptom indicative of a condition (e.g., narrowing of the subject's airways, wheezing, or decreased exhalation volume). In an embodiment, the sensor module 170 transmits the detected condition or symptom to the processor 156. The processor 156 utilizes information stored in the memory 154 to determine the most appropriate course of action for the detected condition/symptom. For example, the memory 154 may include instructions for dispensing (e.g., via the dispensing module 128) a metered dose of the inhaled bronchodilator (which is stored in reservoir 180) when the incident is detected. In an embodiment, the memory 154 includes instructions for subsequent administration of the bronchodilator at some time after the initial condition/symptom is detected (e.g., in the case of a late-phase allergic reaction). The memory 154 may also include instructions for activating a visual indicator 196 so that the subject 102 or an observer may be alerted to the subject's condition.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/ /implemented/translated/ converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution.

Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art wilt recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electromechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback Loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although user 166 is shown/described herein as a single illustrated figure, those skilled in the art will appreciate that user 166 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

The invention claimed is:

1. A method for administering an inhalable compound, comprising:
    detecting a medical condition parameter of a user with a sensor on a hands-free article for dispensing an inhalable compound according to a medical condition parameter request received from a source external to the hands-free article;
    maintaining in physical association with the user the hands-free article in an operable dispensing position, the operable dispensing position excluding physical contact between an outlet of the hands-free article and a face of the user; and
    dispensing for inhalation by the user a dose of the inhalable compound according to a dosing instruction set.

2. The method of claim 1, wherein detecting a medical condition parameter of a user with a sensor on a hands-free article for dispensing an inhalable compound according to a medical condition parameter request received from a source external to the hands-free article comprises:
    detecting a blood glucose level in the user.

3. The method of claim 1, wherein detecting a medical condition parameter of a user with a sensor on a hands-free article for dispensing an inhalable compound according to a medical condition parameter request received from a source external to the hands-free article comprises:
    detecting a blood oxygen level in the user.

4. The method of claim 1, wherein detecting a medical condition parameter of a user with a sensor on a hands-free article for dispensing an inhalable compound according to a medical condition parameter request received from a source external to the hands-free article comprises:
    detecting an infection in the user.

5. The method of claim 1, wherein detecting a medical condition parameter of a user with a sensor on a hands-free article for dispensing an inhalable compound according to a medical condition parameter request received from a source external to the hands-free article comprises:

detecting vascular dysfunction in the user.

6. The method of claim 1, wherein detecting a medical condition parameter of a user with a sensor on a hands-free article for dispensing an inhalable compound according to a medical condition parameter request received from a source external to the hands-free article comprises:

detecting blood flow in the user.

7. The method of claim 1, wherein detecting a medical condition parameter of a user with a sensor on a hands-free article for dispensing an inhalable compound according to a medical condition parameter request received from a source external to the hands-free article comprises:

detecting at least one of a respiratory minute volume in the user, a sneeze, a cough, a wheeze, a rhonchus, a snore, a temperature, or an expelled gas.

8. The method of claim 1, further comprising:

recording the detected medical condition parameter data.

9. The method of claim 1, further comprising:

transferring the detected medical condition parameter data.

10. The method of claim 9, wherein transferring the detected medical condition parameter data comprises:

transferring the detected medical condition parameter data to a flash drive.

11. The method of claim 9, wherein transferring the detected medical condition parameter data comprises:

transferring the detected medical condition parameter data to a hard drive.

12. The method of claim 9, wherein transferring the detected medical condition parameter data comprises:

downloading the detected medical condition parameter data to a RAM.

13. The method of claim 9, wherein transferring the detected medical condition parameter data comprises:

transmitting the detected medical condition parameter data to a processor.

14. The method of claim 9, wherein transferring the detected medical condition parameter data comprises:

transmitting the detected medical condition parameter data to an external site.

15. The method of claim 9, wherein transferring the detected medical condition parameter data comprises:

transmitting the detected medical condition parameter to a dispensing module.

16. The method of claim 15, wherein transmitting the detected medical condition parameter to a dispensing module comprises:

transmitting the detected medical condition parameter to a dispensing module via a wireless transmission.

17. The method of claim 15, wherein transmitting the detected medical condition parameter to a dispensing module comprises:

transmitting the detected medical condition parameter to a dispensing module via a wire transmission.

18. The method of claim 15, wherein transmitting the detected medical condition parameter to a dispensing module comprises:

transmitting the detected medical condition parameter to a dispensing module via a radio transmission.

19. The method of claim 15, wherein transmitting the detected medical condition parameter to a dispensing module further comprises:

transmitting the detected medical condition parameter to a dispensing module via an optical transmission.

20. The method of claim 15, wherein transmitting the detected medical condition parameter to a dispensing module further comprises:

transmitting the detected medical condition parameter to a dispensing module via a mechanical transmission.

21. A method for administering an inhalable compound, comprising:

detecting a medical condition parameter of a user with a sensor on a hands-free article for dispensing an inhalable compound according to a medical condition parameter request received from a source external to the hands-free article;

maintaining in physical association with a user the hands-free article, the hands free article configured for disposal around at least one of a neck portion, a torso portion, or a wrist portion of the user, the hands free article including a support member configured for maintaining the inhalable compound in an operable dispensing position, the operable dispensing position oriented to exclude physical contact between an outlet of the hands-free article and a face of the user; and dispensing for inhalation by the user a dose of the inhalable compound according to a dosing instruction set.

* * * * *